United States Patent
Sugahara et al.

(10) Patent No.: US 12,018,056 B2
(45) Date of Patent: Jun. 25, 2024

(54) HIGHLY CONTRACTED SYNTHETIC FIBROIN FIBER, PRODUCTION METHOD THEREFOR, AND METHOD FOR CONTRACTING SYNTHETIC FIBROIN FIBER

(71) Applicants: Spiber Inc., Yamagata (JP); Kojima Industries Corporation, Aichi (JP)

(72) Inventors: Junichi Sugahara, Tsuruoka (JP); Keisuke Morita, Tsuruoka (JP); Hiroyuki Nakamura, Tsuruoka (JP)

(73) Assignee: Spiber Inc., Yamagata (JP)

( * ) Notice: Subject to any disclaimer, the term of this patent is extended or adjusted under 35 U.S.C. 154(b) by 595 days.

(21) Appl. No.: 16/491,640

(22) PCT Filed: Mar. 5, 2018

(86) PCT No.: PCT/JP2018/008199
§ 371 (c)(1),
(2) Date: Sep. 6, 2019

(87) PCT Pub. No.: WO2018/164021
PCT Pub. Date: Sep. 13, 2018

(65) Prior Publication Data
US 2020/0031887 A1 Jan. 30, 2020

(30) Foreign Application Priority Data
Mar. 10, 2017 (JP) .................... 2017-046524

(51) Int. Cl.
C07K 14/435 (2006.01)
D01D 10/00 (2006.01)
D01F 4/02 (2006.01)

(52) U.S. Cl.
CPC ....... *C07K 14/43518* (2013.01); *D01D 10/00* (2013.01); *D01F 4/02* (2013.01)

(58) Field of Classification Search
None
See application file for complete search history.

(56) References Cited

U.S. PATENT DOCUMENTS

| | | | |
|---|---|---|---|
| 2005/0010035 A1 | 1/2005 | Lewis et al. | |
| 2012/0231499 A1 | 9/2012 | Lee et al. | |
| 2014/0058066 A1 | 2/2014 | Sekiyama et al. | |
| 2015/0141618 A1 | 5/2015 | Ishikawa et al. | |
| 2019/0135881 A1* | 5/2019 | Morita ............ | C07K 14/43518 |
| 2020/0207817 A1* | 7/2020 | Morita ............ | C07K 14/43518 |

FOREIGN PATENT DOCUMENTS

| | | |
|---|---|---|
| CN | 1364948 A | 8/2002 |
| CN | 1566422 A | 1/2005 |
| CN | 101395178 A | 3/2009 |
| CN | 102906107 A | 1/2013 |
| CN | 103502516 A | 1/2014 |
| CN | 104395511 A | 3/2015 |
| CN | 111712514 A | 9/2020 |
| EP | 0452925 A2 | 10/1991 |
| EP | 3323307 A1 | 5/2018 |
| JP | H06-098771 A | 4/1994 |
| JP | 2005-502347 A | 1/2005 |
| JP | 2009-121003 A | 6/2009 |
| JP | 2009-521921 A | 6/2009 |
| JP | 2013-506058 A | 2/2013 |
| JP | 2013-528568 A | 7/2013 |
| JP | 2014-129639 A | 7/2014 |
| KR | 10-2011-0102757 A | 9/2011 |
| RU | 2323282 C1 | 4/2008 |
| WO | 03/020916 A2 | 3/2003 |
| WO | 2007/078239 A2 | 7/2007 |
| WO | 2011/038401 A2 | 3/2011 |
| WO | 2011/112046 A2 | 9/2011 |
| WO | 2011/113592 A1 | 9/2011 |
| WO | 2012/165476 A1 | 12/2012 |
| WO | 2013/065651 A1 | 5/2013 |
| WO | 2014/002605 A1 | 1/2014 |
| WO | 2014/062134 A1 | 4/2014 |
| WO | 2018/087239 A1 | 5/2018 |
| WO | 2019/067745 A1 | 4/2019 |

OTHER PUBLICATIONS

International Search Report issued in corresponding International Patent Application No. PCT/2018/008199 dated May 22, 2018.
International Preliminary Report on Patentability and Written Opinion issued in corresponding International Patent Application No. PCT/JP2018/008199 dated Sep. 19, 2019.
Shao et al., "Analysis of spider silk in native and supercontracted states using Raman spectroscopy," Polymer, 40: 2493-2500 (1998).
Guan et al., "Two Mechanisms for Supercontraction in Nephila Spider Dragline silk," Biomacromolecules, 12: 4030-4035 (2011).
Extended European Search Report issued in counterpart European Patent Application No. 18764784.7 dated Nov. 13, 2020.
Notification of Information Provision filed in European Patent Application No. 18764784.7 dated Apr. 4, 2024.

* cited by examiner

*Primary Examiner* — Anand U Desai
(74) *Attorney, Agent, or Firm* — Morgan, Lewis & Bockius LLP

(57) ABSTRACT

The present invention relates to a highly contracted artificial fibroin fiber including a modified fibroin, in which a contraction percentage defined by the following equation exceeds 7%.

Contraction percentage={1−(length of contracted artificial fibroin fiber/length of artificial fibroin fiber before being brought into contact with water after spinning)}×100(%)

8 Claims, 6 Drawing Sheets
Specification includes a Sequence Listing.

Fig.6
(a)
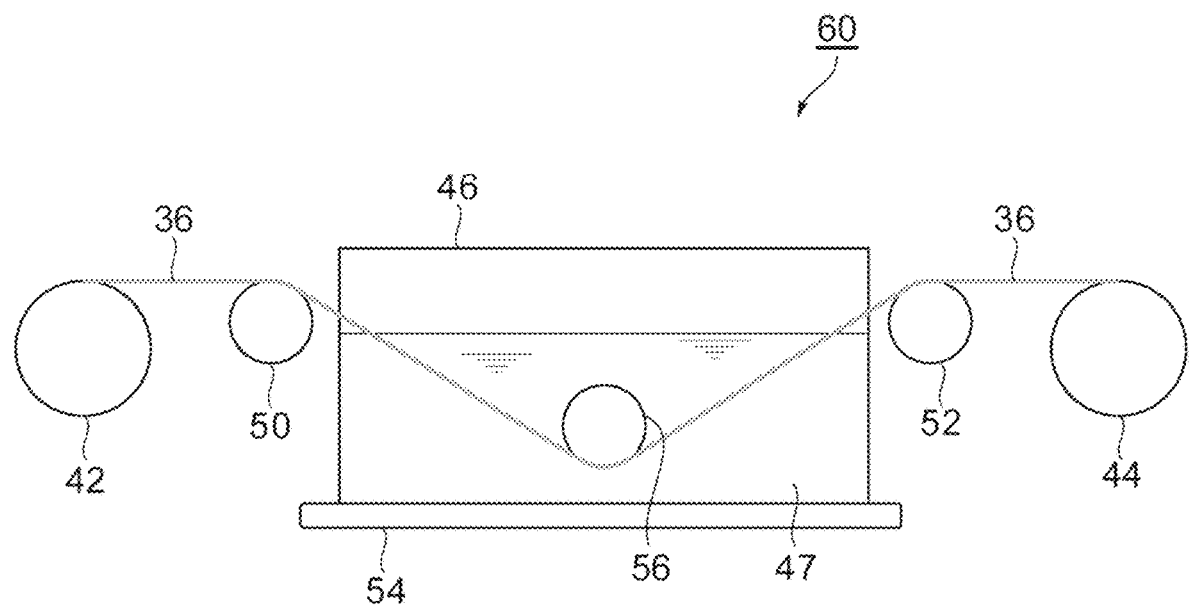
(b)
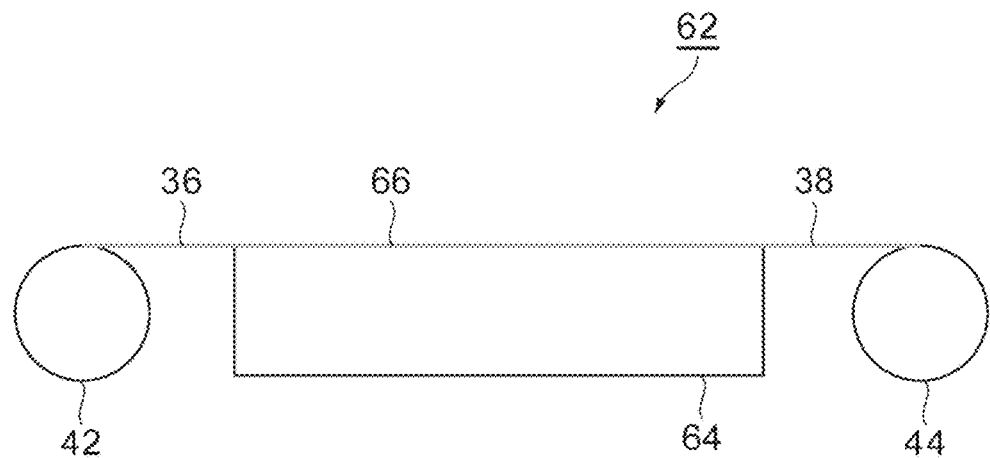

SEQUENCE LISTING

<160> NUMBER OF SEQ ID NOS: 19

<210> SEQ ID NO 1
<211> LENGTH: 597
<212> TYPE: PRT
<213> ORGANISM: Artificial Sequence
<220> FEATURE:
<223> OTHER INFORMATION: Met-PRT313

<400> SEQUENCE: 1

```
Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
                20                  25                  30

Gly Ser Ala Ala Ala Ala Gly Gly Tyr Gly Pro Gly Gly Gln Gly
            35                  40                  45

Pro Gly Gln Gln Gly Pro Gly Ser Ser Ala Ala Ala Ala Gly Pro
    50                  55                  60

Gly Gly Tyr Gly Pro Gly Gly Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gly Tyr Gly Pro Gly Gly Gln Gly Pro Gly Gln Gln
                100                 105                 110

Gly Pro Gly Ser Ser Ala Ala Ala Ala Gly Gly Tyr Gly Ser Gly
        115                 120                 125

Pro Gly Gln Gln Gly Pro Tyr Gly Ser Ala Ala Ala Ala Gly Pro
    130                 135                 140

Gly Ser Gly Gly Tyr Gly Gln Gly Pro Tyr Gly Pro Gly Ala Ser Ala
145                 150                 155                 160

Ala Ala Ala Gly Pro Gly Gly Tyr Gly Pro Gly Gly Gln Gly Pro
                165                 170                 175

Ser Ala Ser Ala Ala Ala Ala Gly Ser Gly Gln Gln Gly Pro Gly
        180                 185                 190

Gly Tyr Gly Pro Tyr Ala Ser Ala Ala Ala Ala Gly Gly Tyr Gly
    195                 200                 205

Ser Gly Pro Gly Gln Gln Gly Pro Tyr Gly Pro Gly Gly Ser Ala Ala
        210                 215                 220

Ala Ala Ala Gly Ser Gly Gln Gln Gly Pro Gly Gln Gln Gly Pro Tyr
225                 230                 235                 240

Ala Ser Ala Ala Ala Ala Gly Pro Gly Gly Gln Gly Pro Tyr Gly
                245                 250                 255

Pro Gly Ser Ser Ala Ala Ala Ala Gly Gly Tyr Gly Tyr Gly Pro
            260                 265                 270

Gly Gly Gln Gly Pro Tyr Gly Pro Gly Ala Ser Ala Ala Ala Ala
        275                 280                 285

Gly Gly Asn Gly Pro Gly Ser Gly Tyr Gly Pro Gly Gln Gln Gly
    290                 295                 300

Pro Gly Gly Ser Ala Ala Ala Ala Gly Pro Gly Gln Gln Gly Pro
305                 310                 315                 320

Tyr Gly Pro Gly Ala Ser Ala Ala Ala Ala Gly Gly Tyr Gly Pro
            325                 330                 335

Gly Gly Gln Gly Pro Gly Gly Tyr Gly Pro Gly Ser Ser Ala Ala
        340                 345                 350

Ala Ala Gly Pro Gly Gly Gln Gly Pro Tyr Gly Pro Gly Ser Ser Ala
```

355 360 365

Ala Ala Ala Gly Gly Tyr Gly Pro Gly Gln Gln Gly Pro Tyr Gly
370 375 380

Pro Gly Gly Ser Ala Ala Ala Ala Gly Gly Tyr Gln Gln Gly Pro
385 390 395 400

Gly Gly Gln Gly Pro Tyr Gly Pro Gly Ala Ser Ala Ala Ala Ala
405 410 415

Gly Pro Gly Gly Gln Gly Pro Tyr Gly Pro Gly Ala Ser Ala Ala
420 425 430

Ala Ala Gly Pro Gly Gly Tyr Gly Pro Gly Gln Gly Pro Ser Ala
435 440 445

Ser Ala Ala Ala Ala Gly Gly Tyr Gly Ser Gly Pro Gly Gly Tyr
450 455 460

Gly Pro Tyr Gly Pro Gly Gly Ser Ala Ala Ala Ala Gly Pro Gly
465 470 475 480

Ser Gly Gln Gln Gly Gln Gly Pro Tyr Gly Pro Gly Ala Ser Ala Ala
485 490 495

Ala Ala Ala Gly Gly Tyr Gly Pro Gly Gln Gln Gly Pro Tyr Gly Pro
500 505 510

Gly Gly Ser Ala Ala Ala Ala Gly Pro Gly Ser Gly Gly Tyr Gly
515 520 525

Pro Gly Ala Ser Ala Ala Ala Ala Gly Gly Asn Gly Pro Gly Ser
530 535 540

Gly Gly Tyr Gly Pro Gly Gln Gln Gly Pro Gly Gly Ser Ala Ala Ala
545 550 555 560

Ala Ala Gly Gly Tyr Gln Gln Gly Pro Gly Gln Gly Pro Tyr Gly
565 570 575

Pro Gly Ala Ser Ala Ala Ala Ala Gly Pro Gly Ser Gly Gln Gln
580 585 590

Gly Pro Gly Ala Ser
595

<210> SEQ ID NO 2
<211> LENGTH: 590
<212> TYPE: PRT
<213> ORGANISM: Artificial Sequence
<220> FEATURE:
<223> OTHER INFORMATION: Met-PRT399

<400> SEQUENCE: 2

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
                20                  25                  30

Gly Ser Gly Gly Tyr Gly Pro Gly Gln Gly Pro Gly Gln Gln Gly
            35                  40                  45

Pro Gly Ser Ser Ala Ala Ala Ala Ala Gly Pro Gly Tyr Gly Pro
50                  55                  60

Gly Gly Gln Gly Pro Ser Ala Ser Ala Ala Ala Ala Gly Pro Gly
65                  70                  75                  80

Ser Gly Gln Gln Gly Pro Gly Ala Ser Gly Gly Tyr Gly Pro Gly Gly
                85                  90                  95

Gln Gly Pro Gly Gln Gln Gly Pro Gly Ser Ser Ala Ala Ala Ala Ala
                100                 105                 110

Gly Gly Tyr Gly Ser Gly Pro Gly Gln Gln Gly Pro Tyr Gly Ser Ala

```
                 115                 120                 125
Ala Ala Ala Gly Pro Gly Ser Gly Gly Tyr Gly Gln Gly Pro Tyr
            130                 135                 140
Gly Pro Gly Ala Ser Gly Pro Gly Gly Tyr Gly Pro Gly Gln Gly
145                 150                 155                 160
Pro Ser Ala Ser Ala Ala Ala Ala Gly Ser Gln Gln Gly Pro
                    165                 170                 175
Gly Gly Tyr Gly Pro Tyr Ala Ser Ala Ala Ala Ala Gly Gly Tyr
                180                 185                 190
Gly Ser Gly Pro Gly Gln Gln Gly Pro Tyr Gly Pro Gly Ser Gly
                195                 200                 205
Ser Gly Gln Gln Gly Pro Gly Gln Gln Gly Pro Tyr Ala Ser Ala Ala
            210                 215                 220
Ala Ala Ala Gly Pro Gly Gln Gly Pro Tyr Gly Pro Gly Ser Ser
225                 230                 235                 240
Ala Ala Ala Ala Ala Gly Gly Tyr Gly Tyr Gly Pro Gly Gln Gly
                    245                 250                 255
Pro Tyr Gly Pro Gly Ala Ser Gly Gly Asn Gly Pro Gly Ser Gly Gly
            260                 265                 270
Tyr Gly Pro Gly Gln Gln Gly Pro Gly Gly Ser Ala Ala Ala Ala
                275                 280                 285
Gly Pro Gly Gly Gln Gly Pro Tyr Gly Pro Gly Ala Ser Ala Ala Ala
290                 295                 300
Ala Ala Gly Gly Tyr Gly Pro Gly Gly Gln Gly Pro Gly Gly Tyr Gly
305                 310                 315                 320
Pro Gly Ser Ser Gly Pro Gly Gly Gln Gly Pro Tyr Gly Pro Gly Ser
                    325                 330                 335
Ser Ala Ala Ala Ala Gly Gly Tyr Gly Pro Gly Gln Gln Gly Pro
                340                 345                 350
Tyr Gly Pro Gly Gly Ser Ala Ala Ala Ala Gly Gly Tyr Gln Gln
            355                 360                 365
Gly Pro Gly Gly Gln Gly Pro Tyr Gly Pro Gly Ala Ser Gly Pro Gly
370                 375                 380
Gly Gln Gly Pro Tyr Gly Pro Gly Ala Ser Ala Ala Ala Ala Gly
385                 390                 395                 400
Pro Gly Gly Tyr Gly Pro Gly Gly Gln Gly Pro Ser Ala Ser Ala Ala
                    405                 410                 415
Ala Ala Ala Gly Gly Tyr Gly Ser Gly Pro Gly Gly Tyr Gly Pro Tyr
                420                 425                 430
Gly Pro Gly Gly Ser Gly Pro Gly Ser Gly Gln Gln Gly Gln Gly Pro
                435                 440                 445
Tyr Gly Pro Gly Ala Ser Ala Ala Ala Ala Gly Gly Tyr Gly Pro
            450                 455                 460
Gly Gln Gln Gly Pro Tyr Gly Pro Gly Ser Ala Ala Ala Ala Ala
465                 470                 475                 480
Gly Pro Gly Ser Gly Gly Tyr Gly Pro Gly Ala Ser Gly Gly Asn Gly
                    485                 490                 495
Pro Gly Ser Gly Gly Tyr Gly Pro Gly Gln Gln Gly Pro Gly Gly Ser
                500                 505                 510
Ala Ala Ala Ala Ala Gly Gly Tyr Gln Gln Gly Pro Gly Gly Gln Gly
            515                 520                 525
Pro Tyr Gly Pro Gly Ala Ser Ala Ala Ala Ala Gly Gly Tyr Gly
            530                 535                 540
```

Ser Gly Pro Gly Gln Gln Gly Pro Tyr Gly Pro Gly Ser Gly Ser
545                 550                 555                 560

Gly Gln Gln Gly Pro Gly Gln Gly Pro Tyr Ala Ser Ala Ala Ala
                565                 570                 575

Ala Ala Gly Pro Gly Ser Gly Gln Gln Gly Pro Gly Ala Ser
                580                 585                 590

<210> SEQ ID NO 3
<211> LENGTH: 597
<212> TYPE: PRT
<213> ORGANISM: Artificial Sequence
<220> FEATURE:
<223> OTHER INFORMATION: Met-PRT380

<400> SEQUENCE: 3

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
                20                  25                  30

Gln Ser Ala Ala Ala Ala Gly Gln Tyr Gly Pro Gly Gln Gln Gly
            35                  40                  45

Pro Gly Gln Gln Gly Pro Gly Ser Ser Ala Ala Ala Ala Gly Pro
    50                  55                  60

Gly Gln Tyr Gly Pro Gly Gln Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gln Tyr Gly Pro Gly Gln Gln Gly Pro Gly Gln Gln
                100                 105                 110

Gly Pro Gly Ser Ser Ala Ala Ala Ala Gly Gln Tyr Gly Ser Gly
            115                 120                 125

Pro Gly Gln Gln Gly Pro Tyr Gly Ser Ala Ala Ala Ala Gly Pro
    130                 135                 140

Gly Ser Gly Gln Tyr Gly Gln Gly Pro Tyr Gly Pro Gly Ala Ser Ala
145                 150                 155                 160

Ala Ala Ala Gly Pro Gly Gln Tyr Gly Pro Gly Gln Gln Gly Pro
                165                 170                 175

Ser Ala Ser Ala Ala Ala Ala Gly Ser Gly Gln Gln Gly Pro Gly
            180                 185                 190

Gln Tyr Gly Pro Tyr Ala Ser Ala Ala Ala Ala Gly Gln Tyr Gly
    195                 200                 205

Ser Gly Pro Gly Gln Gln Gly Pro Tyr Gly Pro Gly Gln Ser Ala Ala
210                 215                 220

Ala Ala Ala Gly Ser Gly Gln Gln Gly Pro Gln Gly Pro Gly Pro Tyr
225                 230                 235                 240

Ala Ser Ala Ala Ala Ala Gly Pro Gly Gln Gln Gly Pro Tyr Gly
    245                 250                 255

Pro Gly Ser Ser Ala Ala Ala Ala Gly Gln Tyr Gly Tyr Gly Pro
    260                 265                 270

Gly Gln Gln Gly Pro Tyr Gly Pro Gly Ala Ser Ala Ala Ala Ala
    275                 280                 285

Gly Gln Asn Gly Pro Gly Ser Gly Gln Tyr Gly Pro Gly Gln Gln Gly
            290                 295                 300

Pro Gly Gln Ser Ala Ala Ala Ala Ala Gly Pro Gly Gln Gln Gly Pro
305                 310                 315                 320

-continued

Tyr Gly Pro Gly Ala Ser Ala Ala Ala Ala Gly Gln Tyr Gly Pro
                325                 330                 335
Gly Gln Gln Gly Pro Gly Gln Tyr Gly Pro Gly Ser Ser Ala Ala
            340                 345                 350
Ala Ala Gly Pro Gly Gln Gln Gly Pro Tyr Gly Pro Gly Ser Ser Ala
            355                 360                 365
Ala Ala Ala Gly Gln Tyr Gly Pro Gly Gln Gln Gly Pro Tyr Gly
            370                 375                 380
Pro Gly Gln Ser Ala Ala Ala Ala Gly Gln Tyr Gln Gln Gly Pro
385                 390                 395                 400
Gly Gln Gln Gly Pro Tyr Gly Pro Gly Ala Ser Ala Ala Ala Ala
            405                 410                 415
Gly Pro Gly Gln Gln Gly Pro Tyr Gly Pro Gly Ala Ser Ala Ala
            420                 425                 430
Ala Ala Gly Pro Gly Gln Tyr Gly Pro Gly Gln Gln Gly Pro Ser Ala
            435                 440                 445
Ser Ala Ala Ala Ala Gly Gln Tyr Gly Ser Gly Pro Gly Gln Tyr
    450                 455                 460
Gly Pro Tyr Gly Pro Gly Gln Ser Ala Ala Ala Ala Gly Pro Gly
465                 470                 475                 480
Ser Gly Gln Gln Gly Gln Gly Pro Tyr Gly Pro Gly Ala Ser Ala Ala
            485                 490                 495
Ala Ala Ala Gly Gln Tyr Gly Pro Gly Gln Gln Gly Pro Tyr Gly Pro
            500                 505                 510
Gly Gln Ser Ala Ala Ala Ala Ala Gly Pro Gly Ser Gly Gln Tyr Gly
    515                 520                 525
Pro Gly Ala Ser Ala Ala Ala Ala Gly Gln Asn Gly Pro Gly Ser
    530                 535                 540
Gly Gln Tyr Gly Pro Gly Gln Gly Pro Gln Ser Ala Ala Ala
545                 550                 555                 560
Ala Ala Gly Gln Tyr Gln Gln Gly Pro Gly Gln Gln Gly Pro Tyr Gly
            565                 570                 575
Pro Gly Ala Ser Ala Ala Ala Ala Gly Pro Gly Ser Gly Gln Gln
            580                 585                 590
Gly Pro Gly Ala Ser
        595

<210> SEQ ID NO 4
<211> LENGTH: 590
<212> TYPE: PRT
<213> ORGANISM: Artificial Sequence
<220> FEATURE:
<223> OTHER INFORMATION: Met-PRT410

<400> SEQUENCE: 4

Met Gly Pro Gly Gln Gln Gly Pro Tyr Gly Pro Gly Ala Ser Ala Ala
1               5                   10                  15
Ala Ala Ala Gly Gln Asn Gly Pro Gly Ser Gly Gln Gln Gly Pro Gly
            20                  25                  30
Gln Ser Gly Gln Tyr Gly Pro Gly Gln Gly Pro Gly Gln Gln Gly
        35                  40                  45
Pro Gly Ser Ser Ala Ala Ala Ala Gly Pro Gly Gln Tyr Gly Pro
    50                  55                  60
Gly Gln Gln Gly Pro Ser Ala Ser Ala Ala Ala Ala Gly Pro Gly
65                  70                  75                  80

```
Ser Gly Gln Gln Gly Pro Ala Ser Gly Gln Tyr Gly Pro Gly Gln
                85                  90                  95

Gln Gly Pro Gly Gln Gly Pro Gly Ser Ser Ala Ala Ala Ala Ala
            100                 105                 110

Gly Gln Tyr Gly Ser Gly Pro Gly Gln Gln Gly Pro Tyr Gly Ser Ala
            115                 120                 125

Ala Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Gly Ser Gly Gln Gln Gly Pro
                165                 170                 175

Gly Gln Tyr Gly Pro Tyr Ala Ser Ala Ala Ala Ala Gly Gln Tyr
            180                 185                 190

Gly Ser Gly Pro Gly Gln Gln Gly Pro Tyr Gly Pro Gly Ser Gly
            195                 200                 205

Ser Gly Gln Gln Gly Pro Gly Gln Gln Gly Pro Tyr Ala Ser Ala Ala
    210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
            245                 250                 255

Pro Tyr Gly Pro Gly Ala Ser Gly Gln Asn Gly Pro Gly Ser Gly Gln
            260                 265                 270

Tyr Gly Pro Gly Gln Gln Gly Pro Gly Gln Ser Ala Ala Ala Ala
            275                 280                 285

Gly Pro Gly Gln Gln Gly Pro Tyr Gly Pro Gly Ala Ser Ala Ala Ala
    290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gln Gln Gly Pro Tyr Gly Pro Gly Ser
            325                 330                 335

Ser Ala Ala Ala Ala Gly Gln Tyr Gly Pro Gly Gln Gly Pro
                340                 345                 350

Tyr Gly Pro Gly Gln Ser Ala Ala Ala Ala Gly Gln Tyr Gln Gln
            355                 360                 365

Gly Pro Gly Gln Gln Gly Pro Tyr Gly Pro Gly Ala Ser Gly Pro Gly
    370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gly Pro Ser Ala Ser Ala Ala
            405                 410                 415

Ala Ala Ala Gly Gln Tyr Gly Ser Gly Pro Gly Gln Tyr Gly Pro Tyr
    420                 425                 430

Gly Pro Gly Gln Ser Gly Pro Gly Ser Gly Gln Gln Gly Gly Pro
            435                 440                 445

Tyr Gly Pro Gly Ala Ser Ala Ala Ala Ala Gly Gln Tyr Gly Pro
            450                 455                 460

Gly Gln Gln Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
            485                 490                 495
```

```
Pro Gly Ser Gly Gln Tyr Gly Pro Gly Gln Gly Pro Gly Gln Ser
            500                 505                 510

Ala Ala Ala Ala Ala Gly Gln Tyr Gln Gln Gly Pro Gly Gln Gln Gly
        515                 520                 525

Pro Tyr Gly Pro Gly Ala Ser Ala Ala Ala Ala Gly Gln Tyr Gly
        530                 535                 540

Ser Gly Pro Gly Gln Gln Gly Pro Tyr Gly Pro Gln Ser Gly Ser
545                 550                 555                 560

Gly Gln Gln Gly Pro Gly Gln Gly Pro Tyr Ala Ser Ala Ala Ala
                565                 570                 575

Ala Ala Gly Pro Gly Ser Gly Gln Gln Gly Pro Gly Ala Ser
            580                 585                 590
```

<210> SEQ ID NO 5
<211> LENGTH: 12
<212> TYPE: PRT
<213> ORGANISM: Artificial Sequence
<220> FEATURE:
<223> OTHER INFORMATION: HisTag

<400> SEQUENCE: 5

```
Met His His His His His His Ser Ser Gly Ser Ser
1               5                   10
```

<210> SEQ ID NO 6
<211> LENGTH: 608
<212> TYPE: PRT
<213> ORGANISM: Artificial Sequence
<220> FEATURE:
<223> OTHER INFORMATION: PRT313

<400> SEQUENCE: 6

```
Met His His His His His His Ser Ser Gly Ser Ser Gly Pro Gly Gly
1               5                   10                  15

Gln Gly Pro Tyr Gly Pro Gly Ala Ser Ala Ala Ala Ala Gly Gly
            20                  25                  30

Asn Gly Pro Gly Ser Gly Gln Gln Pro Gly Gly Ser Ala Ala Ala
        35                  40                  45

Ala Ala Gly Gly Tyr Gly Pro Gly Gly Gln Gly Pro Gly Gln Gln Gly
    50                  55                  60

Pro Gly Ser Ser Ala Ala Ala Ala Ala Gly Pro Gly Tyr Gly Pro
65                  70                  75                  80

Gly Gly Gln Gly Pro Ser Ala Ser Ala Ala Ala Ala Gly Pro Gly
            85                  90                  95

Ser Gly Gln Gln Gly Pro Gly Ala Ser Ala Ala Ala Ala Gly Gly
        100                 105                 110

Tyr Gly Pro Gly Gly Gln Gly Pro Gly Gln Gln Gly Pro Gly Ser Ser
    115                 120                 125

Ala Ala Ala Ala Ala Gly Gly Tyr Gly Ser Gly Pro Gly Gln Gln Gly
130                 135                 140

Pro Tyr Gly Ser Ala Ala Ala Ala Gly Pro Gly Ser Gly Tyr
145                 150                 155                 160

Gly Gln Gly Pro Tyr Gly Pro Gly Ala Ser Ala Ala Ala Ala Gly
            165                 170                 175

Pro Gly Gly Tyr Gly Pro Gly Gly Gln Gly Pro Ser Ala Ser Ala Ala
        180                 185                 190

Ala Ala Ala Gly Ser Gly Gln Gln Gly Pro Gly Gly Tyr Gly Pro Tyr
    195                 200                 205
```

Ala Ser Ala Ala Ala Ala Gly Gly Tyr Gly Ser Gly Pro Gly Gln
    210                 215                 220

Gln Gly Pro Tyr Gly Pro Gly Gly Ser Ala Ala Ala Ala Gly Ser
225                 230                 235                 240

Gly Gln Gln Gly Pro Gly Gln Gln Gly Pro Tyr Ala Ser Ala Ala
                245                 250                 255

Ala Ala Gly Pro Gly Gly Gln Gly Pro Tyr Gly Pro Gly Ser Ser Ala
                260                 265                 270

Ala Ala Ala Ala Gly Gly Tyr Gly Tyr Gly Pro Gly Gly Gln Gly Pro
            275                 280                 285

Tyr Gly Pro Gly Ala Ser Ala Ala Ala Ala Gly Asn Gly Pro
    290                 295                 300

Gly Ser Gly Gly Tyr Gly Pro Gly Gln Gln Gly Pro Gly Gly Ser Ala
305                 310                 315                 320

Ala Ala Ala Gly Pro Gly Gly Gln Gly Pro Tyr Gly Pro Gly Ala
                325                 330                 335

Ser Ala Ala Ala Ala Gly Gly Tyr Gly Pro Gly Gly Gln Gly Pro
            340                 345                 350

Gly Gly Tyr Gly Pro Gly Ser Ser Ala Ala Ala Ala Gly Pro Gly
            355                 360                 365

Gly Gln Gly Pro Tyr Gly Pro Gly Ser Ser Ala Ala Ala Ala Gly
            370                 375                 380

Gly Tyr Gly Pro Gly Gln Gln Gly Pro Tyr Gly Pro Gly Ser Ala
385                 390                 395                 400

Ala Ala Ala Gly Gly Tyr Gln Gln Gly Pro Gly Gln Gly Pro
            405                 410                 415

Tyr Gly Pro Gly Ala Ser Ala Ala Ala Ala Gly Pro Gly Gly Gln
    420                 425                 430

Gly Pro Tyr Gly Pro Gly Ala Ser Ala Ala Ala Ala Gly Pro Gly
            435                 440                 445

Gly Tyr Gly Pro Gly Gly Gln Gly Pro Ser Ala Ser Ala Ala Ala
    450                 455                 460

Ala Gly Gly Tyr Gly Ser Gly Pro Gly Gly Tyr Gly Pro Tyr Gly Pro
465                 470                 475                 480

Gly Gly Ser Ala Ala Ala Ala Gly Pro Gly Ser Gly Gln Gln Gly
            485                 490                 495

Gln Gly Pro Tyr Gly Pro Gly Ala Ser Ala Ala Ala Ala Gly Gly
    500                 505                 510

Tyr Gly Pro Gly Gln Gln Gly Pro Tyr Gly Pro Gly Gly Ser Ala Ala
    515                 520                 525

Ala Ala Ala Gly Pro Gly Ser Gly Gly Tyr Gly Pro Gly Ala Ser Ala
530                 535                 540

Ala Ala Ala Gly Gly Asn Gly Pro Gly Ser Gly Gly Tyr Gly Pro
545                 550                 555                 560

Gly Gln Gln Gly Pro Gly Gly Ser Ala Ala Ala Ala Gly Gly Tyr
                565                 570                 575

Gln Gln Gly Pro Gly Gly Gln Gly Pro Tyr Gly Pro Gly Ala Ser Ala
                580                 585                 590

Ala Ala Ala Gly Pro Gly Ser Gly Gln Gln Gly Pro Gly Ala Ser
            595                 600                 605

<210> SEQ ID NO 7
<211> LENGTH: 601

<212> TYPE: PRT
<213> ORGANISM: Artificial Sequence
<220> FEATURE:
<223> OTHER INFORMATION: PRT399

<400> SEQUENCE: 7

```
Met His His His His His Ser Ser Gly Ser Ser Gly Pro Gly Gly
1               5                   10                  15

Gln Gly Pro Tyr Gly Pro Gly Ala Ser Ala Ala Ala Ala Gly Gly
                20                  25                  30

Asn Gly Pro Gly Ser Gly Gln Gln Gly Pro Gly Gly Ser Gly Tyr
                35                  40                  45

Gly Pro Gly Gly Gln Gly Pro Gly Gln Gln Gly Pro Gly Ser Ser Ala
    50                  55                  60

Ala Ala Ala Ala Gly Pro Gly Gly Tyr Gly Pro Gly Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gly Tyr Gly Pro Gly Gln Gly Pro Gly Gln
                100                 105                 110

Gln Gly Pro Gly Ser Ser Ala Ala Ala Ala Gly Gly Tyr Gly Ser
                115                 120                 125

Gly Pro Gly Gln Gln Gly Pro Tyr Gly Ser Ala Ala Ala Ala Gly
                130                 135                 140

Pro Gly Ser Gly Gly Tyr Gly Gln Gly Pro Tyr Gly Pro Gly Ala Ser
145                 150                 155                 160

Gly Pro Gly Gly Tyr Gly Pro Gly Gly Gln Gly Pro Ser Ala Ser Ala
                165                 170                 175

Ala Ala Ala Ala Gly Ser Gly Gln Gln Gly Pro Gly Gly Tyr Gly Pro
                180                 185                 190

Tyr Ala Ser Ala Ala Ala Ala Gly Gly Tyr Gly Ser Gly Pro Gly
                195                 200                 205

Gln Gln Gly Pro Tyr Gly Pro Gly Ser Gly Ser Gly Gln Gln Gly
                210                 215                 220

Pro Gly Gln Gln Gly Pro Tyr Ala Ser Ala Ala Ala Ala Gly Pro
225                 230                 235                 240

Gly Gly Gln Gly Pro Tyr Gly Pro Gly Ser Ser Ala Ala Ala Ala
                245                 250                 255

Gly Gly Tyr Gly Tyr Gly Pro Gly Gly Gln Gly Pro Tyr Gly Pro Gly
                260                 265                 270

Ala Ser Gly Gly Asn Gly Pro Gly Ser Gly Gly Tyr Gly Pro Gly Gln
                275                 280                 285

Gln Gly Pro Gly Gly Ser Ala Ala Ala Ala Gly Pro Gly Gly Gln
                290                 295                 300

Gly Pro Tyr Gly Pro Gly Ala Ser Ala Ala Ala Ala Gly Gly Tyr
305                 310                 315                 320

Gly Pro Gly Gly Gln Gly Pro Gly Gly Tyr Gly Pro Gly Ser Ser Gly
                325                 330                 335

Pro Gly Gly Gln Gly Pro Tyr Gly Pro Gly Ser Ser Ala Ala Ala Ala
                340                 345                 350

Ala Gly Gly Tyr Gly Pro Gly Gln Gln Gly Pro Tyr Gly Pro Gly Gly
                355                 360                 365

Ser Ala Ala Ala Ala Ala Gly Gly Tyr Gln Gln Gly Pro Gly Gly Gln
                370                 375                 380
```

Gly Pro Tyr Gly Pro Gly Ala Ser Gly Pro Gly Gln Gly Pro Tyr
385                 390                 395                 400

Gly Pro Gly Ala Ser Ala Ala Ala Ala Gly Pro Gly Gly Tyr Gly
            405                 410                 415

Pro Gly Gly Gln Gly Pro Ser Ala Ser Ala Ala Ala Ala Gly Gly
            420                 425                 430

Tyr Gly Ser Gly Pro Gly Gly Tyr Gly Pro Tyr Gly Pro Gly Ser
            435                 440                 445

Gly Pro Gly Ser Gly Gln Gln Gly Gln Gly Pro Tyr Gly Pro Gly Ala
        450                 455                 460

Ser Ala Ala Ala Ala Gly Gly Tyr Gly Pro Gly Gln Gln Gly Pro
465                 470                 475                 480

Tyr Gly Pro Gly Ser Ala Ala Ala Ala Gly Pro Gly Ser Gly
            485                 490                 495

Gly Tyr Gly Pro Gly Ala Ser Gly Gly Asn Gly Pro Gly Ser Gly Gly
            500                 505                 510

Tyr Gly Pro Gly Gln Gln Gly Pro Gly Gly Ser Ala Ala Ala Ala
            515                 520                 525

Gly Gly Tyr Gln Gln Gly Pro Gly Gln Gly Pro Tyr Gly Pro Gly
            530                 535                 540

Ala Ser Ala Ala Ala Ala Gly Gly Tyr Gly Ser Gly Pro Gly Gln
545                 550                 555                 560

Gln Gly Pro Tyr Gly Pro Gly Ser Gly Ser Gly Gln Gln Gly Pro
            565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser
        595                 600

<210> SEQ ID NO 8
<211> LENGTH: 608
<212> TYPE: PRT
<213> ORGANISM: Artificial Sequence
<220> FEATURE:
<223> OTHER INFORMATION: PRT380

<400> SEQUENCE: 8

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Ala Ala
            35                  40                  45

Ala Ala Gly Gln Tyr Gly Pro Gly Gln Gln Gly Pro Gly Gln Gln Gly
        50                  55                  60

Pro Gly Ser Ser Ala Ala Ala Ala Gly Pro Gly Gln Tyr Gly Pro
65                  70                  75                  80

Gly Gln Gln Gly Pro Ser Ala Ser Ala Ala Ala Ala Gly Pro Gly
            85                  90                  95

Ser Gly Gln Gln Gly Pro Gly Ala Ser Ala Ala Ala Ala Gly Gln
            100                 105                 110

Tyr Gly Pro Gly Gln Gln Gly Pro Gly Gln Gln Gly Pro Gly Ser Ser
        115                 120                 125

Ala Ala Ala Ala Ala Gly Gln Tyr Gly Ser Gly Pro Gly Gln Gln Gly
        130                 135                 140

```
Pro Tyr Gly Ser Ala Ala Ala Ala Gly Pro Gly Ser Gly Gln Tyr
145                 150                 155                 160

Gly Gln Gly Pro Tyr Gly Pro Gly Ala Ser Ala Ala Ala Ala Gly
            165                 170                 175

Pro Gly Gln Tyr Gly Pro Gly Gln Gln Gly Pro Ser Ala Ser Ala Ala
            180                 185                 190

Ala Ala Ala Gly Ser Gly Gln Gln Gly Pro Gly Gln Tyr Gly Pro Tyr
            195                 200                 205

Ala Ser Ala Ala Ala Ala Gly Gln Tyr Gly Ser Gly Pro Gly Gln
    210                 215                 220

Gln Gly Pro Tyr Gly Pro Gly Gln Ser Ala Ala Ala Ala Gly Ser
225             230                 235                 240

Gly Gln Gln Gly Pro Gly Gln Gly Pro Tyr Ala Ser Ala Ala Ala
            245                 250                 255

Ala Ala Gly Pro Gly Gln Gln Gly Pro Tyr Gly Pro Gly Ser Ser Ala
            260                 265                 270

Ala Ala Ala Ala Gly Gln Tyr Gly Tyr Gly Pro Gly Gln Gln Gly Pro
            275                 280                 285

Tyr Gly Pro Gly Ala Ser Ala Ala Ala Ala Gly Gln Asn Gly Pro
290                 295                 300

Gly Ser Gly Gln Tyr Gly Pro Gly Gln Gln Gly Pro Gly Gln Ser Ala
305             310                 315                 320

Ala Ala Ala Ala Gly Pro Gly Gln Gln Gly Pro Tyr Gly Pro Gly Ala
            325                 330                 335

Ser Ala Ala Ala Ala Gly Gln Tyr Gly Pro Gly Gln Gln Gly Pro
            340                 345                 350

Gly Gln Tyr Gly Pro Gly Ser Ser Ala Ala Ala Ala Gly Pro Gly
            355                 360                 365

Gln Gln Gly Pro Tyr Gly Pro Gly Ser Ser Ala Ala Ala Ala Gly
            370                 375                 380

Gln Tyr Gly Pro Gly Gln Gln Gly Pro Tyr Gly Pro Gly Gln Ser Ala
385                 390                 395                 400

Ala Ala Ala Ala Gly Gln Tyr Gln Gln Gly Pro Gly Gln Gln Gly Pro
            405                 410                 415

Tyr Gly Pro Gly Ala Ser Ala Ala Ala Ala Gly Pro Gly Gln Gln
            420                 425                 430

Gly Pro Tyr Gly Pro Gly Ala Ser Ala Ala Ala Ala Gly Pro Gly
            435                 440                 445

Gln Tyr Gly Pro Gly Gln Gln Gly Pro Ser Ala Ser Ala Ala Ala Ala
450                 455                 460

Ala Gly Gln Tyr Gly Ser Gly Pro Gly Gln Tyr Gly Pro Tyr Gly Pro
465                 470                 475                 480

Gly Gln Ser Ala Ala Ala Ala Ala Gly Pro Gly Ser Gly Gln Gln Gly
            485                 490                 495

Gln Gly Pro Tyr Gly Pro Gly Ala Ser Ala Ala Ala Ala Gly Gln
            500                 505                 510

Tyr Gly Pro Gly Gln Gln Gly Pro Tyr Gly Pro Gly Gln Ser Ala Ala
            515                 520                 525

Ala Ala Ala Gly Pro Gly Ser Gly Gln Tyr Gly Pro Gly Ala Ser Ala
            530                 535                 540

Ala Ala Ala Gly Gln Asn Gly Pro Gly Ser Gly Gln Tyr Gly Pro
545                 550                 555                 560

Gly Gln Gln Gly Pro Gly Gln Ser Ala Ala Ala Ala Ala Gly Gln Tyr
```

-continued

```
                565                 570                 575
Gln Gln Gly Pro Gly Gln Gln Gly Pro Tyr Gly Pro Gly Ala Ser Ala
            580                 585                 590
Ala Ala Ala Ala Gly Pro Gly Ser Gly Gln Gln Gly Pro Gly Ala Ser
            595                 600                 605

<210> SEQ ID NO 9
<211> LENGTH: 601
<212> TYPE: PRT
<213> ORGANISM: Artificial Sequence
<220> FEATURE:
<223> OTHER INFORMATION: PRT410

<400> SEQUENCE: 9

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
            35                  40                  45

Gly Pro Gly Gln Gln Gly Pro Gly Gln Gln Gly Pro Gly Ser Ser Ala
        50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Gln Tyr Gly Ser
            115                 120                 125

Gly Pro Gly Gln Gln Gly Pro Tyr Gly Ser Ala Ala Ala Ala Ala Gly
        130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Gly Ser Gly Gln Gln Gly Pro Gly Gln Tyr Gly Pro
            180                 185                 190

Tyr Ala Ser Ala Ala Ala Ala Gly Gln Tyr Gly Ser Gly Pro Gly
            195                 200                 205

Gln Gln Gly Pro Tyr Gly Pro Gly Gln Ser Gly Ser Gly Gln Gln Gly
        210                 215                 220

Pro Gly Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
                245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
            275                 280                 285

Gln Gly Pro Gly Gln Ser Ala Ala Ala Ala Gly Pro Gly Gln Gln
        290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
```

```
                    325                 330                 335
Pro Gly Gln Gln Gly Pro Tyr Gly Pro Gly Ser Ser Ala Ala Ala Ala
                340                 345                 350
Ala Gly Gln Tyr Gly Pro Gly Gln Gln Gly Pro Tyr Gly Pro Gly Gln
                355                 360                 365
Ser Ala Ala Ala Ala Gly Gln Tyr Gln Gly Pro Gly Gln Gln
            370                 375                 380
Gly Pro Tyr Gly Pro Gly Ala Ser Gly Pro Gln Gln Gly Pro Tyr
385                 390                 395                 400
Gly Pro Gly Ala Ser Ala Ala Ala Ala Gly Pro Gly Gln Tyr Gly
                405                 410                 415
Pro Gly Gln Gln Gly Pro Ser Ala Ser Ala Ala Ala Ala Gly Gln
                420                 425                 430
Tyr Gly Ser Gly Pro Gly Gln Tyr Gly Pro Tyr Gly Pro Gly Gln Ser
                435                 440                 445
Gly Pro Gly Ser Gly Gln Gln Gly Gln Gly Pro Tyr Gly Pro Gly Ala
                450                 455                 460
Ser Ala Ala Ala Ala Gly Gln Tyr Gly Pro Gly Gln Gln Gly Pro
465                 470                 475                 480
Tyr Gly Pro Gly Gln Ser Ala Ala Ala Ala Gly Pro Gly Ser Gly
                485                 490                 495
Gln Tyr Gly Pro Gly Ala Ser Gly Gln Asn Gly Pro Gly Ser Gly Gln
                500                 505                 510
Tyr Gly Pro Gly Gln Gln Gly Pro Gln Ser Ala Ala Ala Ala
                515                 520                 525
Gly Gln Tyr Gln Gln Gly Pro Gly Gln Gly Pro Tyr Gly Pro Gly
            530                 535                 540
Ala Ser Ala Ala Ala Ala Gly Gln Tyr Ser Gly Pro Gly Gln
545                 550                 555                 560
Gln Gly Pro Tyr Gly Pro Gly Gln Ser Gly Ser Gly Gln Gln Gly Pro
                565                 570                 575
Gly Gln Gln Gly Pro Tyr Ala Ser Ala Ala Ala Ala Gly Pro Gly
            580                 585                 590
Ser Gly Gln Gln Gly Pro Gly Ala Ser
            595                 600
```

<210> SEQ ID NO 10
<211> LENGTH: 565
<212> TYPE: PRT
<213> ORGANISM: Artificial Sequence
<220> FEATURE:
<223> OTHER INFORMATION: Met-PRT468

<400> SEQUENCE: 10

```
Met Gly Pro Gly Gln Gln Gly Pro Tyr Gly Pro Gly Ala Ser Ala Ala
1               5                   10                  15
Ala Ala Ala Ala Gly Ser Asn Gly Pro Ser Gly Gln Gln Gly
            20                  25                  30
Pro Gly Gln Ser Gly Gln Tyr Gly Pro Gly Gln Gln Gly Pro Gly Gln
            35                  40                  45
Gln Gly Pro Gly Ser Ser Ala Ala Ala Ala Ala Gly Pro Gly
        50                  55                  60
Gln Tyr Gly Pro Gly Gln Gln Gly Pro Ser Ala Ser Ala Ala Ala Ala
65                  70                  75                  80
Ala Ala Ala Gly Pro Gly Ser Gly Gln Gln Gly Pro Gly Ala Ser Gly
```

```
                           85                  90                  95
Gln Tyr Gly Pro Gly Gln Gln Gly Pro Gly Gln Gln Gly Pro Gly Ser
                  100                 105                 110
Ser Ala Ala Ala Ala Ala Ala Gly Ser Tyr Gly Ser Gly Pro Gly
            115                 120                 125
Gln Gln Gly Pro Tyr Gly Ser Ala Ala Ala Ala Ala Ala Gly Pro
        130                 135                 140
Gly Ser Gly Gln Tyr Gln Gly Pro Tyr Gly Pro Gly Ala Ser Gly
145                 150                 155                 160
Pro Gly Gln Tyr Gly Pro Gly Gln Gln Gly Pro Ser Ala Ser Ala Ala
                165                 170                 175
Ala Ala Ala Ala Ala Gly Ser Gly Gln Gln Gly Pro Gly Gln Tyr Gly
            180                 185                 190
Pro Tyr Ala Ser Ala Ala Ala Ala Ala Ala Gly Ser Tyr Gly Ser
        195                 200                 205
Gly Pro Gly Gln Gln Pro Tyr Gly Pro Gly Gln Ser Gly Ser Gly
    210                 215                 220
Gln Gln Gly Pro Gly Gln Gln Gly Pro Tyr Ala Ser Ala Ala Ala Ala
225                 230                 235                 240
Ala Ala Ala Gly Pro Gly Gln Gln Pro Tyr Gly Pro Gly Ser Ser
            245                 250                 255
Ala Ala Ala Ala Ala Ala Gly Ser Tyr Gly Tyr Gly Pro Gly Gln
        260                 265                 270
Gln Gly Pro Tyr Gly Pro Gly Ala Ser Gly Gln Asn Gly Pro Gly Ser
                275                 280                 285
Gly Gln Tyr Gly Pro Gly Gln Gln Pro Gly Pro Ser Ala Ala Ala
            290                 295                 300
Ala Ala Ala Gly Pro Gly Gln Gln Gly Pro Tyr Gly Pro Gly Ala
        305                 310                 315                 320
Ser Ala Ala Ala Ala Ala Ala Gly Ser Tyr Gly Pro Gly Gln Gln
                325                 330                 335
Gly Pro Gly Gln Tyr Gly Pro Gly Ser Ser Gly Pro Gly Gln Gln Gly
            340                 345                 350
Pro Tyr Gly Pro Gly Ser Ser Ala Ala Ala Ala Ala Ala Gly Ser
        355                 360                 365
Tyr Gly Pro Gly Gln Gln Gly Pro Tyr Gly Pro Gly Pro Ser Ala Ala
    370                 375                 380
Ala Ala Ala Ala Ala Gly Ser Tyr Gln Gln Gly Pro Gly Gln Gln Gly
385                 390                 395                 400
Pro Tyr Gly Pro Gly Ala Ser Gly Pro Gly Gln Gln Gly Pro Tyr Gly
                405                 410                 415
Pro Gly Ala Ser Ala Ala Ala Ala Ala Gly Pro Gly Gln Tyr
            420                 425                 430
Gly Pro Gly Gln Gln Gly Pro Ser Ala Ser Ala Ala Ala Ala Ala
        435                 440                 445
Ala Gly Ser Tyr Gly Ser Gly Pro Gly Gln Tyr Gly Pro Tyr Gly Pro
    450                 455                 460
Gly Gln Ser Gly Pro Gly Ser Gly Gln Gln Gly Gln Gly Pro Tyr Gly
465                 470                 475                 480
Pro Gly Ala Ser Ala Ala Ala Ala Ala Ala Gly Ser Tyr Gly Pro
            485                 490                 495
Gly Gln Gln Gly Pro Tyr Gly Pro Gly Pro Ser Ala Ala Ala Ala Ala
                500                 505                 510
```

```
Ala Ala Gly Pro Gly Ser Gly Gln Tyr Gly Pro Gly Ala Ser Gly Gln
        515                 520                 525

Asn Gly Pro Gly Ser Gly Gln Tyr Gly Pro Gly Gln Gln Gly Pro Gly
        530                 535                 540

Pro Ser Ala Ala Ala Ala Ala Ala Gly Pro Gly Ser Gly Gln Gln
545                 550                 555                 560

Gly Pro Gly Ala Ser
                565

<210> SEQ ID NO 11
<211> LENGTH: 576
<212> TYPE: PRT
<213> ORGANISM: Artificial Sequence
<220> FEATURE:
<223> OTHER INFORMATION: PRT468

<400> SEQUENCE: 11

Met His His His His His Ser Ser Gly Ser Gly Pro Gly Gln
1               5                   10                  15

Gln Gly Pro Tyr Gly Pro Gly Ala Ser Ala Ala Ala Ala Ala Ala
                20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Ala Gly Pro Gly Gln Tyr Gly Pro Gly
65                  70                  75                  80

Gln Gln Gly Pro Ser Ala Ser Ala Ala Ala Ala Ala Ala Ala Gly Pro
                85                  90                  95

Gly Ser Gly Gln Gln Gly Pro Gly Ala Ser Gly Gln Tyr Gly Pro Gly
                100                 105                 110

Gln Gln Gly Pro Gly Gln Gln Gly Pro Gly Ser Ser Ala Ala Ala Ala
            115                 120                 125

Ala Ala Ala Gly Ser Tyr Gly Ser Gly Pro Gly Gln Gln Gly Pro Tyr
        130                 135                 140

Gly Ser Ala Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Gln Gln Gly Pro Ser Ala Ser Ala Ala Ala Ala Ala Ala Ala
            180                 185                 190

Gly Ser Gly Gln Gln Gly Pro Gly Gln Tyr Gly Pro Tyr Ala Ser Ala
        195                 200                 205

Ala Ala Ala Ala Ala Gly Ser Tyr Gly Ser Gly Pro Gly Gln Gln
        210                 215                 220

Gly Pro Tyr Gly Pro Gly Gln Ser Gly Ser Gly Gln Gln Gly Pro Gly
225                 230                 235                 240

Gln Gln Gly Pro Tyr Ala Ser Ala Ala Ala Ala Ala Ala Gly Pro
                245                 250                 255

Gly Gln Gln Gly Pro Tyr Gly Pro Gly Ser Ser Ala Ala Ala Ala
                260                 265                 270

Ala Ala Gly Ser Tyr Gly Tyr Gly Pro Gly Gln Gln Gly Pro Tyr Gly
            275                 280                 285

Pro Gly Ala Ser Gly Gln Asn Gly Pro Gly Ser Gly Gln Tyr Gly Pro
        290                 295                 300
```

```
Gly Gln Gln Gly Pro Gly Pro Ser Ala Ala Ala Ala Ala Ala Gly
305                 310                 315                 320

Pro Gly Gln Gln Gly Pro Tyr Gly Pro Gly Ala Ser Ala Ala Ala
                325                 330                 335

Ala Ala Ala Gly Ser Tyr Gly Pro Gly Gln Gln Gly Pro Gly Gln Tyr
        340                 345                 350

Gly Pro Gly Ser Ser Gly Pro Gly Gln Gln Gly Pro Tyr Gly Pro Gly
            355                 360                 365

Ser Ser Ala Ala Ala Ala Ala Ala Gly Ser Tyr Gly Pro Gly Gln
370                 375                 380

Gln Gly Pro Tyr Gly Pro Gly Pro Ser Ala Ala Ala Ala Ala Ala
385                 390                 395                 400

Gly Ser Tyr Gln Gln Gly Pro Gly Gln Gln Gly Pro Tyr Gly Pro Gly
                405                 410                 415

Ala Ser Gly Pro Gly Gln Gln Gly Pro Tyr Gly Pro Gly Ala Ser Ala
            420                 425                 430

Ala Ala Ala Ala Ala Gly Pro Gly Gln Tyr Gly Pro Gly Gln Gln
435                 440                 445

Gly Pro Ser Ala Ser Ala Ala Ala Ala Ala Gly Ser Tyr Gly
450                 455                 460

Ser Gly Pro Gly Gln Tyr Gly Pro Tyr Gly Pro Gly Gln Ser Gly Pro
465                 470                 475                 480

Gly Ser Gly Gln Gln Gly Gln Gly Pro Tyr Gly Pro Gly Ala Ser Ala
            485                 490                 495

Ala Ala Ala Ala Ala Gly Ser Tyr Gly Pro Gly Gln Gln Gly Pro
                500                 505                 510

Tyr Gly Pro Gly Pro Ser Ala Ala Ala Ala Ala Ala Gly Pro Gly
            515                 520                 525

Ser Gly Gln Tyr Gly Pro Gly Ala Ser Gly Gln Asn Gly Pro Gly Ser
530                 535                 540

Gly Gln Tyr Gly Pro Gly Gln Gln Gly Pro Gly Pro Ser Ala Ala Ala
545                 550                 555                 560

Ala Ala Ala Ala Gly Pro Gly Ser Gly Gln Gln Gly Pro Gly Ala Ser
                565                 570                 575

<210> SEQ ID NO 12
<211> LENGTH: 50
<212> TYPE: PRT
<213> ORGANISM: Araneus diadematus

<400> SEQUENCE: 12

Ser Gly Cys Asp Val Leu Val Gln Ala Leu Leu Glu Val Val Ser Ala
1               5                   10                  15

Leu Val Ser Ile Leu Gly Ser Ser Ile Gly Gln Ile Asn Tyr Gly
            20                  25                  30

Ala Ser Ala Gln Tyr Thr Gln Met Val Gly Gln Ser Val Ala Gln Ala
        35                  40                  45

Leu Ala
    50

<210> SEQ ID NO 13
<211> LENGTH: 30
<212> TYPE: PRT
<213> ORGANISM: Araneus diadematus

<400> SEQUENCE: 13
```

```
Ser Gly Cys Asp Val Leu Val Gln Ala Leu Leu Glu Val Val Ser Ala
1               5                   10                  15

Leu Val Ser Ile Leu Gly Ser Ser Ile Gly Gln Ile Asn
            20                  25                  30
```

<210> SEQ ID NO 14
<211> LENGTH: 21
<212> TYPE: PRT
<213> ORGANISM: Araneus diadematus

<400> SEQUENCE: 14

```
Ser Gly Cys Asp Val Leu Val Gln Ala Leu Leu Glu Val Val Ser Ala
1               5                   10                  15

Leu Val Ser Ile Leu
            20
```

<210> SEQ ID NO 15
<211> LENGTH: 1154
<212> TYPE: PRT
<213> ORGANISM: Artificial Sequence
<220> FEATURE:
<223> OTHER INFORMATION: recombinant spider silk protein
      ADF3KaiLargeNRSH1

<400> SEQUENCE: 15

```
Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
                100                 105                 110

Gly Gly Gln Gly Pro Tyr Gly Pro Gly Ser Ser Ala Ala Ala Ala Ala
                115                 120                 125

Ala Gly Gly Asn Gly Pro Gly Ser Gly Gln Gln Gly Ala Gly Gln Gln
                130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Pro Gly Gln Gln Gly
                165                 170                 175

Pro Gly Gly Gln Gly Pro Tyr Gly Pro Gly Ala Ser Ala Ala Ala Ala
                180                 185                 190

Ala Ala Gly Gly Tyr Gly Pro Gly Ser Gly Gln Gly Pro Gly Gln Gln
                195                 200                 205

Gly Pro Gly Gly Gln Gly Pro Tyr Gly Pro Gly Ala Ser Ala Ala Ala
                210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
                245                 250                 255
```

```
Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gln Gly Pro
            275                 280                 285

Tyr Gly Pro Gly Ala Ser Ala Ser Ala Ala Ser Gly Gly Tyr Gly
            290                 295                 300

Pro Gly Ser Gln Gln Gly Pro Gly Gln Gln Gly Pro Gly Gly Gln
305                 310                 315                 320

Gly Pro Tyr Gly Pro Gly Ala Ser Ala Ala Ala Ala Ala Gly Gly
            325                 330                 335

Tyr Gly Pro Gly Ser Gly Gln Gln Gly Pro Gly Gln Gln Gly Pro
            340                 345                 350

Gln Gln Gly Pro Gly Gln Gln Gly Pro Gly Gln Gln Gly Tyr Gly
            355                 360                 365

Pro Gly Ala Ser Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
            405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Ala Gly Ala Ala Gly
            435                 440                 445

Gly Tyr Gly Pro Gly Ser Gly Gln Gln Gly Pro Gly Gln Gln Gly Pro
            450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
            485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
            515                 520                 525

Gly Gly Gln Gly Pro Tyr Gly Pro Gly Ala Ala Ser Ala Ala Val Ser
            530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
            565                 570                 575

Ala Ser Ala Ala Ala Ala Ala Gly Gly Tyr Gly Pro Gly Ser Gly
            580                 585                 590

Gln Gln Gly Pro Ser Gln Gln Gly Pro Gly Gln Gln Gly Pro Gly Gly
            595                 600                 605

Gln Gly Pro Tyr Gly Pro Gly Ala Ser Ala Ala Ala Ala Ala Gly
            610                 615                 620

Gly Tyr Gly Pro Gly Ser Gly Gln Gln Gly Pro Gly Gly Gln Gly Pro
625                 630                 635                 640

Tyr Gly Pro Gly Ser Ser Ala Ala Ala Ala Ala Gly Gly Asn Gly
            645                 650                 655

Pro Gly Ser Gly Gln Gln Gly Ala Gly Gln Gln Gly Pro Gly Gln Gln
            660                 665                 670
```

Gly Pro Gly Ala Ser Ala Ala Ala Ala Gly Gly Tyr Gly Pro
            675                 680                 685

Gly Ser Gly Gln Gln Gly Pro Gly Gln Gln Gly Pro Gly Gln Gly
        690                 695                 700

Pro Tyr Gly Pro Gly Ala Ser Ala Ala Ala Ala Ala Gly Gly Tyr
705                 710                 715                 720

Gly Pro Gly Ser Gly Gln Gly Pro Gln Gln Gly Pro Gly Gly Gln
                725                 730                 735

Gly Pro Tyr Gly Pro Gly Ala Ser Ala Ala Ala Ala Ala Gly Gly
            740                 745                 750

Tyr Gly Pro Gly Ser Gly Gln Gln Gly Pro Gly Gln Gln Gly Pro Gly
        755                 760                 765

Gln Gln Gly Pro Gly Gln Gln Gly Pro Tyr Gly Pro Gly Ala Ser Ala
    770                 775                 780

Ala Ala Ala Ala Gly Gly Tyr Gly Pro Gly Tyr Gly Gln Gln Gly
785                 790                 795                 800

Pro Gly Gln Gln Gly Pro Gly Gln Gln Gly Pro Tyr Gly Pro Gly Ala
            805                 810                 815

Ser Ala Ala Ser Ala Ala Ser Gly Gly Tyr Gly Pro Gly Ser Gly Gln
            820                 825                 830

Gln Gly Pro Gly Gln Gln Gly Pro Gly Gly Gln Gly Pro Tyr Gly Pro
    835                 840                 845

Gly Ala Ser Ala Ala Ala Ala Ala Gly Gly Tyr Gly Pro Gly Ser
    850                 855                 860

Gly Gln Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
            885                 890                 895

Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
    915                 920                 925

Gly Gln Gln Gly Pro Gly Gln Gln Gly Pro Gly Gln Gln Gly Pro Gly
    930                 935                 940

Gln Gln Gly Pro Gly Gln Gln Gly Pro Gly Gln Gly Ala Tyr Gly
945                 950                 955                 960

Pro Gly Ala Ser Ala Ala Ala Gly Ala Ala Gly Gly Tyr Gly Pro Gly
            965                 970                 975

Ser Gly Gln Gln Gly Pro Gly Gln Gln Gly Pro Gly Gln Gln Gly Pro
            980                 985                 990

Gly Gln Gln Gly Pro Gly Gln Gln Gly Pro Gly Gln Gln Gly Pro Gly
            995                 1000                1005

Gln Gln Gly Pro Gly Gln Gln Gly Pro Tyr Gly Pro Gly Ala Ser
    1010                1015                1020

Ala Ala Ala Ala Ala Ala Gly Gly Tyr Gly Pro Gly Ser Gly Gln
1025                1030                1035

Gln Gly Pro Gly Gln Gln Gly Pro Gly Gln Gln Gly Pro Gly Gly
    1040                1045                1050

Gln Gly Pro Tyr Gly Pro Gly Ala Ala Ser Ala Ala Val Ser Val
    1055                1060                1065

Gly Gly Tyr Gly Pro Gln Ser Ser Ser Val Pro Val Ala Ser Ala
    1070                1075                1080

Val Ala Ser Arg Leu Ser Ser Pro Ala Ala Ser Ser Arg Val Ser

```
                    1085                1090                1095

Ser Ala Val Ser Ser Leu Val Ser Ser Gly Pro Thr Lys His Ala
        1100                1105                1110

Ala Leu Ser Asn Thr Ile Ser Ser Val Val Ser Gln Val Ser Ala
        1115                1120                1125

Ser Asn Pro Gly Leu Ser Gly Cys Asp Val Leu Val Gln Ala Leu
        1130                1135                1140

Leu Glu Val Val Ser Ala Leu Val Ser Ile Leu
        1145                1150

<210> SEQ ID NO 16
<211> LENGTH: 24
<212> TYPE: PRT
<213> ORGANISM: Artificial Sequence
<220> FEATURE:
<223> OTHER INFORMATION: His tag and start codon

<400> SEQUENCE: 16

Met His His His His His His His His His Ser Ser Gly Ser Ser
1               5                   10                  15

Leu Glu Val Leu Phe Gln Gly Pro
            20

<210> SEQ ID NO 17
<211> LENGTH: 2364
<212> TYPE: PRT
<213> ORGANISM: Artificial Sequence
<220> FEATURE:
<223> OTHER INFORMATION: Met-PRT799

<400> SEQUENCE: 17

Met Gly Pro Gly Gln Gln Gly Pro Tyr Gly Pro Gly Ala Ser Ala
1               5                   10                  15

Ala Ala Ala Gly Gln Asn Gly Pro Gly Ser Gly Gln Gln Gly Pro
            20                  25                  30

Gly Ser Gly Gln Tyr Gly Pro Gly Gln Gly Pro Gly Gln Gln Gly
        35                  40                  45

Pro Gly Ser Ser Ala Ala Ala Ala Gly Pro Gly Gln Tyr Gly Pro
    50                  55                  60

Gly Gln Gln Gly Pro Ser Ala Ser Ala Ala Ala Ala Gly Pro Gly
65                  70                  75                  80

Ser Gly Gln Gln Gly Pro Gly Ala Ser Gly Gln Tyr Gly Pro Gly Gln
        85                  90                  95

Gln Gly Pro Gly Gln Gly Pro Gly Ser Ser Ala Ala Ala Ala
            100                 105                 110

Gly Gln Tyr Gly Ser Gly Pro Gly Gln Gln Gly Pro Tyr Gly Ser Ala
        115                 120                 125

Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Gly Ser Gly Gln Gln Gly Pro
            165                 170                 175

Gly Gln Tyr Gly Pro Tyr Ala Ser Ala Ala Ala Ala Gly Gln Tyr
        180                 185                 190

Gly Ser Gly Pro Gly Gln Gln Gly Pro Tyr Gly Pro Gly Gln Ser Gly
        195                 200                 205
```

```
Ser Gly Gln Gly Pro Gly Gln Gln Gly Pro Tyr Ala Ser Ala Ala
    210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
            245                 250                 255

Pro Tyr Gly Pro Gly Ala Ser Gly Gln Asn Gly Pro Gly Ser Gly Gln
                260                 265                 270

Tyr Gly Pro Gly Gln Gly Pro Gln Ser Ala Ala Ala Ala
        275                 280                 285

Gly Pro Gly Gln Gln Gly Pro Tyr Gly Pro Gly Ala Ser Ala Ala Ala
    290                 295                 300

Ala Ala Gly Gln Tyr Gly Pro Gly Gln Gly Pro Gly Gln Tyr Gly
305                 310                 315                 320

Pro Gly Ser Ser Gly Pro Gln Gly Pro Tyr Gly Pro Gly Ser
                325                 330                 335

Ser Ala Ala Ala Ala Gly Gln Tyr Gly Pro Gly Gln Gln Gly Pro
        340                 345                 350

Tyr Gly Pro Gly Gln Ser Ala Ala Ala Ala Gly Gln Tyr Gln Gln
        355                 360                 365

Gly Pro Gly Gln Gln Gly Pro Tyr Gly Pro Gly Ala Ser Gly Pro Gly
    370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gly Pro Ser Ala Ser Ala Ala
            405                 410                 415

Ala Ala Ala Gly Gln Tyr Gly Ser Gly Pro Gln Tyr Gly Pro Tyr
            420                 425                 430

Gly Pro Gly Gln Ser Gly Pro Gly Ser Gly Gln Gln Gly Gln Gly Pro
        435                 440                 445

Tyr Gly Pro Gly Ala Ser Ala Ala Ala Ala Gly Gln Tyr Gly Pro
    450                 455                 460

Gly Gln Gln Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
            485                 490                 495

Pro Gly Ser Gly Gln Tyr Gly Pro Gly Gln Gln Gly Pro Gly Gln Ser
                500                 505                 510

Ala Ala Ala Ala Ala Gly Gln Tyr Gln Gln Gly Pro Gly Gln Gln Gly
            515                 520                 525

Pro Tyr Gly Pro Gly Ala Ser Ala Ala Ala Ala Gly Gln Tyr Gly
    530                 535                 540

Ser Gly Pro Gly Gln Gln Gly Pro Tyr Gly Pro Gln Ser Gly Ser
545                 550                 555                 560

Gly Gln Gln Gly Pro Gln Gln Gly Pro Tyr Ala Ser Ala Ala
            565                 570                 575

Ala Ala Gly Pro Gly Ser Gly Gln Gln Gly Pro Gly Ala Ser Gly Gln
            580                 585                 590

Gln Gly Pro Tyr Gly Pro Gly Ala Ser Ala Ala Ala Ala Gly Gln
        595                 600                 605

Asn Gly Pro Gly Ser Gly Gln Gln Gly Pro Gly Gln Ser Gly Gln Tyr
        610                 615                 620

Gly Pro Gly Gln Gln Gly Pro Gly Gln Gln Gly Pro Gly Ser Ser Ala
```

-continued

```
            625                 630                 635                 640
        Ala Ala Ala Ala Gly Pro Gly Gln Tyr Gly Pro Gly Gln Gln Gly Pro
                            645                 650                 655

Ser Ala Ser Ala Ala Ala Ala Gly Pro Gly Ser Gly Gln Gln Gly
                        660                 665                 670

Pro Gly Ala Ser Gly Gln Tyr Gly Pro Gly Gln Gln Gly Pro Gly Gln
                    675                 680                 685

Gln Gly Pro Gly Ser Ser Ala Ala Ala Ala Gly Gln Tyr Gly Ser
        690                 695                 700

Gly Pro Gly Gln Gln Gly Pro Tyr Gly Ser Ala Ala Ala Ala Gly
        705                 710                 715                 720

Pro Gly Ser Gly Gln Tyr Gly Gln Gly Pro Tyr Gly Pro Gly Ala Ser
                        725                 730                 735

Gly Pro Gly Gln Tyr Gly Pro Gly Gln Gln Gly Pro Ser Ala Ser Ala
                        740                 745                 750

Ala Ala Ala Ala Gly Ser Gly Gln Gln Gly Pro Gly Gln Tyr Gly Pro
                    755                 760                 765

Tyr Ala Ser Ala Ala Ala Ala Gly Gln Tyr Gly Ser Gly Pro Gly
        770                 775                 780

Gln Gln Gly Pro Tyr Gly Pro Gly Ser Gly Ser Gly Gln Gln Gly
        785                 790                 795                 800

Pro Gly Gln Gln Gly Pro Tyr Ala Ser Ala Ala Ala Ala Gly Pro
                    805                 810                 815

Gly Gln Gln Gly Pro Tyr Gly Pro Gly Ser Ser Ala Ala Ala Ala
                    820                 825                 830

Gly Gln Tyr Gly Tyr Gly Pro Gly Gln Gln Gly Pro Tyr Gly Pro Gly
                    835                 840                 845

Ala Ser Gly Gln Asn Gly Pro Gly Ser Gly Gln Tyr Gly Pro Gly Gln
                850                 855                 860

Gln Gly Pro Gly Gln Ser Ala Ala Ala Ala Gly Pro Gly Gln Gln
        865                 870                 875                 880

Gly Pro Tyr Gly Pro Gly Ala Ser Ala Ala Ala Ala Gly Gln Tyr
                    885                 890                 895

Gly Pro Gly Gln Gln Gly Pro Gly Gln Tyr Gly Pro Gly Ser Ser Gly
                    900                 905                 910

Pro Gly Gln Gln Gly Pro Tyr Gly Pro Gly Ser Ser Ala Ala Ala Ala
                    915                 920                 925

Ala Gly Gln Tyr Gly Pro Gly Gln Gln Gly Pro Tyr Gly Pro Gly Gln
                930                 935                 940

Ser Ala Ala Ala Ala Gly Gln Tyr Gln Gln Gly Pro Gly Gln Gln
        945                 950                 955                 960

Gly Pro Tyr Gly Pro Gly Ala Ser Gly Pro Gly Gln Gln Gly Pro Tyr
                    965                 970                 975

Gly Pro Gly Ala Ser Ala Ala Ala Ala Gly Pro Gly Gln Tyr Gly
                980                 985                 990

Pro Gly Gln Gln Gly Pro Ser Ala  Ser Ala Ala Ala Ala  Ala Gly Gln
                    995                 1000                1005

Tyr Gly  Ser Gly Pro Gly Gln  Tyr Gly Pro Tyr Gly  Pro Gly Gln
            1010                1015                1020

Ser Gly  Pro Gly Ser Gly Gln  Gly Gln Gly Pro  Tyr Gly Pro
            1025                1030                1035

Gly Ala  Ser Ala Ala Ala Ala  Ala Gly Gln Tyr Gly  Pro Gly Gln
            1040                1045                1050
```

Gln Gly Pro Tyr Gly Pro Gly Gln Ser Ala Ala Ala Ala Ala Gly
     1055                1060                1065

Pro Gly Ser Gly Gln Tyr Gly Pro Gly Ala Ser Gly Gln Asn Gly
     1070                1075                1080

Pro Gly Ser Gly Gln Tyr Gly Pro Gly Gln Gln Gly Pro Gly Gln
     1085                1090                1095

Ser Ala Ala Ala Ala Gly Gln Tyr Gln Gln Gly Pro Gly Gln
     1100                1105                1110

Gln Gly Pro Tyr Gly Pro Gly Ala Ser Ala Ala Ala Ala Ala Gly
     1115                1120                1125

Gln Tyr Gly Ser Gly Pro Gly Gln Gln Gly Pro Tyr Gly Pro Gly
     1130                1135                1140

Gln Ser Gly Ser Gly Gln Gln Gly Pro Gly Gln Gln Gly Pro Tyr
     1145                1150                1155

Ala Ser Ala Ala Ala Ala Ala Gly Pro Gly Ser Gly Gln Gln Gly
     1160                1165                1170

Pro Gly Ala Ser Gly Gln Gln Gly Pro Tyr Gly Pro Gly Ala Ser
     1175                1180                1185

Ala Ala Ala Ala Ala Gly Gln Asn Gly Pro Gly Ser Gly Gln Gln
     1190                1195                1200

Gly Pro Gly Gln Ser Gly Gln Tyr Gly Pro Gly Gln Gln Gly Pro
     1205                1210                1215

Gly Gln Gln Gly Pro Gly Ser Ser Ala Ala Ala Ala Ala Gly Pro
     1220                1225                1230

Gly Gln Tyr Gly Pro Gly Gln Gln Gly Pro Ser Ala Ser Ala Ala
     1235                1240                1245

Ala Ala Ala Gly Pro Gly Ser Gly Gln Gln Gly Pro Gly Ala Ser
     1250                1255                1260

Gly Gln Tyr Gly Pro Gly Gln Gly Pro Gly Gln Gln Gly Pro
     1265                1270                1275

Gly Ser Ser Ala Ala Ala Ala Ala Gly Gln Tyr Gly Ser Gly Pro
     1280                1285                1290

Gly Gln Gln Gly Pro Tyr Gly Ser Ala Ala Ala Ala Ala Gly Pro
     1295                1300                1305

Gly Ser Gly Gln Tyr Gly Gln Pro Tyr Gly Pro Gly Ala Ser
     1310                1315                1320

Gly Pro Gly Gln Tyr Gly Pro Gly Gln Gln Gly Pro Ser Ala Ser
     1325                1330                1335

Ala Ala Ala Ala Ala Gly Ser Gly Gln Gln Gly Pro Gly Gln Tyr
     1340                1345                1350

Gly Pro Tyr Ala Ser Ala Ala Ala Ala Gly Gln Tyr Gly Ser
     1355                1360                1365

Gly Pro Gly Gln Gln Gly Pro Tyr Gly Pro Gly Gln Ser Gly Ser
     1370                1375                1380

Gly Gln Gln Gly Pro Gly Gln Gln Gly Pro Tyr Ala Ser Ala Ala
     1385                1390                1395

Ala Ala Ala Gly Pro Gly Gln Gln Gly Pro Tyr Gly Pro Gly Ser
     1400                1405                1410

Ser Ala Ala Ala Ala Gly Gln Tyr Gly Tyr Gly Pro Gly Gln
     1415                1420                1425

Gln Gly Pro Tyr Gly Pro Gly Ala Ser Gly Gln Asn Gly Pro Gly
     1430                1435                1440

```
Ser Gly Gln Tyr Gly Pro Gly Gln Gln Gly Gly Gln Ser Ala
1445                1450                1455

Ala Ala Ala Ala Gly Pro Gly Gln Gln Gly Pro Tyr Gly Pro Gly
1460                1465                1470

Ala Ser Ala Ala Ala Ala Ala Gly Gln Tyr Gly Pro Gly Gln Gln
1475                1480                1485

Gly Pro Gly Gln Tyr Gly Pro Gly Ser Ser Gly Pro Gly Gln Gln
1490                1495                1500

Gly Pro Tyr Gly Pro Gly Ser Ser Ala Ala Ala Ala Gly Gln
1505                1510                1515

Tyr Gly Pro Gly Gln Gln Gly Pro Tyr Gly Pro Gly Gln Ser Ala
1520                1525                1530

Ala Ala Ala Ala Gly Gln Tyr Gln Gln Gly Pro Gly Gln Gln Gly
1535                1540                1545

Pro Tyr Gly Pro Gly Ala Ser Gly Pro Gly Gln Gln Gly Pro Tyr
1550                1555                1560

Gly Pro Gly Ala Ser Ala Ala Ala Ala Gly Pro Gly Gln Tyr
1565                1570                1575

Gly Pro Gly Gln Gln Gly Pro Ser Ala Ser Ala Ala Ala Ala Ala
1580                1585                1590

Gly Gln Tyr Gly Ser Gly Pro Gly Gln Tyr Gly Pro Tyr Gly Pro
1595                1600                1605

Gly Gln Ser Gly Pro Gly Ser Gly Gln Gln Gly Gln Gly Pro Tyr
1610                1615                1620

Gly Pro Gly Ala Ser Ala Ala Ala Ala Ala Gly Gln Tyr Gly Pro
1625                1630                1635

Gly Gln Gln Gly Pro Tyr Gly Pro Gly Gln Ser Ala Ala Ala Ala
1640                1645                1650

Ala Gly Pro Gly Ser Gly Gln Tyr Gly Pro Gly Ala Ser Gly Gln
1655                1660                1665

Asn Gly Pro Gly Ser Gly Gln Tyr Gly Pro Gly Gln Gln Gly Pro
1670                1675                1680

Gly Gln Ser Ala Ala Ala Ala Gly Gln Tyr Gln Gln Gly Pro
1685                1690                1695

Gly Gln Gln Gly Pro Tyr Gly Pro Gly Ala Ser Ala Ala Ala Ala
1700                1705                1710

Ala Gly Gln Tyr Gly Ser Gly Pro Gly Gln Gln Gly Pro Tyr Gly
1715                1720                1725

Pro Gly Gln Ser Gly Ser Gly Gln Gln Gly Pro Gly Gln Gln Gly
1730                1735                1740

Pro Tyr Ala Ser Ala Ala Ala Ala Gly Pro Gly Ser Gly Gln
1745                1750                1755

Gln Gly Pro Gly Ala Ser Gly Gln Gln Gly Pro Tyr Gly Pro Gly
1760                1765                1770

Ala Ser Ala Ala Ala Ala Ala Gly Gln Asn Gly Pro Gly Ser Gly
1775                1780                1785

Gln Gln Gly Pro Gly Gln Ser Gly Gln Tyr Gly Pro Gly Gln Gln
1790                1795                1800

Gly Pro Gly Gln Gln Gly Pro Gly Ser Ser Ala Ala Ala Ala Ala
1805                1810                1815

Gly Pro Gly Gln Tyr Gly Pro Gly Gln Gln Gly Pro Ser Ala Ser
1820                1825                1830

Ala Ala Ala Ala Ala Gly Pro Gly Ser Gly Gln Gln Gly Pro Gly
```

```
              1835                1840                1845

Ala Ser Gly Gln Tyr Gly Pro Gly Gln Gln Gly Gln Gln
    1850                1855                1860

Gly Pro Gly Ser Ser Ala Ala Ala Ala Gly Gln Tyr Gly Ser
    1865                1870                1875

Gly Pro Gly Gln Gln Gly Pro Tyr Gly Ser Ala Ala Ala Ala
    1880                1885                1890

Gly Pro Gly Ser Gly Gln Tyr Gly Gln Gly Pro Tyr Gly Pro Gly
    1895                1900                1905

Ala Ser Gly Pro Gly Gln Tyr Gly Pro Gly Gln Gln Gly Pro Ser
    1910                1915                1920

Ala Ser Ala Ala Ala Ala Ala Gly Ser Gly Gln Gln Gly Pro Gly
    1925                1930                1935

Gln Tyr Gly Pro Tyr Ala Ser Ala Ala Ala Ala Gly Gln Tyr
    1940                1945                1950

Gly Ser Gly Pro Gly Gln Gln Gly Pro Tyr Gly Pro Gly Gln Ser
    1955                1960                1965

Gly Ser Gly Gln Gln Gly Pro Gly Gln Gln Gly Pro Tyr Ala Ser
    1970                1975                1980

Ala Ala Ala Ala Ala Gly Pro Gly Gln Gln Gly Pro Tyr Gly Pro
    1985                1990                1995

Gly Ser Ser Ala Ala Ala Ala Gly Gln Tyr Gly Tyr Gly Pro
    2000                2005                2010

Gly Gln Gln Gly Pro Tyr Gly Pro Gly Ala Ser Gly Gln Asn Gly
    2015                2020                2025

Pro Gly Ser Gly Gln Tyr Gly Pro Gly Gln Gln Gly Pro Gly Gln
    2030                2035                2040

Ser Ala Ala Ala Ala Ala Gly Pro Gly Gln Gln Gly Pro Tyr Gly
    2045                2050                2055

Pro Gly Ala Ser Ala Ala Ala Ala Ala Gly Gln Tyr Gly Pro Gly
    2060                2065                2070

Gln Gln Gly Pro Gly Gln Tyr Gly Pro Gly Ser Ser Gly Pro Gly
    2075                2080                2085

Gln Gln Gly Pro Tyr Gly Pro Gly Ser Ser Ala Ala Ala Ala Ala
    2090                2095                2100

Gly Gln Tyr Gly Pro Gly Gln Gln Gly Pro Tyr Gly Pro Gly Gln
    2105                2110                2115

Ser Ala Ala Ala Ala Ala Gly Gln Tyr Gln Gln Gly Pro Gly Gln
    2120                2125                2130

Gln Gly Pro Tyr Gly Pro Gly Ala Ser Gly Pro Gly Gln Gln Gly
    2135                2140                2145

Pro Tyr Gly Pro Gly Ala Ser Ala Ala Ala Ala Gly Pro Gly
    2150                2155                2160

Gln Tyr Gly Pro Gly Gln Gln Gly Pro Ser Ala Ser Ala Ala Ala
    2165                2170                2175

Ala Ala Gly Gln Tyr Gly Ser Gly Pro Gly Gln Tyr Gly Pro Tyr
    2180                2185                2190

Gly Pro Gly Gln Ser Gly Pro Gly Ser Gly Gln Gln Gly Gln Gly
    2195                2200                2205

Pro Tyr Gly Pro Gly Ala Ser Ala Ala Ala Ala Ala Gly Gln Tyr
    2210                2215                2220

Gly Pro Gly Gln Gln Gly Pro Tyr Gly Pro Gly Gln Ser Ala Ala
    2225                2230                2235
```

-continued

Ala Ala  Ala Gly Pro Gly Ser  Gly Gln Tyr Gly Pro  Gly Ala Ser
    2240             2245                 2250

Gly Gln  Asn Gly Pro Gly Ser  Gly Gln Tyr Gly Pro  Gly Gln Gln
    2255             2260                 2265

Gly Pro  Gly Gln Ser Ala Ala  Ala Ala Ala Gly Gln  Tyr Gln Gln
    2270             2275                 2280

Gly Pro  Gly Gln Gln Gly Pro  Tyr Gly Pro Gly Ala  Ser Ala Ala
    2285             2290                 2295

Ala Ala  Ala Gly Gln Tyr Gly  Ser Gly Pro Gln Gln  Gly Pro
    2300             2305                 2310

Tyr Gly  Pro Gly Gln Ser Gly  Ser Gly Gln Gln Gly  Pro Gly Gln
    2315             2320                 2325

Gln Gly  Pro Tyr Ala Ser Ala  Ala Ala Ala Ala Gly  Pro Gly Ser
    2330             2335                 2340

Gly Gln  Gln Gly Ser Ser Val  Asp Lys Leu Ala Ala  Ala Leu Glu
    2345             2350                 2355

His His  His His His His
    2360

<210> SEQ ID NO 18
<211> LENGTH: 2375
<212> TYPE: PRT
<213> ORGANISM: Artificial Sequence
<220> FEATURE:
<223> OTHER INFORMATION: PRT799

<400> SEQUENCE: 18

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
                20                  25                  30

Asn Gly Pro Gly Ser Gly Gln Gln Gly Pro Gly Gln Ser Gly Gln Tyr
                35                  40                  45

Gly Pro Gly Gln Gln Gly Pro Gly Gln Gln Gly Pro Gly Ser Ser Ala
        50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
                100                 105                 110

Gln Gly Pro Gly Ser Ser Ala Ala Ala Ala Ala Gly Gln Tyr Gly Ser
        115                 120                 125

Gly Pro Gly Gln Gln Gly Pro Tyr Gly Ser Ala Ala Ala Ala Ala Gly
        130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Ala Gly Ser Gly Gln Gln Gly Pro Gly Gln Tyr Gly Pro
                180                 185                 190

Tyr Ala Ser Ala Ala Ala Ala Gly Gln Tyr Gly Ser Gly Pro Gly
            195                 200                 205

Gln Gln Gly Pro Tyr Gly Pro Gly Gln Ser Gly Ser Gly Gln Gln Gly
        210                 215                 220

```
Pro Gly Gln Gln Gly Pro Tyr Ala Ser Ala Ala Ala Gly Pro
225                 230                 235                 240

Gly Gln Gln Gly Pro Tyr Gly Pro Gly Ser Ala Ala Ala Ala
                245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
        275                 280                 285

Gln Gly Pro Gly Gln Ser Ala Ala Ala Ala Gly Pro Gly Gln Gln
    290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala
                340                 345                 350

Ala Gly Gln Tyr Gly Pro Gly Gln Gln Gly Pro Tyr Gly Pro Gly Gln
    355                 360                 365

Ser Ala Ala Ala Ala Gly Gln Tyr Gln Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
                405                 410                 415

Pro Gly Gln Gln Gly Pro Ser Ala Ser Ala Ala Ala Ala Gly Gln
                420                 425                 430

Tyr Gly Ser Gly Pro Gly Gln Tyr Gly Pro Tyr Gly Pro Gly Gln Ser
    435                 440                 445

Gly Pro Gly Ser Gly Gln Gln Gly Gln Gly Pro Tyr Gly Pro Gly Ala
    450                 455                 460

Ser Ala Ala Ala Ala Gly Gln Tyr Gly Pro Gln Gln Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala
    515                 520                 525

Gly Gln Tyr Gln Gln Gly Pro Gly Gln Gln Gly Pro Tyr Gly Pro Gly
    530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Gly Pro Gly
                580                 585                 590

Ser Gly Gln Gln Gly Pro Gly Ala Ser Gly Gln Gln Gly Pro Tyr Gly
            595                 600                 605

Pro Gly Ala Ser Ala Ala Ala Ala Gly Gln Asn Gly Pro Gly Ser
    610                 615                 620

Gly Gln Gln Gly Pro Gly Gln Ser Gly Gln Tyr Gly Pro Gly Gln Gln
625                 630                 635                 640
```

-continued

Gly Pro Gly Gln Gln Gly Pro Gly Ser Ser Ala Ala Ala Ala Gly
              645                 650                 655

Pro Gly Gln Tyr Gly Pro Gly Gln Gln Gly Pro Ser Ala Ser Ala Ala
          660                 665                 670

Ala Ala Ala Gly Pro Gly Ser Gly Gln Gln Gly Pro Gly Ala Ser Gly
          675                 680                 685

Gln Tyr Gly Pro Gly Gln Gln Gly Pro Gly Gln Gln Gly Pro Gly Ser
690                 695                 700

Ser Ala Ala Ala Ala Gly Gln Tyr Gly Ser Gly Pro Gly Gln Gln
705                 710                 715                 720

Gly Pro Tyr Gly Ser Ala Ala Ala Ala Gly Pro Gly Ser Gly Gln
              725                 730                 735

Tyr Gly Gln Gly Pro Tyr Gly Pro Gly Ala Ser Gly Pro Gly Gln Tyr
              740                 745                 750

Gly Pro Gly Gln Gln Gly Pro Ser Ala Ser Ala Ala Ala Ala Gly
              755                 760                 765

Ser Gly Gln Gln Gly Pro Gly Gln Tyr Gly Pro Tyr Ala Ser Ala Ala
770                 775                 780

Ala Ala Ala Gly Gln Tyr Gly Ser Gly Pro Gly Gln Gln Gly Pro Tyr
785                 790                 795                 800

Gly Pro Gly Gln Ser Gly Ser Gly Gln Gln Gly Pro Gly Gln Gln Gly
              805                 810                 815

Pro Tyr Ala Ser Ala Ala Ala Ala Gly Pro Gly Gln Gln Gly Pro
              820                 825                 830

Tyr Gly Pro Gly Ser Ser Ala Ala Ala Ala Gly Gln Tyr Gly Tyr
              835                 840                 845

Gly Pro Gly Gln Gln Gly Pro Tyr Gly Pro Gly Ala Ser Gly Gln Asn
850                 855                 860

Gly Pro Gly Ser Gly Gln Tyr Gly Pro Gly Gln Gln Gly Pro Gly Gln
865                 870                 875                 880

Ser Ala Ala Ala Ala Ala Gly Pro Gly Gln Gln Gly Pro Tyr Gly Pro
              885                 890                 895

Gly Ala Ser Ala Ala Ala Ala Gly Gln Tyr Gly Pro Gly Gln Gln
              900                 905                 910

Gly Pro Gly Gln Tyr Gly Pro Gly Ser Ser Gly Pro Gly Gln Gln Gly
              915                 920                 925

Pro Tyr Gly Pro Gly Ser Ser Ala Ala Ala Ala Gly Gln Tyr Gly
930                 935                 940

Pro Gly Gln Gln Gly Pro Tyr Gly Pro Gly Ser Ala Ala Ala Ala
945                 950                 955                 960

Ala Gly Gln Tyr Gln Gln Gly Pro Gly Gln Gln Gly Pro Tyr Gly Pro
              965                 970                 975

Gly Ala Ser Gly Pro Gly Gln Gln Gly Pro Tyr Gly Pro Gly Ala Ser
              980                 985                 990

Ala Ala Ala Ala Ala Gly Pro Gly Gln Tyr Gly Pro Gly Gln Gln Gly
              995                 1000                1005

Pro Ser Ala Ser Ala Ala Ala Ala Gly Gln Tyr Gly Ser Gly
       1010                1015                 1020

Pro Gly Gln Tyr Gly Pro Tyr Gly Pro Gly Gln Ser Gly Pro Gly
       1025                1030                 1035

Ser Gly Gln Gln Gly Gln Gly Pro Tyr Gly Pro Gly Ala Ser Ala
       1040                1045                 1050

Ala Ala Ala Ala Gly Gln Tyr Gly Pro Gly Gln Gln Gly Pro Tyr

-continued

```
          1055                1060                1065
Gly Pro Gly Gln Ser Ala Ala Ala Ala Gly Pro Gly Ser Gly
          1070                1075                1080
Gln Tyr Gly Pro Gly Ala Ser Gly Gln Asn Gly Pro Gly Ser Gly
          1085                1090                1095
Gln Tyr Gly Pro Gly Gln Gln Gly Pro Gly Gln Ser Ala Ala Ala
          1100                1105                1110
Ala Ala Gly Gln Tyr Gln Gln Gly Pro Gly Gln Gln Gly Pro Tyr
          1115                1120                1125
Gly Pro Gly Ala Ser Ala Ala Ala Ala Gly Gln Tyr Gly Ser
          1130                1135                1140
Gly Pro Gly Gln Gln Gly Pro Tyr Gly Pro Gly Gln Ser Gly Ser
          1145                1150                1155
Gly Gln Gln Gly Pro Gly Gln Gly Pro Tyr Ala Ser Ala Ala
          1160                1165                1170
Ala Ala Ala Gly Pro Gly Ser Gly Gln Gln Gly Pro Gly Ala Ser
          1175                1180                1185
Gly Gln Gln Gly Pro Tyr Gly Pro Gly Ala Ser Ala Ala Ala Ala
          1190                1195                1200
Ala Gly Gln Asn Gly Pro Gly Ser Gly Gln Gln Gly Pro Gly Gln
          1205                1210                1215
Ser Gly Gln Tyr Gly Pro Gly Gln Gln Gly Pro Gly Gln Gln Gly
          1220                1225                1230
Pro Gly Ser Ser Ala Ala Ala Ala Gly Pro Gly Gln Tyr Gly
          1235                1240                1245
Pro Gly Gln Gln Gly Pro Ser Ala Ser Ala Ala Ala Ala Ala Gly
          1250                1255                1260
Pro Gly Ser Gly Gln Gln Gly Pro Gly Ala Ser Gly Gln Tyr Gly
          1265                1270                1275
Pro Gly Gln Gln Gly Pro Gly Gln Gln Gly Pro Gly Ser Ser Ala
          1280                1285                1290
Ala Ala Ala Gly Gln Tyr Gly Ser Gly Pro Gly Gln Gln Gly
          1295                1300                1305
Pro Tyr Gly Ser Ala Ala Ala Ala Gly Pro Gly Ser Gly Gln
          1310                1315                1320
Tyr Gly Gln Gly Pro Tyr Gly Pro Gly Ala Ser Gly Pro Gly Gln
          1325                1330                1335
Tyr Gly Pro Gly Gln Gln Gly Pro Ser Ala Ser Ala Ala Ala Ala
          1340                1345                1350
Ala Gly Ser Gly Gln Gln Gly Pro Gly Gln Tyr Gly Pro Tyr Ala
          1355                1360                1365
Ser Ala Ala Ala Ala Gly Gln Tyr Gly Ser Gly Pro Gly Gln
          1370                1375                1380
Gln Gly Pro Tyr Gly Pro Gly Gln Ser Gly Ser Gly Gln Gln Gly
          1385                1390                1395
Pro Gly Gln Gln Gly Pro Tyr Ala Ser Ala Ala Ala Ala Ala Gly
          1400                1405                1410
Pro Gly Gln Gln Gly Pro Tyr Gly Pro Gly Ser Ser Ala Ala Ala
          1415                1420                1425
Ala Ala Gly Gln Tyr Gly Tyr Gly Pro Gly Gln Gln Gly Pro Tyr
          1430                1435                1440
Gly Pro Gly Ala Ser Gly Gln Asn Gly Pro Gly Ser Gly Gln Tyr
          1445                1450                1455
```

Gly Pro Gly Gln Gly Pro Gly Gln Ser Ala Ala Ala Ala
        1460                1465            1470

Gly Pro Gly Gln Gly Pro Tyr Gly Pro Gly Ala Ser Ala Ala
        1475                1480            1485

Ala Ala Ala Gly Gln Tyr Gly Pro Gly Gln Gln Gly Pro Gly Gln
        1490                1495            1500

Tyr Gly Pro Gly Ser Ser Gly Pro Gly Gln Gln Gly Pro Tyr Gly
        1505                1510            1515

Pro Gly Ser Ser Ala Ala Ala Ala Gly Gln Tyr Gly Pro Gly
        1520                1525            1530

Gln Gln Gly Pro Tyr Gly Pro Gly Gln Ser Ala Ala Ala Ala Ala
        1535                1540            1545

Gly Gln Tyr Gln Gly Pro Gly Gln Gln Gly Pro Tyr Gly Pro
        1550                1555            1560

Gly Ala Ser Gly Pro Gly Gln Gln Gly Pro Tyr Gly Pro Gly Ala
        1565                1570            1575

Ser Ala Ala Ala Ala Gly Pro Gly Gln Tyr Gly Pro Gly Gln
        1580                1585            1590

Gln Gly Pro Ser Ala Ser Ala Ala Ala Ala Gly Gln Tyr Gly
        1595                1600            1605

Ser Gly Pro Gly Gln Tyr Gly Pro Tyr Gly Pro Gly Gln Ser Gly
        1610                1615            1620

Pro Gly Ser Gly Gln Gln Gly Gln Gly Pro Tyr Gly Pro Gly Ala
        1625                1630            1635

Ser Ala Ala Ala Ala Gly Gln Tyr Gly Pro Gly Gln Gln Gly
        1640                1645            1650

Pro Tyr Gly Pro Gly Gln Ser Ala Ala Ala Ala Ala Gly Pro Gly
        1655                1660            1665

Ser Gly Gln Tyr Gly Pro Gly Ala Ser Gly Gln Asn Gly Pro Gly
        1670                1675            1680

Ser Gly Gln Tyr Gly Pro Gly Gln Gln Gly Pro Gly Gln Ser Ala
        1685                1690            1695

Ala Ala Ala Ala Gly Gln Tyr Gln Gln Gly Pro Gly Gln Gln Gly
        1700                1705            1710

Pro Tyr Gly Pro Gly Ala Ser Ala Ala Ala Ala Gly Gln Tyr
        1715                1720            1725

Gly Ser Gly Pro Gly Gln Gln Gly Pro Tyr Gly Pro Gly Gln Ser
        1730                1735            1740

Gly Ser Gly Gln Gln Gly Pro Gly Gln Gln Gly Pro Tyr Ala Ser
        1745                1750            1755

Ala Ala Ala Ala Ala Gly Pro Gly Ser Gly Gln Gln Gly Pro Gly
        1760                1765            1770

Ala Ser Gly Gln Gln Gly Pro Tyr Gly Pro Gly Ala Ser Ala Ala
        1775                1780            1785

Ala Ala Ala Gly Gln Asn Gly Pro Gly Ser Gly Gln Gln Gly Pro
        1790                1795            1800

Gly Gln Ser Gly Gln Tyr Gly Pro Gly Gln Gln Gly Pro Gly Gln
        1805                1810            1815

Gln Gly Pro Gly Ser Ser Ala Ala Ala Ala Gly Pro Gly Gln
        1820                1825            1830

Tyr Gly Pro Gly Gln Gln Gly Pro Ser Ala Ser Ala Ala Ala Ala
        1835                1840            1845

```
Ala Gly Pro Gly Ser Gly Gln  Gln Gly Pro Gly Ala  Ser Gly Gln
    1850                1855                 1860

Tyr Gly Pro Gly Gln Gln Gly  Pro Gly Gln Gln Gly  Pro Gly Ser
    1865                1870                 1875

Ser Ala Ala Ala Ala Ala Gly  Gln Tyr Gly Ser Gly  Pro Gly Gln
    1880                1885                 1890

Gln Gly Pro Tyr Gly Ser Ala  Ala Ala Ala Gly Pro  Gly Ser
    1895                1900                 1905

Gly Gln Tyr Gly Gln Gly Pro  Tyr Gly Pro Gly Ala  Ser Gly Pro
    1910                1915                 1920

Gly Gln Tyr Gly Pro Gly Gln  Gln Gly Pro Ser Ala  Ser Ala Ala
    1925                1930                 1935

Ala Ala Ala Gly Ser Gly Gln  Gln Gly Pro Gly Gln  Tyr Gly Pro
    1940                1945                 1950

Tyr Ala Ser Ala Ala Ala Ala  Ala Gly Gln Tyr Gly  Ser Gly Pro
    1955                1960                 1965

Gly Gln Gln Gly Pro Tyr Gly  Pro Gly Ser Gly Ser  Gly Gln
    1970                1975                 1980

Gln Gly Pro Gly Gln Gln Gly  Pro Tyr Ala Ser Ala  Ala Ala Ala
    1985                1990                 1995

Ala Gly Pro Gly Gln Gln Gly  Pro Tyr Gly Pro Gly  Ser Ser Ala
    2000                2005                 2010

Ala Ala Ala Gly Gln Tyr  Gly Tyr Gly Pro Gly  Gln Gln Gly
    2015                2020                 2025

Pro Tyr Gly Pro Gly Ala Ser  Gly Gln Asn Gly Pro  Gly Ser Gly
    2030                2035                 2040

Gln Tyr Gly Pro Gly Gln Gln  Gly Pro Gly Gln Ser  Ala Ala Ala
    2045                2050                 2055

Ala Ala Gly Pro Gly Gln Gln  Gly Pro Tyr Gly Pro  Gly Ala Ser
    2060                2065                 2070

Ala Ala Ala Ala Gly Gln  Tyr Gly Pro Gly Gln  Gln Gly Pro
    2075                2080                 2085

Gly Gln Tyr Gly Pro Gly Ser  Ser Gly Pro Gly Gln  Gln Gly Pro
    2090                2095                 2100

Tyr Gly Pro Gly Ser Ser Ala  Ala Ala Ala Gly Gln  Tyr Gly
    2105                2110                 2115

Pro Gly Gln Gln Gly Pro Tyr  Gly Pro Gly Gln Ser  Ala Ala Ala
    2120                2125                 2130

Ala Ala Gly Gln Tyr Gln Gln  Gly Pro Gly Gln Gln  Gly Pro Tyr
    2135                2140                 2145

Gly Pro Gly Ala Ser Gly Pro  Gly Gln Gln Gly Pro  Tyr Gly Pro
    2150                2155                 2160

Gly Ala Ser Ala Ala Ala Ala  Ala Gly Pro Gly Gln  Tyr Gly Pro
    2165                2170                 2175

Gly Gln Gln Gly Pro Ser Ala  Ser Ala Ala Ala Ala  Ala Gly Gln
    2180                2185                 2190

Tyr Gly Ser Gly Pro Gly Gln  Tyr Gly Pro Tyr Gly  Pro Gly Gln
    2195                2200                 2205

Ser Gly Pro Gly Ser Gly Gln  Gln Gly Gln Gly Pro  Tyr Gly Pro
    2210                2215                 2220

Gly Ala Ser Ala Ala Ala Ala  Ala Gly Gln Tyr Gly  Pro Gly Gln
    2225                2230                 2235

Gln Gly Pro Tyr Gly Pro Gly  Gln Ser Ala Ala Ala  Ala Ala Gly
```

```
                2240                2245                2250
Pro Gly Ser Gly Gln Tyr Gly Pro Gly Ala Ser Gly Gln Asn Gly
    2255                2260                2265
Pro Gly Ser Gly Gln Tyr Gly Pro Gly Gln Gln Gly Pro Gly Gln
    2270                2275                2280
Ser Ala Ala Ala Ala Ala Gly Gln Tyr Gln Gln Gly Pro Gly Gln
    2285                2290                2295
Gln Gly Pro Tyr Gly Pro Gly Ala Ser Ala Ala Ala Ala Ala Gly
    2300                2305                2310
Gln Tyr Gly Ser Gly Pro Gly Gln Gln Gly Pro Tyr Gly Pro Gly
    2315                2320                2325
Gln Ser Gly Ser Gly Gln Gln Gly Pro Gly Gln Gln Gly Pro Tyr
    2330                2335                2340
Ala Ser Ala Ala Ala Ala Ala Gly Pro Gly Ser Gly Gln Gln Gly
    2345                2350                2355
Ser Ser Val Asp Lys Leu Ala Ala Ala Leu Glu His His His His
    2360                2365                2370
His His
    2375

<210> SEQ ID NO 19
<211> LENGTH: 4
<212> TYPE: PRT
<213> ORGANISM: Artificial Sequence
<220> FEATURE:
<223> OTHER INFORMATION: An motif

<400> SEQUENCE: 19

Ala Ala Ala Ala
1
```

HIGHLY CONTRACTED SYNTHETIC FIBROIN FIBER, PRODUCTION METHOD THEREFOR, AND METHOD FOR CONTRACTING SYNTHETIC FIBROIN FIBER

SEQUENCE LISTING SUBMISSION VIA EFS-WEB

A computer readable text file, entitled "SequenceListing.txt" created on or about Jul. 19, 2022 with a file size of about 103,000 bytes contains the sequence listing for this application and is hereby incorporated by reference in its entirety.

TECHNICAL FIELD

The present invention relates to a highly contracted artificial fibroin fiber, a production method therefor, and a method for contracting an artificial fibroin fiber.

BACKGROUND ART

Generally, fibers used for clothing, bedding, and the like are required to have a high level of tactile properties. As a fiber sufficiently satisfying tactile properties and having high-end properties, a silk which is a kind of natural fibroin fiber is known.

In addition, softness, heat retention properties, and the like are also required for fibers used for clothing, bedding, and the like. Accordingly, for example, silk used for clothing, bedding, and the like may be silk which has been subjected to a contraction process to increase bulkiness, whereby flexibility and heat retention properties are imparted.

Meanwhile, synthetic fibers such as polyester fibers, polyamide fibers, and acrylic fibers are generally used for clothing, bedding, and the like, and these synthetic fibers have a contraction percentage of 40% or more when being brought into contact with boiling water (Patent Literature 1).

CITATION LIST

Patent Literature

[Patent Literature 1] Japanese Unexamined Patent Publication No. 2009-121003

SUMMARY OF INVENTION

Problems to be Solved by the Invention

However, silk has only a few contraction percentage when being brought into contact with only water.

In addition, a contraction method disclosed in Patent Literature 1 involves a great danger because of handling high-temperature boiling water.

An object of the present invention is to provide a highly contracted artificial fibroin fiber which has a sufficiently high contraction percentage, has excellent tactile properties and flexibility, and can be safely produced; and a production method therefor. Another object of the present invention is to provide a method for contracting an artificial fibroin fiber, which is capable of safely obtaining at a sufficiently high contraction percentage.

Means for Solving the Problems

The present invention relates to, for example, each of the following inventions.

[1]
A contracted artificial fibroin fiber including:
a modified fibroin,
in which a contraction percentage defined by the following equation exceeds 7%.

$$\text{Contraction percentage} = \{1-(\text{length of contracted artificial fibroin fiber/length of artificial fibroin fiber before being brought into contact with water after spinning})\} \times 100(\%)$$

[2]
The highly contracted artificial fibroin fiber according to [1], in which the modified fibroin is a modified spider silk fibroin.

[3]
The highly contracted artificial fibroin fiber according to [1] or [2], which is contracted by being brought into contact with water below a boiling point.

[4]
The highly contracted artificial fibroin fiber according to [3], in which a temperature of the water is 10° C. to 90° C.

[5]
The highly contracted artificial fibroin fiber according to [3] or [4], which is further contracted by drying after being brought into contact with the water.

[6]
A method for producing a highly contracted artificial fibroin fiber, including:
a step of contracting an artificial fibroin fiber containing a modified fibroin by bringing the artificial fibroin fiber into contact with water below a boiling point,
in which a contraction percentage defined by the following equation exceeds 7%.

$$\text{Contraction percentage} = \{1-(\text{length of contracted artificial fibroin fiber/length of artificial fibroin fiber before being brought into contact with water after spinning})\} \times 100(\%)$$

[7]
The method for producing a highly contracted artificial fibroin fiber according to [6], in which the modified fibroin is a modified spider silk fibroin.

[8]
The method for producing a highly contracted artificial fibroin fiber according to [6] or [7], in which a temperature of the water is 10° C. to 90° C.

[9]
The method for producing a highly contracted artificial fibroin fiber according to any one of [6] to [8], in which the step of contracting the artificial fibroin fiber further includes drying the artificial fibroin fiber after being brought into contact with the water.

[10]
A method for contracting an artificial fibroin fiber, including: a step of contracting an artificial fibroin fiber containing a modified fibroin by bringing the artificial fibroin fiber into contact with water below a boiling point,
in which a contraction percentage defined by the following equation exceeds 7%.

$$\text{Contraction percentage} = \{1-(\text{length of contracted artificial fibroin fiber/length of artificial fibroin fiber before being brought into contact with water after spinning})\} \times 100(\%)$$

[11]

The method for contracting an artificial fibroin fiber according to [10], in which the modified fibroin is a modified spider silk fibroin.

[12]

The method for contracting an artificial fibroin fiber according to [10] or [11], in which a temperature of the water is 10° C. to 90° C.

[13]

The method for contracting an artificial fibroin fiber according to any one of [10] to [12], in which the step of contracting the artificial fibroin fiber further includes drying the artificial fibroin fiber after being brought into contact with the water.

Effects of the Invention

According to the present invention, it is possible to provide a highly contracted artificial fibroin fiber which has a sufficiently high contraction percentage, has excellent tactile properties and flexibility, and can be safely produced; and a production method therefor. According to the present invention, it is also possible to provide a method for contracting an artificial fibroin fiber, which is capable of safely obtaining at a sufficiently high contraction percentage.

BRIEF DESCRIPTION OF DRAWINGS

FIG. 6 is an explanatory view schematically showing an example of a production apparatus for producing highly contracted artificial fibroin fibers.

EMBODIMENTS FOR CARRYING OUT THE INVENTION

Figure 1:
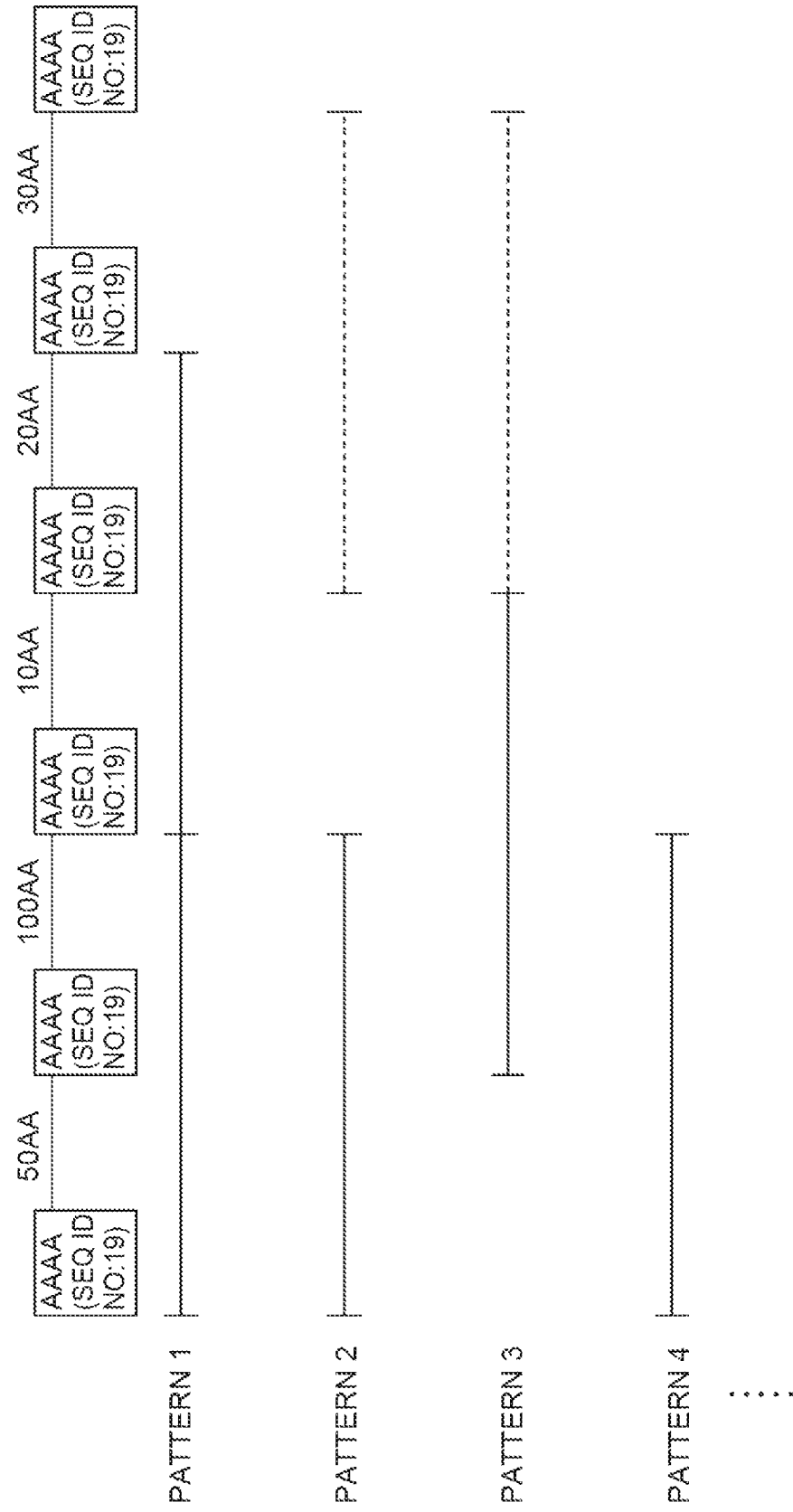
FIG. 1 is a schematic diagram showing a domain sequence of a modified fibroin (amino acid sequences of AAAA are set forth as SEQ ID NO:19).

Hereinafter, embodiments for carrying out the present invention will be described in detail. However, the present invention is not limited to the following embodiments.

[Highly Contracted Artificial Fibroin Fiber]

A highly contracted artificial fibroin fiber according to the present invention is a contracted artificial fibroin fiber including a modified fibroin. In the highly contracted artificial fibroin fiber according to the present embodiment, a contraction percentage defined by the following equation exceeds 7%.

Contraction percentage={1−(length of contracted artificial fibroin fiber/length of artificial fibroin fiber before being brought into contact with water after spinning)}×100(%)

<Modified Fibroin>

The modified fibroin according to the present embodiment is a protein including a domain sequence represented by Formula 1: $[(A)_n \text{ motif-REP}]_m$. The modified fibroin may further have an amino acid sequence (N-terminal sequence and C-terminal sequence) added to either or both of the N-terminal side and the C-terminal side of the domain sequence. The N-terminal sequence and the C-terminal sequence, although not limited thereto, are typically regions that do not have repetitions of amino acid motifs characteristic of fibroin and consist of amino acids of about 100 residues.

The term "modified fibroin" as used in the present specification means a synthetically produced fibroin (an artificial fibroin). The modified fibroin may be a fibroin whose domain sequence is different from the amino acid sequence of naturally occurring fibroin, or may be a fibroin whose amino acid sequence is the same as that of naturally occurring fibroin. The term "naturally occurring fibroin" as used herein is also a protein including a domain sequence represented by Formula 1: $[(A)_n \text{ motif-REP}]_m$.

The "modified fibroin" may be a fibroin in which the amino acid sequence of naturally occurring fibroin is used as it is; may be a fibroin; a fibroin whose amino acid sequence has been modified based on the amino acid sequence of naturally occurring fibroin (for example, a fibroin whose amino acid sequence has been modified by altering a gene sequence of cloned naturally occurring fibroin); or a fibroin artificially designed and synthesized independently of naturally occurring fibroin (for example, a fibroin having a desired amino acid sequence by chemically synthesizing a nucleic acid encoding the designed amino acid sequence), as long as it has the amino acid sequence specified in the present invention.

The term "domain sequence" as used herein refers to an amino acid sequence which produces a crystalline region (which typically corresponds to $(A)_n$ motif of an amino acid sequence) and an amorphous region (which typically corresponds to REP of an amino acid sequence) peculiar to fibroin and means an amino acid sequence represented by Formula 1: $[(A)_n \text{ motif-REP}]_m$. $(A)_n$ motif indicates an amino acid sequence mainly including an alanine residue, in which n is an integer of 2 to 20, is preferably 4 to 20, is more preferably 8 to 20, is even more preferably 10 to 20, is still even more preferably 4 to 16, is still even more preferably 8 to 16, and is particularly preferably 10 to 16. In addition, it is sufficient as long as a percentage alanine residues is 40% or more with respect to the total number of amino acid residues in the $(A)_n$ motif, but it is preferably 60% or more, more preferably 70% or more, still more preferably 80% or more, even still more preferably 90%, and may be 100% (which means that the $(A)_n$ motif consists of only alanine residues). REP represents an amino acid sequence consisting of 2 to 200 amino acid residues. m represents an integer of 2 to 300. A plurality of $(A)_n$ motifs may be the same amino acid sequence or different amino acid sequences. A plurality of REPs may be the same amino acid sequence or different amino acid sequences. Specific examples of proteins derived from the large nasogastric silkworm include a protein containing the amino acid sequence (PRT410) shown in SEQ ID NO: 9.

The modified fibroin according to the present embodiment can be obtained by, for example, performing modifications of an amino acid sequence corresponding to substitution, deletion, insertion and/or addition of one or a plurality of amino acid residues with respect to the genetic sequence of a cloned naturally occurring fibroin. Substitution, deletion, insertion and/or addition of amino acid residues can be carried out by methods well known to those skilled in the art, such as site-directed mutagenesis. Specifically, it can be carried out according to a method described in literatures such as Nucleic Acid Res. 10, 6487 (1982), and Methods in Enzymology, 100, 448 (1983).

Naturally occurring fibroin is a protein including a domain sequence represented by Formula 1: [(A)$_n$ motif-REP]$_m$, specifically, for example, a fibroin produced by insects or spiders.

Examples of the fibroin produced by insects include silk proteins produced by silkworms such as *Bombyx mori, Bombyx mandarina, Antheraea yamamai, Anteraea pernyi, Eriogyna pyretorum, Pilosamia Cynthia ricini, Samia cynthia, Caligura japonica, Antheraea mylitta*, and *Antheraea assama*; and Hornet silk proteins discharged by larvae of *Vespa simillima xanthoptera*.

A more specific example of the fibroin produced by insects may be a silkworm fibroin L chain (GenBank Accession No. M76430 (base sequence), AAA27840.1 (amino acid sequence)).

Examples of the fibroin produced by spiders include spider silk proteins produced by spiders belonging to the genus *Araneus* such as *Araneus ventricosus, Araneus diadematus, Araneus pinguis, Araneus pentagrammicus* and *Araneus nojimai*, spiders belonging to the genus *Neoscona* such as *Neoscona scylla, Neoscona nautica, Neoscona adianta* and *Neoscona scylloides*, spiders belonging to the genus *Pronus* such as *Pronous minutes*, spiders belonging to the genus *Cyrtarachne* such as *Cyrtarachne bufo* and *Cyrtarachne inaequalis*, spiders belonging to the genus *Gasteracantha* such as *Gasteracantha kuhli* and *Gasteracantha mammosa*, spiders belonging to the genus *Ordgarius* such as *Ordgarius hobsoni* and *Ordgarius sexspinosus*, spiders belonging to the genus *Argiope* such as *Argiope amoena, Argiope minuta* and *Argiope bruennich*, spiders belonging to the genus *Arachnura* such as *Arachnura logio*, spiders belonging to the genus *Acusilas* such as *Acusilas coccineus*, spiders belonging to the genus *Cytophora* such as *Cyrtophora moluccensis, Cyrtophora exanthematica* and *Cyrtophora unicolor*, spiders belonging to the genus *Poltys* such as *Poltys illepidus*, spiders belonging to the genus *Cyclosa* such as *Cyclosa octotuberculata, Cyclosa sedeculata, Cyclosa vallata* and *Cyclosa atrata*, and spiders belonging to the genus *Chorizopes* such as *Chorizopes nipponicus*; and spider silk proteins produced by spiders belonging to the genus *Tetragnatha* such as *Tetragnatha praedonia, Tetragnatha maxillosa, Tetragnatha extensa* and *Tetragnatha squamata*, spiders belonging to the genus *Leucauge* such as *Leucauge magnifica, Leucauge blanda* and *Leucauge subblanda*, spiders belonging to the genus *Nephila* such as *Nephila clavata* and *Nephila pilipes*, spiders belonging to the genus *Menosira* such as *Menosira ornata*, spiders belonging to the genus *Dyschiriognatha* such as *Dyschiriognatha tenera*, spiders belonging to the genus *Latrodectus* such as *Latrodectus mactans, Latrodectus hasseltii, Latrodectus geometricus* and *Latrodectus tredecimguttatus*, and spiders belonging to the family Tetragnathidae such as spiders belonging to the genus *Euprosthenops*. Examples of spider silk proteins include traction fiber proteins such as MaSp (MaSp1 and MaSp2) and ADF (ADF3 and ADF4), and MiSp (MiSp1 and MiSp2).

More specific examples of the fibroin produced by spiders include fibroin-3 (adf-3) [derived from *Araneus diadematus*] (GenBank Accession Number AAC47010 (amino acid sequence), U47855 (base sequence)), fibroin-4 (adf-4) [derived from *Araneus diadematus*](GenBank Accession Number AAC47011 (amino acid sequence), U47856 (base sequence)), dragline silk protein spidroin 1 [derived from *Nephila* clavipes] (GenBank Accession Number AAC04504 (amino acid sequence), U37520 (base sequence)), major ampullate spidroin 1 [derived from *Latrodectus hesperus*] (GenBank Accession Number ABR68856 (amino acid sequence)), EF595246 (base sequence)), dragline silk protein spidroin 2 [derived from *Nephila clavata*](GenBank Accession Number AAL32472 (amino acid sequence), AF441245 (base sequence)), major ampullate spidroin 1 [derived from *Euprosthenops australis*] (GenBank Accession Number CAJ00428 (amino acid sequence), AJ973155 (base sequence)) and major ampullate spidroin 2 [*Euprosthenops australis*] (GenBank Accession Number CAM32249.1 (amino acid sequence), AM490169 (base sequence)), minor ampullate silk protein 1 [*Nephila clavipes*] (GenBank Accession Number AAC14589.1 (amino acid sequence)), minor ampullate silk protein 2 [*Nephila clavipes*] (GenBank Accession Number AAC14591.1 (amino acid sequence)), and minor ampullate spidroin-like protein [*Nephilengys cruentata*] (GenBank Accession Number ABR37278.1 (amino acid sequence)).

As a more specific example of naturally occurring fibroin, fibroin in which sequence information is registered in NCBI GenBank can be further mentioned. For example, it can be confirmed by extracting sequences in which spidroin, ampullate, fibroin, "silk and polypeptide", or "silk and protein" is described as a keyword in DEFINITION among sequences containing INV as DIVISION among sequence information registered in NCBI GenBank, sequences in which a specific character string of products is described from CDS, or sequences in which a specific character string is described from SOURCE to TISSUE TYPE.

The modified fibroin according to the present embodiment may be modified silk fibroin (in which the amino acid sequence of silk protein produced by silkworm is modified), or may be a modified spider silk fibroin (in which the amino acid sequence of a spider silk protein produced by spiders is modified).

Specific example of the modified fibroin according to the present embodiment include a modified fibroin derived from the large nasogasus dragline protein produced in a spider major line (amodified fibroin according to the first embodiment), a modified fibroin having a reduced content of glycine residue (a modified fibroin according to the second embodiment), a modified fibroin in which the content of (A)$_n$ motif is reduced (a modified fibroin according to the third embodiment), and a modified fibroin in which the content of glycine residue and the content of (A) motif are reduced (a modified fibroin according to the fourth embodiment).

Examples of the modified fibroin according to the first embodiment includes a protein including a domain sequence represented by Formula 1: [(A)$_n$ motif-REP]$_m$. In the modified fibroin according to the first embodiment, in Formula 1, n is preferably an integer of 3 to 20, more preferably an integer of 4 to 20, even more preferably an integer of 8 to 20, and still even more preferably an integer of 10 to 20, still even more preferably an integer of 4 to 16, particularly preferably an integer of 8 to 16, and most preferably an integer of 10 to 16. In the modified fibroin according to the first embodiment, in Formula 1, the number of amino acid residues constituting the REP is preferably 10 to 200 residues, more preferably 10 to 150 residues, even more preferably 20 to 100 residues, and still even more preferably 20 to 75 residues. In the modified fibroin according to the first embodiment, a total number of residues of glycine residues, serine residues, and alanine residues contained in the amino acid sequence represented by Formula 1: [(A)$_n$ motif-REP]$_m$ is preferably 40% or more, more preferably 60% or more, and even more preferably 70% or more, with respect to the total number of amino acid residues.

The modified fibroin according to the first embodiment includes a unit of the amino acid sequence represented by Formula 1: [(A)$_n$ motif-REP]$_m$, and may be a polypeptide which is an amino acid sequence having a homology of 90% or more to the amino acid sequence whose C-terminal sequence is shown in any of SEQ ID NOs: 12 to 14, or the amino acid sequence set forth in any of SEQ ID NOs: 12 to 14.

The amino acid sequence set forth in SEQ ID NO: 12 is identical to the amino acid sequence consisting of 50 amino acid residues at the C-terminus of the amino acid sequence of ADF3 (GI: 1263287, NCBI); the amino acid sequence set forth in SEQ ID NO: 13 is identical to the amino acid sequence obtained by removing 20 residues from the C-terminus of the amino acid sequence set forth in SEQ ID NO: 12; and the amino acid sequence set forth in SEQ ID NO: 14 is identical to the amino acid sequence obtained by removing 29 residues from the C-terminus of the amino acid sequence set forth in SEQ ID NO: 12.

A more specific example of the modified fibroin according to the first embodiment may be a modified fibroin including (1-i) an amino acid sequence set forth in SEQ ID NO: 15 or (1-ii) an amino acid sequence having 90% or more sequence identity with the amino acid sequence set forth in SEQ ID NO: 15. The sequence identity is preferably 95% or more.

The amino acid sequence set forth in SEQ ID NO: 15 is an amino acid sequence in which the first to thirteenth repeat regions are increased to approximately double, and which is mutated so that the translation is terminated at the 1154th amino acid residue, in the amino acid sequence of ADF3 in which the amino acid sequence consisting of initiation codon, His10 tag, and HRV3C protease (Human rhinovirus 3C protease) recognition site (SEQ ID NO: 16) are added to the N terminus. The amino acid sequence at the C-terminus of the amino acid sequence set forth in SEQ ID NO: 15 is identical to the amino acid sequence set forth in SEQ ID NO: 3.

The modified fibroin of (1-i) may consist of the amino acid sequence set forth in SEQ ID NO: 15.

The modified fibroin according to the second embodiment has an amino acid sequence whose domain sequence has a reduced content of glycine residues as compared to naturally occurring fibroin. The modified fibroin can be said to have at least an amino acid sequence corresponding to substitution of one or a plurality of glycine residues in REP with another amino acid residue, as compared to naturally occurring fibroin.

The modified fibroin according to the second embodiment may be a modified fibroin in which the domain sequence has, in at least one motif sequence selected from GGX and GPGXX (where X represents an amino acid residue other than glycine) in REP, at least an amino acid sequence corresponding to substitution of one glycine residue in one or a plurality of the motif sequences with another amino acid residue, as compared to the naturally occurring fibroin.

The modified fibroin according to the second embodiment may be a modified fibroin in which the ratio of the motif sequence in which the glycine residue is substituted with another amino acid residue is 10% or more with respect to the entire motif sequence.

The modified fibroin according to the second embodiment may be a modified fibroin which includes a domain sequence represented by Formula 1: [(A)$_n$ motif-REP]$_m$, and has an amino acid sequence in which z/w is 30% or more, or has an amino acid sequence in which z/w is 50.9% or more, in the case where the total number of amino acid residues in the amino acid sequence consisting of XGX (where X represents an amino acid residue other than glycine) contained in all REPs in the sequence excluding the sequence from the (A)$_n$ motif located at the most C-terminal side to the C-terminus of the domain sequence from the domain sequence is defined as z, and the total number of amino acid residues in the sequence excluding the sequence from the (A)$_n$ motif located at the most C-terminal side to the C-terminus of the domain sequence from the domain sequence is defined as w. It is sufficient as long as the number of alanine residues is 83% or more relative to the total number of amino acid residues in the (A)$_n$ motif, but it is preferably 86% or more, more preferably 90% or more, still more preferably 95% or more, and even still more preferably 100% (which means that the (A)$_n$ motif consists of only alanine residues).

The modified fibroin according to the second embodiment is preferably a modified fibroin in which the content ratio of the amino acid sequence consisting of XGX is increased by substituting one glycine residue of the GGX motif with another amino acid residue. In the modified fibroin according to the second embodiment, the content ratio of the amino acid sequence consisting of GGX in the domain sequence is preferably 30% or less, more preferably 20% or less, still more preferably 10% or less, even still more preferably 6% or less, still further preferably 4% or less, and particularly preferably 2% or less. The content ratio of the amino acid sequence consisting of GGX in the domain sequence can be calculated by the same method as the calculation method of the content ratio (z/w) of the amino acid sequence consisting of XGX described below.

The calculation method of z/w will be described in more detail. First, from the domain sequence, an amino acid sequence consisting of XGX is extracted from all the REPs contained in the sequence excluding the sequence from the (A)$_n$ motif located at the most C-terminal side to the C-terminus of the domain sequence. The total number of amino acid residues constituting XGX is z. For example, in the case where 50 amino acid sequences consisting of XGX are extracted (there is no overlap), z is 50×3=150. Also, for example, in the case where X (central X) contained in two XGXs exists as in the case of the amino acid sequence consisting of XGXGX, it is calculated by subtracting the overlapping portion (in the case of XGXGX, it is 5 amino acid residues). w is the total number of amino acid residues contained in the sequence excluding the sequence from the (A)$_n$ motif located at the most C-terminal side to the C-terminus of the domain sequence from the domain sequence. For example, in the case of the domain sequence shown in FIG. 1, w is 4+50+4+100+4+10+4+20+4+30=230 (excluding the (A)$_n$ motif located at the most C-terminal side). Next, z/w (%) can be calculated by dividing z by w.

Figure 2:
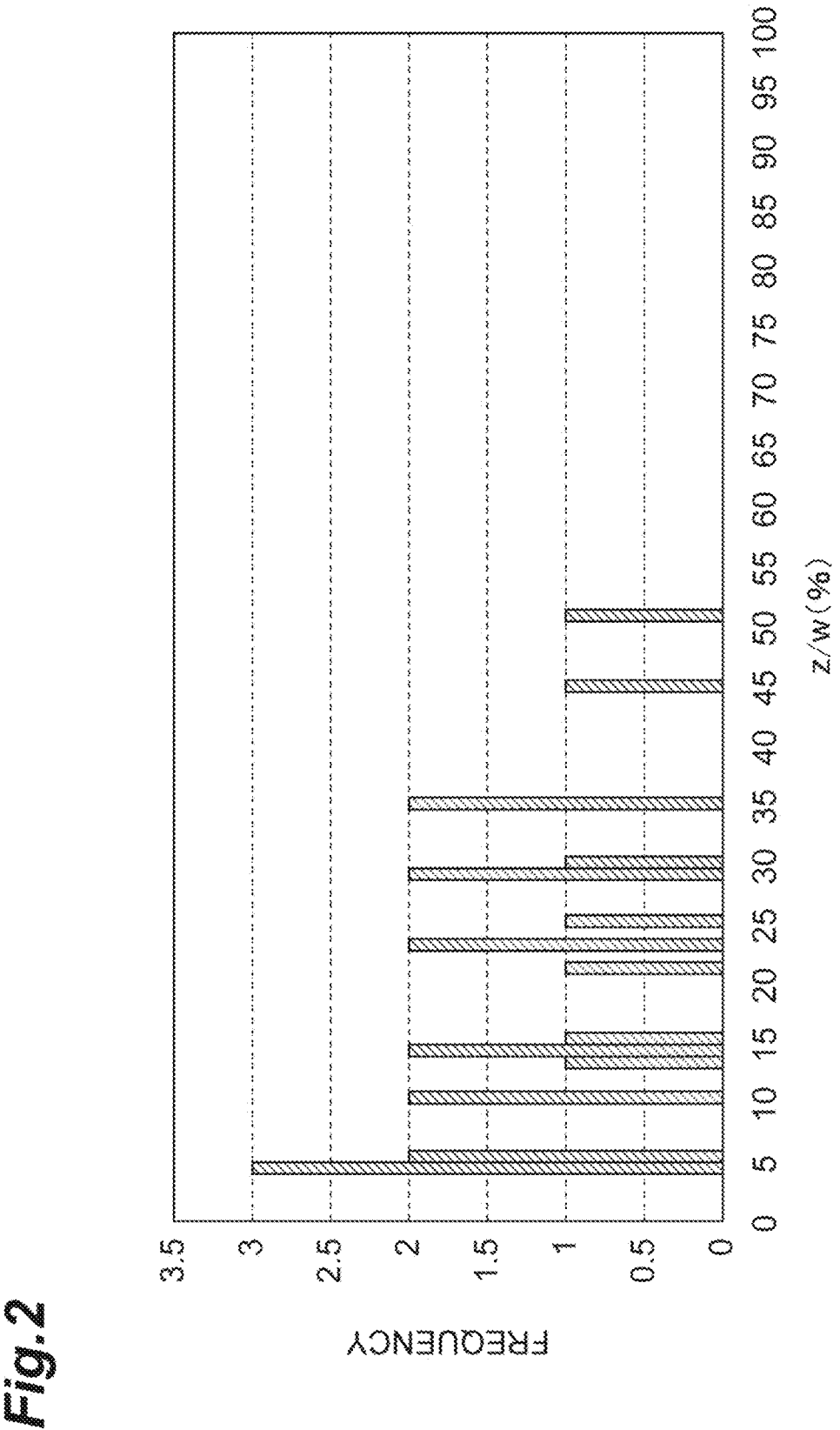
FIG. 2 is a graph showing a distribution of values of z/w (%) of naturally occurring fibroin.

Here, z/w in naturally occurring fibroin will be described. First, as described above, 663 types of fibroins (415 types of fibroins derived from spiders among them) were extracted by confirming fibroins with amino acid sequence information registered in NCBI GenBank by a method exemplified. z/w was calculated by the above-mentioned calculation method from the amino acid sequences of naturally occurring fibroins which include a domain sequence represented by Formula 1: [(A)$_n$ motif-REP]$_m$ and in which the content ratio of the amino acid sequence consisting of GGX in the fibroin is 6% or less, among all the extracted fibroins. The results are shown in FIG. 2. In FIG. 2, the horizontal axis represents z/w (%) and the vertical axis represents frequency. As is apparent from FIG. 2, z/w in naturally occurring fibroin is less than 50.9% (highest, 50.86%).

In the modified fibroin according to the second embodiment, z/w is preferably 50.9% or more, more preferably 56.1% or more, still more preferably 58.7% or more, even still more preferably 70% or more, and still further preferably 80% or more. The upper limit of z/w is not particularly limited, but it may be 95% or less, for example.

The modified fibroin according to the second embodiment can be obtained, for example, by substituting and modifying at least a part of a base sequence encoding a glycine residue from the gene sequence of cloned naturally occurring fibroin so as to encode another amino acid residue. At this time, one glycine residue in the GGX motif and GPGXX motif may be selected as the glycine residue to be modified, and substitution may be carried out such that z/w is 50.9% or more. Alternatively, the modified fibroin according to the embodiment can also be obtained, for example, by designing an amino acid sequence satisfying each of the above embodiments from the amino acid sequence of naturally occurring fibroin and chemically synthesizing a nucleic acid encoding the designed amino acid sequence. In any case, in addition to the modification corresponding to substitution of a glycine residue in REP with another amino acid residue from the amino acid sequence of naturally occurring fibroin, modification of the amino acid sequence corresponding to substitution, deletion, insertion and/or addition of one or a plurality of amino acid residues may be carried out.

The above-mentioned another amino acid residue is not particularly limited as long as it is an amino acid residue other than a glycine residue, but it is preferably a hydrophobic amino acid residue such as a valine (V) residue, a leucine (L) residue, an isoleucine (I) residue, a methionine (M) residue, a proline (P) residue, a phenylalanine (F) residue, or a tryptophan (W) residue, or a hydrophilic amino acid residue such as a glutamine (Q) residue, an asparagine (N) residue, a serine (S) residue, a lysine (K) residue, or a glutamic acid (E) residue, among which more preferred is a valine (V) residue, a leucine (L) residue, an isoleucine (I) residue or a glutamine (Q) residue, and still more preferred is a glutamine (Q) residue.

A more specific example of the modified fibroin according to the second embodiment may be a modified fibroin including (2-i) an amino acid sequence set forth in SEQ ID NO: 3, SEQ ID NO: 4, SEQ ID NO: 10, or SEQ ID NO: 17; or (2-ii) an amino acid sequence having 90% or more sequence identity with the amino acid sequence set forth in SEQ ID NO: 3, SEQ ID NO: 4, SEQ ID NO: 10, or SEQ ID NO: 17.

The modified fibroin of (2-i) will be described. The amino acid sequence set forth in SEQ ID NO: 3 is obtained by substituting GQX for all GGX in REP of the amino acid sequence set forth in SEQ ID NO: 1 corresponding to naturally occurring fibroin. The amino acid sequence set forth in SEQ ID NO: 4 is obtained by deleting the $(A)_n$ motif every other two positions from the N-terminal side to the C-terminal side from the amino acid sequence set forth in SEQ ID NO: 3 and further inserting one [$(A)_n$ motif-REP] before the C-terminal sequence. The amino acid sequence set forth in SEQ ID NO: 10 is obtained by inserting two alanine residues at the C-terminal side of each $(A)_n$ motif of the amino acid sequence set forth in SEQ ID NO: 4 and further substituting a part of glutamine (Q) residues with a serine (S) residue to delete a part of amino acids on the N-terminal side so as to be almost the same as the molecular weight of SEQ ID NO: 4. The amino acid sequence set forth in SEQ ID NO: 17 is an amino acid sequence in which a His tag has been added to the C-terminus of a sequence obtained by repeating, 4 times, the region of the 20 domain sequences present in the amino acid sequence set forth in SEQ ID NO: 10 (however, several amino acid residues at the C-terminal side of the region are substituted).

The value of z/w in the amino acid sequence set forth in SEQ ID NO: 1 (corresponding to naturally occurring fibroin) is 46.8%. The values of z/w in the amino acid sequence set forth in SEQ ID NO: 3, the amino acid sequence set forth in SEQ ID NO: 4, the amino acid sequence set forth in SEQ ID NO: 10, and the amino acid sequence set forth in SEQ ID NO: 17 are respectively 58.7%, 70.1%, 66.1%, and 70.0%. In addition, the values of x/y at the Giza ratio (to be described later) 1:1.8 to 1:11.3 of the amino acid sequences set forth in SEQ ID NOs: 1, 3, 4, 10, and 17 are respectively 15.0%, 15.0%, 93.4%, 92.7%, and 89.3%.

The modified fibroin of (2-i) may consist of an amino acid sequence set forth in SEQ ID NO: 3, SEQ ID NO: 4, SEQ ID NO: 10, or SEQ ID NO: 17.

The modified fibroin of (2-ii) includes an amino acid sequence having 90% or more sequence identity with the amino acid sequence set forth in SEQ ID NO: 3, SEQ ID NO: 4, SEQ ID NO: 10, or SEQ ID NO: 17. The modified fibroin of (2-ii) is also a protein including a domain sequence represented by Formula 1: [$(A)_n$ motif-REP]$_m$. The sequence identity is preferably 95% or more.

It is preferred that the modified fibroin of (2-ii) has 90% or more sequence identity with the amino acid sequence set forth in SEQ ID NO: 3, SEQ ID NO: 4, SEQ ID NO: 10, or SEQ ID NO: 17, and z/w is 50.9% or more in the case where the total number of amino acid residues in the amino acid sequence consisting of XGX (where X represents an amino acid residue other than glycine) contained in REP is defined as z, and the total number of amino acid residues of REP in the domain sequence is defined as w.

The above-mentioned modified fibroin may include a tag sequence at either or both of the N-terminus and C-terminus. This makes it possible to isolate, immobilize, detect and visualize the modified fibroin.

The tag sequence may be, for example, an affinity tag utilizing specific affinity (binding property, affinity) with another molecule. As a specific example of the affinity tag, a histidine tag (His tag) can be mentioned. The His tag is a short peptide in which about 4 to 10 histidine residues are arranged and has a property of specifically binding to a metal ion such as nickel, so it can be used for isolation of modified fibroin by chelating metal chromatography. A specific example of the tag sequence may be an amino acid sequence set forth in SEQ ID NO: 5 (amino acid sequence including His tag).

In addition, a tag sequence such as glutathione-S-transferase (GST) that specifically binds to glutathione or a maltose binding protein (MBP) that specifically binds to maltose can also be used.

Further, an "epitope tag" utilizing an antigen-antibody reaction can also be used. By adding a peptide (epitope) showing antigenicity as a tag sequence, an antibody against the epitope can be bound. Examples of the epitope tag include an HA (peptide sequence of hemagglutinin of influenza virus) tag, a myc tag, and a FLAG tag. The modified fibroin can easily be purified with high specificity by utilizing an epitope tag.

It is also possible to use a tag sequence which can be cleaved with a specific protease. By treating a protein adsorbed through the tag sequence with protease, it is also possible to recover the modified fibroin cleaved from the tag sequence.

A more specific example of the modified fibroin including the tag sequence may be a modified fibroin including (2-iii) an amino acid sequence set forth in SEQ ID NO: 8, SEQ ID NO: 9, SEQ ID NO: 11, or SEQ ID NO: 18; or (2-iv) an amino acid sequence having 90% or more sequence identity with the amino acid sequence set forth in SEQ ID NO: 8, SEQ ID NO: 9, SEQ ID NO: 11, or SEQ ID NO: 18.

The amino acid sequences set forth in SEQ ID NOs: 6, 7, 8, 9, 11, and 18 are amino acid sequences in which an amino acid sequence set forth in SEQ ID NO: 5 (including a His tag) is added at the N-terminus of the amino acid sequences set forth in SEQ ID NOs: 1, 2, 3, 4, 10, and 17, respectively.

The modified fibroin of (2-iii) may consist of an amino acid sequence set forth in SEQ ID NO: 8, SEQ ID NO: 9, SEQ ID NO: 11, or SEQ ID NO: 18.

The modified fibroin of (2-iv) includes an amino acid sequence having 90% or more sequence identity with the amino acid sequence set forth in SEQ ID NO: 8, SEQ ID NO: 9, SEQ ID NO: 11, or SEQ ID NO: 18. The modified fibroin of (2-iv) is also a protein including a domain sequence represented by Formula 1: [(A)$_n$ motif-REP]$_m$. The sequence identity is preferably 95% or more.

It is preferred that the modified fibroin of (2-iv) has 90% or more sequence identity with the amino acid sequence set forth in SEQ ID NO: 8, SEQ ID NO: 9, SEQ ID NO: 11, or SEQ ID NO: 18, and z/w is 50.9% or more in the case where the total number of amino acid residues in the amino acid sequence consisting of XGX (where X represents an amino acid residue other than glycine) contained in REP is defined as z, and the total number of amino acid residues of REP in the domain sequence is defined as w.

The above-mentioned modified fibroin may include a secretory signal for releasing the protein produced in the recombinant protein production system to the outside of a host. The sequence of the secretory signal can be appropriately set depending on the type of the host.

The modified fibroin according to the third embodiment has an amino acid sequence whose domain sequence has a reduced content of (A)$_n$ motif as compared to naturally occurring fibroin. The domain sequence of the modified fibroin can be said to have at least an amino acid sequence corresponding to deletion of one or a plurality of (A)$_n$ motifs, as compared to naturally occurring fibroin.

The modified fibroin according to the third embodiment may have an amino acid sequence corresponding to 10 to 40% deletion of the (A)$_n$ motif from naturally occurring fibroin.

The modified fibroin according to the third embodiment may be a modified fibroin whose domain sequence has at least an amino acid sequence corresponding to deletion of one (A)$_n$ motif per one to three (A)$_n$ motifs from the N-terminal side to the C-terminal side, as compared to naturally occurring fibroin.

The modified fibroin according to the third embodiment may be a modified fibroin whose domain sequence has at least an amino acid sequence corresponding to repetition of two consecutive (A)$_n$ motif deletions and one (A)$_n$ motif deletion in this order from the N-terminal side to the C-terminal side, as compared to the naturally occurring fibroin.

The modified fibroin according to the third embodiment may be a modified fibroin whose domain sequence has at least an amino acid sequence corresponding to deletion of the (A)$_n$ motif every other two positions from the N-terminal side to the C-terminal side.

The modified fibroin according to the third embodiment may be a modified fibroin which have a domain sequence represented by Formula 1: [(A)$_n$ motif-REP]$_m$, and have an amino acid sequence in which x/y is 20% or more, or have an amino acid sequence in which x/y is 50% or more, in the case where the number of amino acid residues in REPs of two adjacent [(A)$_n$ motif-REP] units is sequentially compared from the N-terminal side to the C-terminal side, and the number of amino acid residues in REP having a smaller number of amino acid residues is defined as 1, the maximum value of the total value of the number of amino acid residues in the two adjacent [(A)$_n$ motif-REP]units where the ratio of the number of amino acid residues in the other REP is 1.8 to 11.3 is defined as x, and the total number of amino acid residues of the domain sequence is y. It is sufficient as long as the number of alanine residues is 83% or more relative to the total number of amino acid residues in the (A)$_n$ motif, but it is preferably 86% or more, more preferably 90% or more, still more preferably 95% or more, and even still more preferably 100% (which means that the (A)$_n$ motif consists of only alanine residues).

A method of calculating x/y will be described in more detail with reference to FIG. 1. FIG. 1 shows a domain sequence excluding N-terminal sequence and C-terminal sequence from modified fibroin. This domain sequence has a sequence of (A)$_n$ motif-first REP (50 amino acid residues)-(A)$_n$ motif-second REP (100 amino acid residues)-(A)$_n$ motif-third REP (10 amino acid residues)-(A)$_n$ motif-fourth REP (20 amino acid residues)-(A)$_n$ motif-fifth REP (30 amino acid residues)-(A)$_n$ motif from the N-terminal side (left side).

The two adjacent [(A)$_n$ motif-REP] units are sequentially selected from the N-terminal side to the C-terminal side so as not to overlap. At this time, an unselected [(A)$_n$ motif-REP] unit may exist. FIG. 1 shows a pattern 1 (a comparison between first REP and second REP and a comparison between third REP and fourth REP), a pattern 2 (a comparison between first REP and second REP and a comparison between fourth REP and fifth REP), a pattern 3 (a comparison between second REP and third REP and a comparison between fourth REP and fifth REP), and a pattern 4 (a comparison between first REP and second REP). There are other selection methods besides this.

Next, for each pattern, the number of amino acid residues of each REP in the selected two adjacent [(A)$_n$ motif-REP] units is compared. The comparison is carried out by obtaining the ratio of the number of amino acid residues of the other REP in the case where one REP having a smaller number of amino acid residues is 1. For example, in the case of comparing the first REP (50 amino acid residues) and the second REP (100 amino acid residues), the ratio of the number of amino acid residues of the second REP is 100/50=2 in the case where the first REP having a smaller number of amino acid residues is 1. Similarly, in the case of comparing the fourth REP (20 amino acid residues) and the fifth REP (30 amino acid residues), the ratio of the number of amino acid residues of the fifth REP is 30/20=1.5 in the case where the fourth REP having a smaller number of amino acid residues is 1.

In FIG. 1, a set of [(A)$_n$ motif-REP] units in which the ratio of the number of amino acid residues of the other REP is 1.8 to 11.3 in the case where one REP having a smaller number of amino acid residues is 1 is indicated by a solid line. In the present specification, such a ratio is referred to as a Giza ratio. A set of [(A)$_n$ motif-REP] units in which the ratio of the number of amino acid residues of the other REP is less than 1.8 or more than 11.3 in the case where one REP having a smaller number of amino acid residues is 1 is indicated by a broken line.

In each pattern, the number of all amino acid residues of two adjacent [(A)$_n$ motif-REP] units indicated by solid lines (including not only the number of amino acid residues of REP but also the number of amino acid residues of $(A)_n$ motif) is combined. Then, the total values thus combined are compared and the total value of the pattern whose total value is the maximum (the maximum value of the total value) is defined as x. In the example shown in FIG. 1, the total value of the pattern 1 is the maximum.

Next, x/y (%) can be calculated by dividing x by the total amino acid residue number y of the domain sequence.

In the modified fibroin according to the third embodiment, x/y is preferably 50% or more, more preferably 60% or more, still more preferably 65% or more, even still more preferably 70% or more, still further preferably 75% or more, and particularly preferably 80% or more. The upper limit of x/y is not particularly limited, and it may be 100% or less, for example. In a case where a Giza ratio is 1:1.9 to 1:11.3, x/y is preferably 89.6% or more; in a case where a Giza ratio is 1:1.8 to 1:3.4, x/y is preferably 77.1% or more; in a case where a Giza ratio is 1:1.9 to 1:8.4, x/y is preferably 75.9% or more; and in a case where a Giza ratio is 1:1.9 to 1:4.1, x/y is preferably 64.2% or more.

In a case where the modified fibroin according to the third embodiment is a modified fibroin in which at least seven of $(A)_n$ motifs which are present in plural in the domain sequence are composed of only alanine residues, x/y is preferably 46.4% or more, is more preferably 50% or more, is even more preferably 55% or more, is still even more preferably 60% or more, is still even more preferably 70% or more, and is particularly preferable 80% or more. The upper limit of x/y is not particularly limited, and may be 100% or less.

Figure 3:
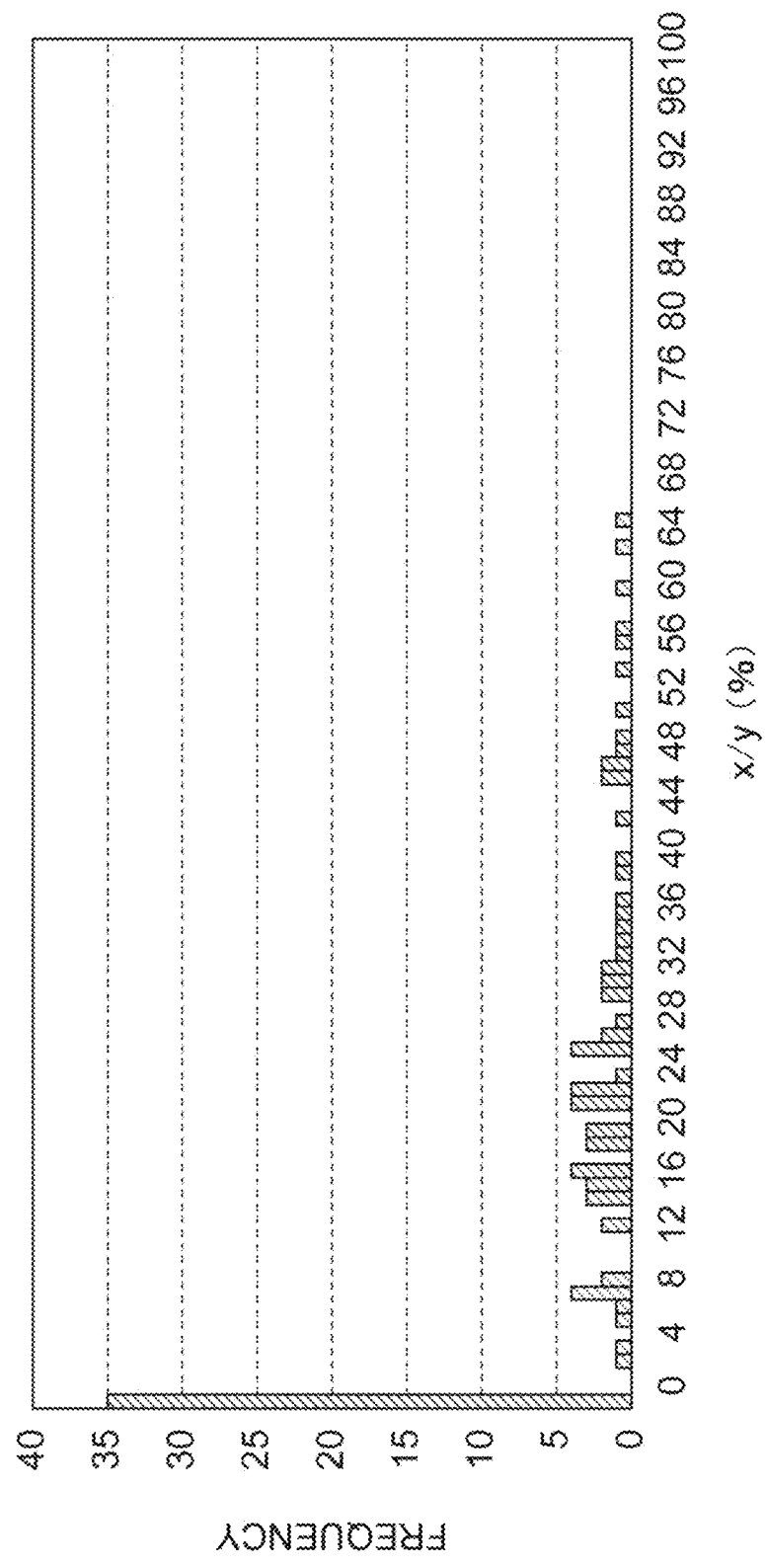
FIG. 3 is a graph showing a distribution of values of x/y (%) of naturally occurring fibroin.

Here, x/y in naturally occurring fibroin will be described. First, as described above, 663 types of fibroins (415 types of fibroins derived from spiders among them) were extracted by confirming fibroins with amino acid sequence information registered in NCBI GenBank by a method exemplified. x/y was calculated by the above-mentioned calculation method from the amino acid sequences of naturally occurring fibroins which include a domain sequence represented by Formula 1: $[(A)_n$ motif-REP], among all the extracted fibroins. FIG. 3 shows the results in the case where the Giza ratio is 1:1.9 to 1:4.1.

In FIG. 3, the horizontal axis represents x/y (%) and the vertical axis represents frequency. As is apparent from FIG. 3, x/y in naturally occurring fibroin is less than 64.2% (highest, 64.14%).

The modified fibroin according to the third embodiment can be obtained, for example, from a gene sequence of cloned naturally occurring fibroin, by deleting one or a plurality of the sequences encoding the $(A)_n$ motif such that x/y is 64.2% or more. Further, the modified fibroin including a domain sequence with a reduced $(A)_n$ motif content can also be obtained, for example, by designing an amino acid sequence corresponding to deletion of one or a plurality of $(A)_n$ motifs such that x/y is 64.2% or more, from the amino acid sequence of naturally occurring fibroin, and chemically synthesizing a nucleic acid encoding the designed amino acid sequence. In any case, in addition to the modification corresponding to deletion of $(A)_n$ motif from the amino acid sequence of naturally occurring fibroin, modification of the amino acid sequence corresponding to substitution, deletion, insertion and/or addition of one or a plurality of amino acid residues may be carried out.

A more specific example of the modified fibroin according to the third embodiment may be a modified fibroin including (3-i) an amino acid sequence set forth in SEQ ID NO: 2, SEQ ID NO: 4, SEQ ID NO: 10, or SEQ ID NO: 17; or (3-ii) an amino acid sequence having 90% or more sequence identity with the amino acid sequence set forth in SEQ ID NO: 2, SEQ ID NO: 4, SEQ ID NO: 10, or SEQ ID NO: 17.

The modified fibroin of (3-i) will be described. The amino acid sequence set forth in SEQ ID NO: 2 is obtained by deleting the $(A)_n$ motif every other two positions from the N-terminal side to the C-terminal side from the amino acid sequence set forth in SEQ ID NO: 1 corresponding to naturally occurring fibroin and further inserting one $[(A)_n$ motif-REP] before the C-terminal sequence. The amino acid sequence set forth in SEQ ID NO: 4 is obtained by substituting GQX for all GGX in REP of the amino acid sequence set forth in SEQ ID NO: 2. The amino acid sequence set forth in SEQ ID NO: 10 is obtained by inserting two alanine residues at the C-terminal side of each $(A)_n$ motif of the amino acid sequence set forth in SEQ ID NO: 4 and further substituting a part of glutamine (Q) residues with a serine (S) residue to delete a part of amino acids on the N-terminal side so as to be almost the same as the molecular weight of SEQ ID NO: 4. The amino acid sequence set forth in SEQ ID NO: 17 is an amino acid sequence in which a His tag has been added to the C-terminus of a sequence obtained by repeating, 4 times, the region of the 20 domain sequences present in the amino acid sequence set forth in SEQ ID NO: 10 (however, several amino acid residues at the C-terminal side of the region are substituted).

The value of x/y in the Giza ratio 1:1.8 to 1:11.3 of the amino acid sequence set forth in SEQ ID NO: 1 (corresponding to naturally occurring fibroin) is 15.0%. Values of x/y in the amino acid sequence set forth in SEQ ID NO: 2 and the amino acid sequence set forth in SEQ ID NO: 4 are both 93.4%. The value of x/y in the amino acid sequence set forth in SEQ ID NO: 10 is 92.7%. The value of x/y in the amino acid sequence set forth in SEQ ID NO: 17 is 89.3%. Values of z/w in the amino acid sequences set forth in SEQ ID NOs: 1, 2, 4, 10, and 17 are 46.8%, 56.2%, 70.1%, 66.1%, and 70.0%, respectively.

The modified fibroin of (3-i) may consist of an amino acid sequence set forth in SEQ ID NO: 2, SEQ ID NO: 4, SEQ ID NO: 10, or SEQ ID NO: 17.

The modified fibroin of (3-ii) includes an amino acid sequence having 90% or more sequence identity with the amino acid sequence set forth in SEQ ID NO: 2, SEQ ID NO: 4, SEQ ID NO: 10, or SEQ ID NO: 17. The modified fibroin of (3-ii) is also a protein including a domain sequence represented by Formula 1: $[(A)_n$ motif-REP]$_m$. The sequence identity is preferably 95% or more.

The modified fibroin of (3-ii) preferably has 90% or more sequence identity with the amino acid sequence set forth in SEQ ID NO: 2, SEQ ID NO: 4, SEQ ID NO: 10, or SEQ ID NO: 17, and has an amino acid sequence in which x/y is 64.2% or more, in the case where the number of amino acid residues in REPs of two adjacent $[(A)_n$ motif-REP] units is sequentially compared from the N-terminal side to the C-terminal side, and the number of amino acid residues in REP having a smaller number of amino acid residues is defined as 1, the maximum value of the total value of the number of amino acid residues in the two adjacent $[(A)_n$ motif-REP] units where the ratio of the number of amino acid residues in the other REP is 1.8 to 11.3 (a Giza ratio of 1:1.8 to 1:11.3) is defined as x, and the total number of amino acid residues of the domain sequence is y.

The above-mentioned modified fibroin may include the above-mentioned tag sequence at either or both of the N-terminus and C-terminus.

A more specific example of the modified fibroin including the tag sequence may be a modified fibroin including (3-iii) an amino acid sequence set forth in SEQ ID NO: 7, SEQ ID NO: 9, SEQ ID NO: 11, or SEQ ID NO: 18; or (3-iv) an amino acid sequence having 90% or more sequence identity with the amino acid sequence set forth in SEQ ID NO: 7, SEQ ID NO: 9, SEQ ID NO: 11, or SEQ ID NO: 18.

The amino acid sequences set forth in SEQ ID NOs: 6, 7, 8, 9, 11, and 18 are amino acid sequences in which an amino acid sequence set forth in SEQ ID NO: 5 (including a His tag) is added at the N-terminus of the amino acid sequences set forth in SEQ ID NOs: 1, 2, 3, 4, 10, and 17, respectively.

The modified fibroin of (3-iii) may consist of an amino acid sequence set forth in SEQ ID NO: 7, SEQ ID NO: 9, SEQ ID NO: 11, or SEQ ID NO: 18.

The modified fibroin of (3-iv) includes an amino acid sequence having 90% or more sequence identity with the amino acid sequence set forth in SEQ ID NO: 7, SEQ ID NO: 9, SEQ ID NO: 11, or SEQ ID NO: 18. The modified fibroin of (3-iv) is also a protein including a domain sequence represented by Formula 1: $[(A)_n\ \text{motif-REP}]_m$. The sequence identity is preferably 95% or more.

The modified fibroin of (3-iv) preferably has 90% or more sequence identity with the amino acid sequence set forth in SEQ ID NO: 7, SEQ ID NO: 9, SEQ ID NO: 11, or SEQ ID NO: 18, and has an amino acid sequence in which x/y is 64.2% or more, in the case where the number of amino acid residues in REPs of two adjacent $[(A)_n\ \text{motif-REP}]$ units is sequentially compared from the N-terminal side to the C-terminal side, and the number of amino acid residues in REP having a smaller number of amino acid residues is defined as 1, the maximum value of the total value of the number of amino acid residues in the two adjacent $[(A)_n\ \text{motif-REP}]$ units where the ratio of the number of amino acid residues in the other REP is 1.8 to 11.3 is defined as x, and the total number of amino acid residues of the domain sequence is y.

The above-mentioned modified fibroin may include a secretory signal for releasing the protein produced in the recombinant protein production system to the outside of a host. The sequence of the secretory signal can be appropriately set depending on the type of the host.

The modified fibroin of the fourth embodiment is a modified fibroin in which the domain sequence has an amino acid sequence in which the content of glycine residues is reduced in addition to having a reduced content of $(A)_n$ motifs as compared to naturally occurring fibroin. The domain sequence of the modified fibroin can be said to further have an amino acid sequence corresponding at least the substitution of one or a plurality of glycine residues in REP with another amino acid residue, in addition to deletion of one or a plurality of $(A)_n$ motifs, as compared to naturally occurring fibroin. That is, the modified fibroin is a modified fibroin having the features of the above-described modified fibroin according to the second embodiment and the above-described modified fibroin according to the third embodiment. Specific aspects and the like are as described in the modified fibroin according to the second and third embodiments.

A more specific example of the modified fibroin according to the fourth embodiment may be a modified fibroin including (4-i) an amino acid sequence set forth in SEQ ID NO: 4, SEQ ID NO: 10, or SEQ ID NO: 17; or (4-ii) an amino acid sequence having 90% or more sequence identity with the amino acid sequence set forth in SEQ ID NO: 4, SEQ ID NO: 10, or SEQ ID NO: 17. Specific aspects of the modified fibroin including the amino acid sequence set forth in SEQ ID NO: 4, SEQ ID NO: 10, or SEQ ID NO: 17 are as described above.

<Method for Producing Modified Fibroin>

The modified fibroin according to the present embodiment can be produced by, for example, expressing the nucleic acid by a nucleic acid sequence encoding the modified fibroin, and a host transformed with an expression vector having one or a plurality of regulatory sequences operably linked to the nucleic acid sequence.

A method for producing a nucleic acid encoding the modified fibroin is not particularly limited. A nucleic acid can be produced by, for example, a method in which a gene encoding natural fibroin is amplified and cloned by polymerase chain reaction (PCR) or the like, and modified by genetic engineering method; or a method of chemically synthesizing a nucleic acid. A method for chemically synthesizing a nucleic acid is not particularly limited, and, for example, genes can be chemically synthesized by a method in which of linking, by PCR or the like, oligonucleotides that are automatically synthesized by AKTA oligopilot plus 10/100 (GE Healthcare Japan Ltd.) or the like, based on the amino acid sequence information of fibroin obtained from the NCBI web database and the like. At this time, in order to facilitate purification and/or confirmation of the modified fibroin, a nucleic acid encoding a modified fibroin consisting of an amino acid sequence obtained by adding an amino acid sequence consisting of a start codon and a His10 tag to the N terminus of the above amino acid sequence may be synthesized.

The regulatory sequence is a sequence (for example, a promoter, an enhancer, a ribosome binding sequence, or a transcription termination sequence) that controls the expression of a modified fibroin in a host, and can be appropriately selected depending on the type of the host. As a promoter, an inducible promoter which functions in host cells and is capable of inducible expression of modified fibroin may be used. An inducible promoter is a promoter that can control transcription due to the presence of an inducer (expression inducer), the absence of a repressor molecule, or physical factors such as an increase or decrease in temperature, osmotic pressure, or pH value.

The type of the expression vector such as a plasmid vector, a viral vector, a cosmid vector, a fosmid vector, or an artificial chromosome vector can be appropriately selected depending on the type of the host. As the expression vector, an expression vector which can autonomously replicate in a host cell or can be incorporated into a chromosome of a host and which contains a promoter at a position capable of transcribing the nucleic acid encoding the modified fibroin is suitably used.

Both prokaryotes and eukaryotes such as yeast, filamentous fungi, insect cells, animal cells, and plant cells can be suitably used as hosts.

Examples of hosts of the prokaryote include bacteria belonging to the genus *Escherichia*, *Brevibacillus*, *Serratia*, *Bacillus*, *Microbacterium*, *Brevibacterium*, *Corynebacterium* and *Pseudomonas*. Examples of microorganisms belonging to the genus *Escherichia* include *Escherichia coli* and the like. Examples of microorganisms belonging to the genus *Brevibacillus* include *Brevibacillus agri* and the like. Examples of microorganisms belonging to the genus *Serratia* include *Serratia liquefaciens* and the like. Examples of microorganisms belonging to the genus *Bacillus* include *Bacillus subtilis* and the like. Examples of microorganisms belonging to the genus *Microbacterium* include *Microbacterium ammoniaphilum*. Examples of microorganisms belonging to the genus *Brevibacterium* include *Brevibacterium divaricatum* and the like. Examples of microorganisms belonging to the genus *Corynebacterium* include *Corynebacterium ammoniagenes* and the like. Examples of microorganisms belonging to the genus *Pseudomonas* include *Pseudomonas putida* and the like.

In a case where a prokaryote is used as a host, examples of vectors into which a nucleic acid encoding the modified fibroin is introduced include pBTrp2 (manufactured by Boehringer Mannheim), pGEX (manufactured by Pharmacia), pUC18, pBluescriptII, pSupex, pET22b, pCold, pUB110, and pNCO2 (Japanese Unexamined Patent Publication No. 2002-238569), and the like.

Examples of eukaryotic hosts include yeast and filamentous fungi (mold and the like). Examples of yeasts include a yeast which belongs to the genus *Saccharomyces, Pichia, Schizosaccharomyces*, and the like. Examples of filamentous fungi include filamentous fungi belonging to the genus *Aspergillus, Penicillium, Trichoderma*, and the like.

In a case where a eukaryote is used as a host, examples of vectors into which a nucleic acid encoding the modified fibroin is introduced include YEP13 (ATCC37115), YEp24 (ATCC37051), and the like. As a method for introducing an expression vector into the foregoing host cell, any method can be used as long as it introduces DNA into the host cell. Examples thereof include a method using calcium ions [Proc. Natl. Acad. Sci. USA, 69, 2110 (1972)], an electroporation method, a spheroplast method, a protoplast method, a lithium acetate method, a competent method, and the like.

As a method for expressing a nucleic acid by a host transformed with an expression vector, secretory production, fusion protein expression, or the like, in addition to direct expression, can be carried out according to the method described in Molecular Cloning, 2nd edition.

The modified fibroin can be produced, for example, by culturing a host transformed with the expression vector in a culture medium, producing and accumulating the modified fibroin in the culture medium, and then collecting the modified fibroin from the culture medium. The method for culturing the host in a culture medium can be carried out according to a method commonly used for culturing a host.

In the case where the host is a prokaryote such as *Escherichia coli* or a eukaryote such as yeast, any of a natural medium and a synthetic medium may be used as a culture medium as long as it contains a carbon source, a nitrogen source, inorganic salts and the like which can be assimilated by the host and it is capable of efficiently culturing the host.

As the carbon source, any carbon source that can be assimilated by the transformed microorganism may be used. Examples of the carbon source that can be used include carbohydrates such as glucose, fructose, sucrose, and molasses, starch and starch hydrolyzates containing them, organic acids such as acetic acid and propionic acid, and alcohols such as ethanol and propanol. Examples of the nitrogen source that can be used include ammonium salts of inorganic or organic acids such as ammonia, ammonium chloride, ammonium sulfate, ammonium acetate and ammonium phosphate, other nitrogen-containing compounds, peptone, meat extract, yeast extract, corn steep liquor, casein hydrolyzate, soybean cake and soybean cake hydrolyzate, various fermented microbial cells and digested products thereof. As inorganic salts, it is possible to use potassium dihydrogen phosphate, dipotassium phosphate, magnesium phosphate, magnesium sulfate, sodium chloride, ferrous sulfate, manganese sulfate, copper sulfate, and calcium carbonate.

Culture of a prokaryote such as *Escherichia coli* or a eukaryote such as yeast can be carried out under aerobic conditions such as shaking culture or deep aeration stirring culture. The culture temperature is, for example, 15° C. to 40° C. The culture time is usually 16 hours to 7 days. It is preferable to maintain the pH of the culture medium during the culture at 3.0 to 9.0. The pH of the culture medium can be adjusted using an inorganic acid, an organic acid, an alkali solution, urea, calcium carbonate, ammonia, or the like.

In addition, antibiotics such as ampicillin and tetracycline may be added to the culture medium as necessary during the culture. In the case of culturing a microorganism transformed with an expression vector using an inducible promoter as a promoter, an inducer may be added to the medium as necessary. For example, in the case of culturing a microorganism transformed with an expression vector using a lac promoter, isopropyl-β-D-thiogalactopyranoside or the like is used, and in the case of culturing a microorganism transformed with an expression vector using a trp promoter, indole acrylic acid or the like may be added to the medium.

Isolation and purification of the expressed modified fibroin can be performed by a commonly used method. For example, in the case where the modified fibroin is expressed in a dissolved state in cells, the host cells are recovered by centrifugation after completion of the culture, suspended in an aqueous buffer solution, and then disrupted using an ultrasonicator, a French press, a Manton-Gaulin homogenizer, a Dyno-Mill, or the like to obtain a cell-free extract. From the supernatant obtained by centrifuging the cell-free extract, a purified preparation can be obtained by a method commonly used for isolation and purification of a modified fibroin, that is, a solvent extraction method, a salting-out method using ammonium sulfate or the like, a desalting method, a precipitation method using an organic solvent, an anion exchange chromatography method using a resin such as diethylaminoethyl (DEAE)-Sepharose or DIAION HPA-75 (manufactured by Mitsubishi Kasei Kogyo Kabushiki Kaisha), an cation exchange chromatography method using a resin such as S-Sepharose FF (Pharmacia Corporation), a hydrophobic chromatography method using a resin such as butyl sepharose or phenyl sepharose, a gel filtration method using a molecular sieve, an affinity chromatography method, a chromatofocusing method, an electrophoresis method such as isoelectric focusing or the like, alone or in combination thereof.

In addition, in the case where the modified fibroin is expressed by the formation of an insoluble matter in the cell, similarly, the host cells are recovered, disrupted and centrifuged to recover the insoluble matter of the modified fibroin as a precipitated fraction. The recovered insoluble matter of the modified fibroin can be solubilized with a protein denaturing agent. After this operation, a purified preparation of modified fibroin can be obtained by the same isolation and purification method as described above. In the case where the modified fibroin is secreted extracellularly, the modified fibroin can be recovered from the culture supernatant. That is, a culture supernatant is obtained by treating the culture by a technique such as centrifugation, and a purified preparation can be obtained from the culture supernatant by using the same isolation and purification method as described above.

<Artificial Fibroin Fiber>

The artificial fibroin fiber according to the present embodiment is a fiber that obtained by spinning the above-described modified fibroin, and that contains the above-described modified fibroin as a main component.

<Method for Producing Artificial Fibroin Fiber>

The artificial fibroin fiber according to the present embodiment can be produced by a known spinning method. That is, for example, in a case of producing artificial fibroin fibers containing the modified fibroin as a main component, first, a dope solution is prepared by adding and dissolving the modified fibroin produced according to the method described above in a solvent such as dimethyl sulfoxide (DMSO), N,N-dimethylformamide (DMF), or hexafluoroisopronol (HFIP), together with inorganic salt as a dissolution promoter. Next, using this dope solution, spinning is performed by a known spinning method such as wet-type spinning, dry-type spinning, dry-wet-type spinning, or melting-type spinning, and thereby target artificial fibroin fibers can be obtained. Preferred spinning methods include wet-type spinning or dry-wet-type spinning.

Figure 4:
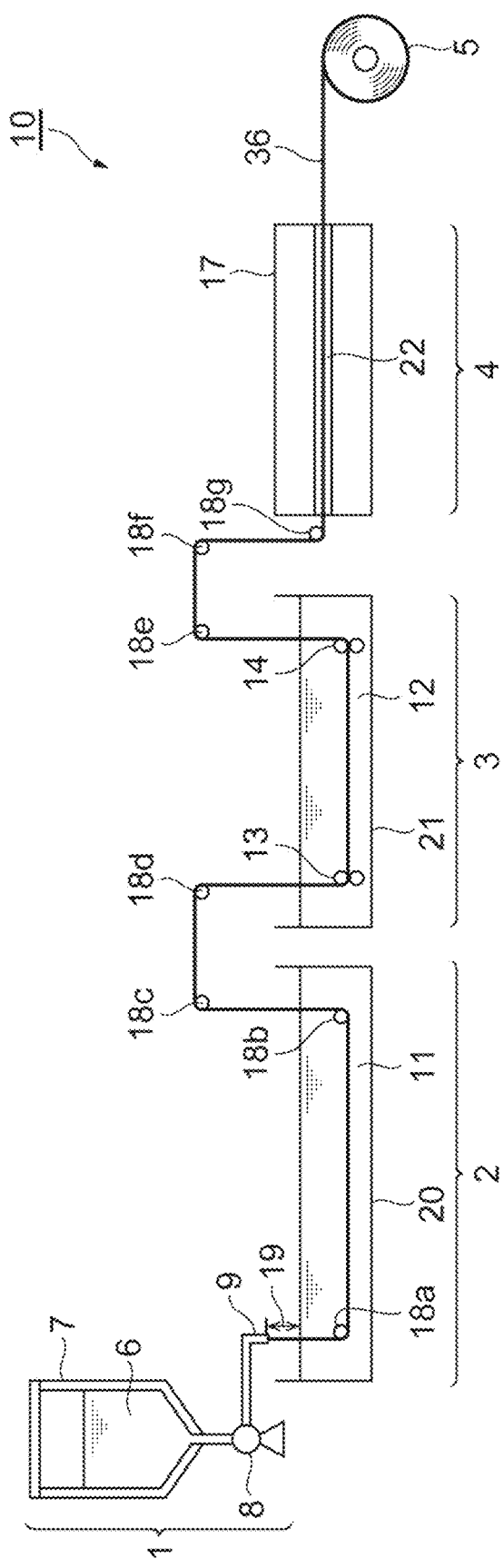
FIG. 4 is an explanatory view schematically showing an example of a spinning apparatus for producing artificial fibroin fibers.

FIG. 4 is an explanatory view schematically showing an example of a spinning apparatus for producing artificial fibroin fibers. A spinning apparatus 10 shown in FIG. 4 is an example of a spinning apparatus for dry-wet-type spinning, and includes an extrusion apparatus 1, an undrawn yarn production apparatus 2, a wet heat drawing apparatus 3, and a drying apparatus 4.

A spinning method using the spinning apparatus 10 will be described. First, a dope solution 6 stored in a storage tank 7 is pushed out of a spinneret 9 by a gear pump 8. In the lab scale, the dope solution may be filled into a cylinder and pushed out of the nozzle using a syringe pump. Next, the extruded dope solution 6 is supplied through an air gap 19 into a coagulation liquid 11 of a coagulation liquid tank 20, the solvent is removed, the modified fibroin is coagulated, and a fibrous coagulated body is formed. Next, the fibrous coagulated body is supplied into warm water 12 in a drawing bath 21 and drawn. A draw ratio is determined by a speed ratio between a feed nip roller 13 and a pick-up nip roller 14. Thereafter, the drawn fibrous coagulated body is supplied to the drying apparatus 4 and dried in a thread guide 22, and thereby the artificial fibroin fiber as a wound body 5 is obtained. 18a to 18g are yarn guides.

The coagulation liquid 11 may be a solution capable of desolvation, and examples thereof include lower alcohols having 1 to 5 carbon atoms such as methanol, ethanol and 2-propanol, and acetone. The coagulation liquid 11 may appropriately contain water. The temperature of the coagulation liquid 11 is preferably 0° C. to 30° C. In the case where a syringe pump having a nozzle with a diameter of 0.1 to 0.6 mm is used as the spinneret 9, the extrusion rate is preferably 0.2 to 6.0 ml/hr and more preferably 1.4 to 4.0 ml/hr per hole. The distance the coagulated protein passes in the coagulation liquid 11 (substantially, the distance from the yarn guide 18a to the yarn guide 18b) may be any length that enables efficient desolvation, and is, for example, 200 to 500 mm. The take-off speed of the undrawn yarn may be, for example, 1 to 20 m/min and preferably 1 to 3 m/min. The residence time in the coagulation liquid 11 may be, for example, 0.01 to 3 minutes and preferably 0.05 to 0.15 minutes. Further, drawing (pre-drawing) may be carried out in the coagulation liquid 11. The coagulation liquid tank 20 may be provided in multiple stages, and the drawing may be carried out in each stage or a specific stage, as necessary.

For the drawing carried out in a case of obtaining the artificial fibroin fiber, for example, dry heat drawing is also employed in addition to the above-described pre-drawing performed in the coagulation liquid tank 20, and wet heat drawing performed in the drawing bath 21.

The wet heat drawing can be carried out in warm water, in a solution obtained by adding an organic solvent or the like to warm water, or during steam heating. The temperature may be, for example, 50° C. to 90° C. and preferably 75° C. to 85° C. In wet heat drawing, undrawn yarn (or pre-drawn yarn) can be drawn, for example, 1 to 10 times, preferably 2 to 8 times.

Dry heat drawing can be carried out using an electric tube furnace, a dry heat plate, or the like. The temperature may be, for example, 140° C. to 270° C. and preferably 160° C. to 230° C. In dry heat drawing, undrawn yarn (or pre-drawn yarn) can be drawn, for example, 0.5 to 8 times, preferably 1 to 4 times.

The wet heat drawing and the dry heat drawing may be carried out individually, or they may be carried out in multiple stages or in combination. That is, wet heat drawing and dry heat drawing can be carried out in an appropriate combination in such a manner that the first stage drawing is carried out by wet heat drawing and the second stage drawing is carried out by dry heat drawing, or the first stage drawing is carried out by wet heat drawing and the second stage drawing is carried out by wet heat drawing, and the third stage drawing is further carried out by dry heat drawing.

The lower limit of the final draw ratio is preferably more than 1 time, 2 times or more, 3 times or more, 4 times or more, 5 times or more, 6 times or more, 7 times or more, 8 times or more, or 9 times or more a draw ratio of the undrawn yarn (or pre-drawn yarn). The upper limit is preferably 40 times or less, 30 times or less, 20 times or less, 15 times or less, 14 times or less, 13 times or less, 12 times or less, 11 times or less, or 10 times or less.

<Highly Contracted Artificial Fibroin Fiber>

The highly contracted artificial fibroin fiber according to the present embodiment is formed by contraction of the above-mentioned artificial fibroin fibers. The above-mentioned artificial fibroin fibers can be contracted at a higher contraction percentage as compared with known protein fibers of the related art, and can be contracted at a higher contraction percentage under milder conditions than those of known synthetic fibers of the related art.

Accordingly, in the highly contracted artificial fibroin fiber according to the present embodiment, a contraction percentage defined by the following equation exceeds 7%.

Contraction percentage={1−(length of contracted artificial fibroin fiber/length of artificial fibroin fiber before being brought into contact with water after spinning)}×100(%)

The contraction percentage of the highly contracted artificial fibroin fiber according to the present embodiment is preferably 15% or more, is more preferably more than 25%, is even more preferably 32% or more, is still even more preferably 40% or more, is still even more preferably 48% or more, is particularly preferably 56% or more, is even more particularly preferably 64% or more, and is most preferably 72% or more. The upper limit of the contraction percentage is generally 80% or less.

<Method for Producing Highly Contracted Artificial Fibroin Fiber>

A method for producing a highly contracted artificial fibroin fiber includes a step of contracting an artificial fibroin fiber containing a modified fibroin by bringing the artificial fibroin fiber into contact with water below a boiling point (hereinafter will be referred to as the "contraction step").

In the contraction step, the artificial fibroin fibers are brought into contact with water below a boiling point (hereinafter also referred to as a "contact step"). Thereby, the artificial fibroin fiber can be contracted regardless of the external force. The contraction with no external force of the artificial fibroin fibers in the contact step is considered to occur because of the following reasons, for example. In other words, as one reason, it is considered to occur due to a secondary structure and a tertiary structure of artificial fibroin. For example, as another reason, it is considered that, in artificial fibroin fibers having residual stress due to drawing or the like in the production process, residual stress is relieved by water infiltrating between fibers or into fibers. Accordingly, it is considered that a contraction percentage of the artificial fibroin fiber in the contraction step can be optionally controlled, for example, in accordance with the size of the draw ratio in the production process of the artificial fibroin fiber described above.

A temperature of the water with which the artificial fibroin fibers are brought into contact in the contact step may be less than a boiling point. Accordingly, handleability and workability of the contraction process are improved. In addition, from the viewpoint of sufficiently shortening a contraction time, the lower limit value of the temperature of water is preferably 10° C. or more, is more preferably 40° C. or more, and is even more preferably 70° C. or more. The upper limit of the temperature of water is preferably 90° C. or less.

A method of bringing the artificial fibroin fibers into contact with water in the contact step is not particularly limited. Examples of methods include a method of immersing artificial fibroin fibers in water, a method of spraying water on artificial fibroin fibers at normal temperature or in a state of heated steam, and the like; a method of exposing artificial fibroin fibers to a high-humidity environment filled with water vapor; and the like. Among these methods, in the contact step, the method of immersing artificial fibroin fibers in water is preferable because shortening of a contraction time can be effectively achieved, and simplification of processing equipment can be realized.

In the contact step, when the artificial fibroin fibers are brought into contact with water in a loosened state, the artificial fibroin fibers may not only be contracted but also crimped in an undulating manner. In order to prevent the occurrence of such crimp, for example, the contact step is carried out in a state where the artificial fibroin fibers are not loosened, by bringing the artificial fibroin fibers into contact with water below a boiling point while stretching (stretching) them in a fiber axial direction.

The contraction step may further include, in addition to the contact step, drying of the artificial fibroin fibers after being brought into contact with water (hereinafter, will be referred to as the "drying step").

The drying step is a step of drying the artificial fibroin fibers which have been subjected to the contact step. Drying may be, for example, natural drying or forced drying using a drying facility. As the drying equipment, any known drying equipment of contact type or non-contact type can be used. In addition, a drying temperature is not particularly limited as long as it is lower than the temperature at which, for example, proteins contained in the artificial fibroin fiber are decomposed or the artificial fibroin fiber is thermally damage. In general, the temperature is within a range of 20° C. to 150° C., and the temperature is preferably within a range of 50° C. to 100° C. When the temperature is within this range, the artificial fibroin fibers are dried more quickly and efficiently without thermal damage to the artificial fibroin fibers or decomposition of proteins contained in the artificial fibroin fibers. A drying time is appropriately set in accordance with the drying temperature and the like, and for example, a time in which the influence of overdrying on the quality and physical properties of the artificial fibroin fiber can be eliminated as much as possible.

In the method for producing a highly contracted artificial fibroin fiber according to the present embodiment, a highly contracted artificial fibroin fiber having a contraction percentage exceeding 7% can be obtained through the contraction step (the contact step and, if necessary, the drying step).

The contraction percentage of the obtained highly contracted artificial fibroin fiber according to the present embodiment is preferably 15% or more, is more preferably more than 25%, is even more preferably 32% or more, is still even more preferably 40% or more, is still even more preferably 48% or more, is particularly preferably 56% or more, is even more particularly preferably 64% or more, and is most preferably 72% or more. The upper limit of the contraction percentage is generally 80% or less.

Figure 5:
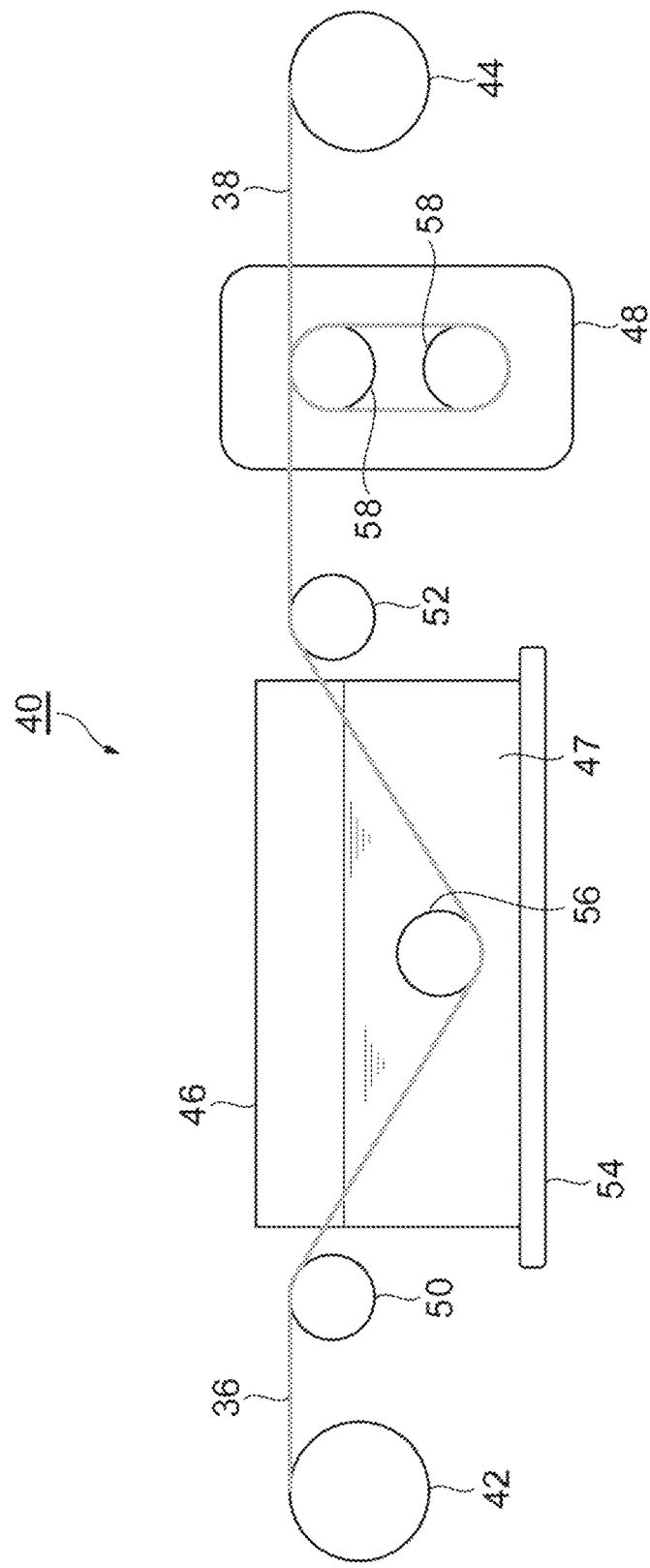
FIG. 5 is an explanatory view schematically showing an example of a production apparatus for producing highly contracted artificial fibroin fibers.

FIG. 5 is an explanatory view schematically showing an example of a production apparatus for producing highly contracted artificial fibroin fibers. A production apparatus 40 shown in FIG. 5 is configured to include a feed roller 42 for delivering artificial fibroin fibers, a winder 44 for winding highly contracted artificial fibroin fibers 38, a water bath 46 for performing the contact step, and a dryer 48 for performing the drying step.

More specifically, the feed roller 42 can be loaded with a wound product of artificial fibroin fibers 36, and the artificial fibroin fibers 36 are continuously automatically delivered from the wound product of the artificial fibroin fibers 36 by rotation of an electric motor or the like (not shown). The winder 44 can continuously and automatically wind the highly contracted artificial fibroin fibers 38 produced through the contact step and the drying step after being fed out from the feed roller 42 by the rotation of an electric motor (not shown). A feed speed of the artificial fibroin fibers 36 by the feed roller 42 and the winding speed of the highly contracted artificial fibroin fibers 38 by the winder 44 can be controlled independently of each other.

The water bath 46 and the dryer 48 are disposed between the feed roller 42 and the winder 44 respectively on the upstream side and the downstream side in a feeding direction of the artificial fibroin fibers 36. The production apparatus 40 shown in FIG. 5 has relay rollers 50 and 52 relaying the artificial fibroin fibers 36 traveling from the feed roller 42 toward the winder 44.

The water bath 46 has a heater 54, and hot water 47 heated by the heater 54 is accommodated in the water bath 46. In addition, in the water bath 46, a tension roller 56 is installed in a state of being immersed in the hot water 47. Accordingly, the artificial fibroin fibers 36 delivered from the feed roller 42 travel toward the winder 44 while being immersed in the hot water 47 in a state of being wound around the tension roller 56 in the water bath 46. An immersion time of the artificial fibroin fibers 36 in the hot water 47 is appropriately controlled according to the traveling speed of the artificial fibroin fibers 36.

The dryer 48 has a pair of hot rollers 58. The pair of hot rollers 58 can be wound with artificial fibroin fibers 36 which are separated from the water bath 46 and travel toward the winder 44 side. Accordingly, the artificial fibroin fibers 36 immersed in the hot water 47 in the water bath 46 are heated by the pair of hot rollers 58 in the dryer 48 and dried, and then is further fed toward the winder 44.

When producing the highly contracted artificial fibroin fibers 38 using the production apparatus 40 having such a structure, first, for example, the wound product of the artificial fibroin fibers 36 spun using the spinning apparatus 10 shown in FIG. 4 is mounted on the feed roller 42. Next, the artificial fibroin fibers 36 are continuously sent out from the feed roller 42 and immersed in the hot water 47 in the water bath 46. At this time, for example, the winding speed of the winder 44 is made slower than the feed speed of the feed roller 42. Accordingly, generation of crimp can be prevented since the artificial fibroin fibers 36 are contracted by being brought into contact with the hot water 47 in a tensioned state so as not to be loosened between the feed roller 42 and the winder 44.

Next, the artificial fibroin fibers 36 contracted in the hot water 47 in the water bath 46 are heated by the pair of hot rollers 58 of the dryer 48. Thereby, the contracted artificial fibroin fibers 36 are dried to form the highly contracted artificial fibroin fibers 38. At this time, by controlling a ratio of the feed speed of the feed roller 42 and the winding speed of the winder 44, it is possible to further contract the artificial fibroin fibers 36, or to make its length not to be changed. Next, the obtained highly contracted artificial fibroin fibers 38 are wound on the winder 44, and thereby the wound product of the highly contracted artificial fibroin fibers 38 is obtained.

Instead of the pair of hot rollers 58, the artificial fibroin fibers 36 may be dried using a drying facility such as a dry heat plate 64 as shown in FIG. 6. Also in this case, by adjusting a relative speed between the feed speed of the feed roller 42 and the winding speed of the winder 44 in the same manner as in the case of using the pair of hot rollers 58 as a drying facility, it is possible to further contract the artificial fibroin fibers 36, or to make its length not to be changed. The drying means is constituted by the dry heat plate 64.

As described above, by using the production apparatus 40, the target highly contracted artificial fibroin fibers 38 can be produced automatically, continuously, and very easily.

FIG. 6 is an explanatory view schematically showing another example of a production apparatus for producing highly contracted artificial fibroin fibers. FIG. 6(*a*) shows a processing apparatus that is included in the production apparatus and that implements the contact step. FIG. 6(*b*) shows a drying apparatus that is included in the production apparatus and that implements the drying step. The production apparatus shown in FIG. 6 has a processing apparatus 60 for performing the contact step on the artificial fibroin fibers 36, and a drying apparatus 62 for drying the artificial fibroin fibers 36 on which the contact step has been performed by the processing apparatus 60; and has a structure in which these apparatuses are independently installed with each other.

More specifically, the processing apparatus 60 shown in FIG. 6(*a*) has a structure in which the dryer 48 is omitted from the production apparatus 40 shown in FIG. 5, and the feed roller 42, the water bath 46, and the winder 44 are arranged in order from the upstream side to the downstream side in a traveling direction of the artificial fibroin fibers 36. Such processing apparatus 60 is designed to cause the artificial fibroin fibers 36 delivered from the feed roller 42 to be immersed in hot water 47 in the water bath 46 and contracted before being wound up by the winder 44. In addition, the structure is configured such that the artificial fibroin fibers 36 contracted in the hot water 47 is wound by the winder 44.

The drying apparatus 62 shown in FIG. 6(*b*) has the feed roller 42, the winder 44, and the dry heat plate 64. The dry heat plate 64 is disposed between the feed roller 42 and the winder 44 such that a dry heat surface 66 comes into contact with the artificial fibroin fibers 36 and extends along the traveling direction thereof. In this drying apparatus 62, as described above, by controlling a ratio of the feed speed of the feed roller 42 and the winding speed of the winder 44, it is possible to further contract the artificial fibroin fibers 36, or to make its length not to be changed.

In a case of using the production apparatus having such a structure, for example, the target highly contracted artificial fibroin fibers 38 can be produced by firstly contracting the artificial fibroin fibers 36 by the processing apparatus 60, and then drying the artificial fibroin fibers 36 by the drying apparatus 62.

The feed roller 42 and the winder 44 may be omitted from the processing apparatus 60 shown in FIG. 6(*a*), and the processing apparatus may be configured with only the water bath 46. In a case of using the production apparatus having such a processing apparatus, for example, highly contracted artificial fibroin fibers are produced in a so-called batch system.

<Use Applications of Highly Contracted Artificial Fibroin Fiber>

The highly contracted artificial fibroin fiber according to the present invention has excellent tactile properties and flexibility because it is contracted at a high contraction percentage. Therefore, it is suitable as fibers used for, for example, clothing and bedding.

[Method for Contracting Artificial Fibroin Fiber]

The method for producing a highly contracted artificial fibroin fiber of the present invention described above can be perceived as a method for contracting an artificial fibroin fiber, including a step of contracting an artificial fibroin fiber containing a modified fibroin by bringing the artificial fibroin fiber into contact with water below a boiling point, in which a contraction percentage defined by the following equation exceeds 7%.

$$\text{Contraction percentage} = \{1 - (\text{length of contracted artificial fibroin fiber}/\text{length of artificial fibroin fiber before being brought into contact with water after spinning})\} \times 100(\%)$$

EXAMPLES

Hereinafter, the present invention will be described more specifically based on examples and the like. However, the present invention is not limited to the following Examples.

[(1) Production of Modified Fibroin (Artificial Fibroin)]

(Synthesis of Nucleic Acid Encoding Modified Fibroin and Construction of Expression Vector)

A modified fibroin (PRT399) having the amino acid sequence set forth in SEQ ID NO: 7, a modified fibroin (PRT380) having the amino acid sequence set forth in SEQ ID NO: 8, a modified fibroin (PRT410) having the amino acid sequence set forth in SEQ ID NO 9, and a modified fibroin (PRT799) having the amino acid sequence set forth in SEQ ID NO: 18 were designed.

The amino acid sequence set forth in SEQ ID NO: 7 is obtained by adding an amino acid sequence (including a His tag) set forth in SEQ ID NO: 5 at the N terminus of an amino acid sequence in which the $(A)_n$ motif is deleted every other two positions from the N-terminal side to the C-terminal side from the amino acid sequence set forth in SEQ ID NO: 1 corresponding to naturally occurring fibroin and one [(A)) motif-REP] is inserted before the C-terminal sequence.

The amino acid sequence set forth in SEQ ID NO: 8 is obtained by adding an amino acid sequence (including a His tag) set forth in SEQ ID NO: 5 at the N terminus of an amino acid sequence in which all GGX in REP of the amino acid sequence set forth in SEQ ID NO: 1 corresponding to naturally occurring fibroin is substituted by GQX.

The amino acid sequence set forth in SEQ ID NO: 9 is obtained by adding an amino acid sequence (including a His tag) set forth in SEQ ID NO: 5 at the N terminus of an amino acid sequence in which all GGX in REP of the amino acid sequence set forth in SEQ ID NO: 2 is substituted by GQX.

The amino acid sequence set forth in SEQ ID NO: 18 is obtained by adding an amino acid sequence (including a His tag) set forth in SEQ ID NO: 5 at the N terminus of an amino acid sequence in which a His tag has been added to the C-terminus of a sequence obtained by repeating, 4 times, the region of the 20 domain sequences present in the amino acid sequence set forth in SEQ ID NO: 9 (however, several amino acid residues at the C-terminal side of the region are substituted).

Nucleic acids encoding the four types of designed modified fibroin were synthesized respectively. In the nucleic acid, an NdeI site was added to the 5' end and an EcoRI site was added downstream of the stop codon. These four kinds of nucleic acids were cloned into a cloning vector (pUC118). Thereafter, the same nucleic acid was cleaved by restriction enzyme treatment with NdeI and EcoRI, and then recombined into a protein expression vector pET-22b(+) to obtain an expression vector.

(Expression of Modified Fibroin)

*Escherichia coli* BLR (DE3) was transformed with the obtained expression vector pET-22b (+). The transformed *Escherichia coli* was cultured in 2 mL of an LB medium containing ampicillin for 15 hours. The culture solution was added to 100 mL of a seed culture medium (Table 1) containing ampicillin so that the $OD_{600}$ was 0.005. The temperature of the culture solution was maintained at 30° C. and the flask culture was carried out (for about 15 hours) until the $OD_{600}$ reached 5, thereby obtaining a seed culture solution.

TABLE 1

| Seed culture medium | |
|---|---|
| Reagents | Concentration (g/L) |
| Glucose | 5.0 |
| $KH_2PO_4$ | 4.0 |
| $K_2HPO_4$ | 9.3 |
| Yeast Extract | 6.0 |
| Ampicillin | 0.1 |

The seed culture solution was added to ajar fermenter to which 500 ml of a production medium (Table 2) had been added so that the $OD_{600}$ was 0.05. The culture was carried out while maintaining the culture solution temperature at 37° C. and keeping the pH constant at 6.9. Further, the dissolved oxygen concentration in the culture solution was maintained at 20% of the dissolved oxygen saturation concentration.

TABLE 2

| Production medium | |
|---|---|
| Reagents | Concentration (g/L) |
| Glucose | 12.0 |
| $KH_2PO_4$ | 9.0 |
| $MgSO_4 \cdot 7H_2O$ | 2.4 |
| Yeast Extract | 15 |
| $FeSO_4 \cdot 7H_2O$ | 0.04 |
| $MnSO_4 \cdot 5H_2O$ | 0.04 |
| $CaCl_2 \cdot 2H_2O$ | 0.04 |
| ADEKANOL (LG-295S, Adeka Corporation) | 0.1 (mL/L) |

Immediately after glucose in the production medium was completely consumed, a feed solution (455 g/1 L of glucose and 120 g/1 L of Yeast Extract) was added at a rate of 1 mL/min. The culture was carried out while maintaining the culture solution temperature at 37° C. and keeping the pH constant at 6.9. The culture was carried out for 20 hours while maintaining the dissolved oxygen concentration in the culture solution at 20% of the dissolved oxygen saturation concentration. Thereafter, 1 M isopropyl-β-thiogalactopyranoside (IPTG) was added to the culture solution to a final concentration of 1 mM to induce the expression of the target modified fibroin. Twenty hours after addition of IPTG, the culture solution was centrifuged to recover the bacterial cells. SDS-PAGE was carried out using the bacterial cells prepared from the culture solution before the addition of IPTG and after the addition of IPTCQ and the expression of the target modified fibroin was confirmed by the appearance of a band of a size of the target modified fibroin depending on the addition of IPTG (Purification of Modified Fibroin)

The bacterial cells recovered 2 hours after the addition of IPTG were washed with 20 mM Tris-HCl buffer solution (pH 7.4). The bacterial cells after washing were suspended in 20 mM Tris-HCl buffer solution (pH 7.4) containing about 1 mM PMSF, and the cells were disrupted with a high-pressure homogenizer (available from GEA Niro Soavi SpA). The disrupted cells were centrifuged to obtain a precipitate. The obtained precipitate was washed with 20 mM Tris-HCl buffer solution (pH 7.4) until high purity. The precipitate after washing was suspended in 8 M guanidine buffer solution (8 M guanidine hydrochloride, 10 mM sodium dihydrogen phosphate, 20 mM NaCl, 1 mM Tris-HCl, pH 7.0) so as to have a concentration of 100 mg/mL, and dissolved by stirring with a stirrer at 60° C. for 30 minutes. After dissolution, dialysis was carried out with water using a dialysis tube (cellulose tube 36/32 manufactured by Sanko Junyaku Co., Ltd.). The white aggregated protein obtained after dialysis was recovered by centrifugation. Water was removed from the recovered aggregated protein with a freeze dryer, and the freeze-dried powder of the modified fibroin was obtained.

The degree of purification of the target modified fibroin in the freeze-dried powder thus obtained was confirmed by image analysis of polyacrylamide gel electrophoresis results of the powder using TotalLab (Nonlinear Dynamics Ltd.). As a result, the purity of each modified fibroin was about 85%.

[(2) Production of Artificial Fibroin Fiber]

(Preparation of Dope Solution)

Dimethyl sulfoxide (DMSO) in which LiCl was dissolved such that a concentration became 4.0% by mass was prepared as a solvent, the freeze-dried powder of the modified fibroin was added thereto such that a concentration became 18% by mass or 24% by mass (refer to Table 3), and the mixture was dissolved for 3 hours using a shaker. Thereafter, insolubles and bubbles were removed, and a modified fibroin solution was obtained.

(Spinning)

The obtained modified fibroin solution was used as a dope solution (spinning undiluted solution), and a spun and drawn artificial fibroin fiber was produced by dry-wet-type spinning using a spinning apparatus that can be regarded as the spinning apparatus 10 shown in FIG. 4. The spinning apparatus used is an apparatus in which a second undrawn yarn production apparatus (a second bath) is further provided between an undrawn yarn production apparatus 2 (a first bath) and a wet heat drawing apparatus 3 (a third bath) in the spinning apparatus 10 shown in FIG. 1. Conditions for dry-wet-type spinning are as follows.

Extrusion nozzle diameter: 0.2 mm

Extrusion speed (discharge amount): refer to Table 3

Liquid and temperature in the first bath to third bath: refer to Table 3

Winding speed: refer to Table 3

Total draw ratio: refer to Table 3
Drying temperature: 60° C.
Air gap length: refer to Table 3

TABLE 3

| | Dope solution | | Discharge | | First bath | | Second bath | | Third bath | | Total | |
|---|---|---|---|---|---|---|---|---|---|---|---|---|
| | Modified fibroin | Concentration (% by mass) | Discharge amount (mg/min) | Air gap length (mm) | Liquid | Temperature (° C.) | Liquid | Temperature (° C.) | Liquid | Temperature (° C.) | Winding speed (m/min) | draw ratio (times) |
| Production Example 1 | PRT799 | 24 | 53.8 | 1-2 | 100% methanol | −5 | 100% methanol | 16 | Water | 17 | 1.45 | 1 |
| Production Example 2 | | | | | | | | | | | 2.9 | 2 |
| Production Example 3 | | | | | | | | | | | 4.35 | 3 |
| Production Example 4 | | | | | | | | | | | 5.8 | 4 |
| Production Example 5 | | 18 | 55.1 | | | | | | | | 1.49 | 1 |
| Production Example 6 | | | | | | | | | | | 2.98 | 2 |
| Production Example 7 | | | | | | | | | | | 4.47 | 3 |
| Production Example 8 | | | | | | | | | | | 5.96 | 4 |
| Production Example 9 | PRT410 | 24 | 51.9 | 0 | | −11 | | 14 | | | 1.4 | 1 |
| Production Example 10 | | | | | | | | | | | 2.8 | 2 |
| Production Example 11 | | | | | | | | | | | 4.2 | 3 |
| Production Example 12 | | | | | | | | | | | 5.6 | 4 |
| Production Example 13 | PRT399 | | 51.1 | | | | | | | | 1.38 | 1 |
| Production Example 14 | | | | | | | | | | | 2.76 | 2 |
| Production Example 15 | | | | | | | | | | | 4.14 | 3 |
| Production Example 16 | PRT380 | | 47.2 | | | | | 11 | | | 1.27 | 1 |
| Production Example 17 | | | | | | | | | | | 2.54 | 2 |
| Production Example 18 | | | | | | | | | | | 3.81 | 3 |
| Production Example 19 | | | | | | | | | | | 5.08 | 4 |

[(3) Production and Evaluation of Highly Contracted Artificial Fibroin Fiber]
(Contraction Process)

Highly contracted artificial fibroin fibers were produced by performing, on each artificial fibroin fiber obtained in Production Examples 1 to 19, a contact step of bringing fibers into contact with water below a boiling point (hereinafter referred to as "primary contraction"), or a drying step of drying at room temperature after performing the contact step (hereinafter referred to as "secondary contraction").

<Primary Contraction>

A plurality of artificial fibroin fibers each having a length of 30 cm were cut out from the wound product of the artificial fibroin fibers obtained in Production Examples 1 to 19. The plurality of artificial fibroin fibers were bundled to obtain an artificial fibroin fiber bundle having a fineness of 150 denier. Each artificial fibroin fiber bundle was attached with 0.8 g of a lead weight, and in this state, each artificial fibroin fiber bundle was immersed in water having a temperature shown in Tables 4 to 7 for 10 minutes (the contact step). Thereafter, the length of each artificial fibroin fiber bundle was measured. The measurement of the length of the artificial fibroin fiber bundle in water was carried out with the artificial fibroin fiber bundle attached with a 0.8 g lead weight in order to eliminate the crimp of the artificial fibroin fiber bundle. Next, a contraction percentage (%) of each artificial fibroin fiber was calculated according to Equation I. In Equation I, L0 indicates the length of the artificial fibroin fiber bundle (herein, 30 cm) before being brought into contact with water after spinning, and Lw indicates the length of the artificial fibroin fiber bundle that has undergone primary contraction.

$$\text{contraction percentage (primary contraction percentage)} = \{1-(Lw/L0)\} \times 100(\%) \quad \text{Equation I:}$$

<Secondary Contraction>

After immersing in water at the primary contraction (the contact step), the artificial fibroin fiber bundles were removed from the water. The artificial fibroin fiber bundles taken out were dried at room temperature for 2 hours with a 0.8 g lead weight attached thereto (the drying step). After drying, the length of each artificial fibroin fiber bundle was measured. Next, a contraction percentage (%) of each artificial fibroin fiber was calculated according to Equation II. In Equation II, L0 indicates the length of the artificial fibroin fiber bundle (herein, 30 cm) before being brought into contact with water after spinning, and Lwd indicates the length of the artificial fibroin fiber bundle that has undergone primary contraction.

$$\text{contraction percentage (secondary contraction percentage)} = \{1-(Lwd/L0)\} \times 100(\%) \quad \text{Equation II:}$$

The results are shown in Tables 4 to 7.

TABLE 4

| Artificial fibroin fiber | | Temperature of water below boiling point (° C.) | Primary contraction (%) | Secondary contraction (%) |
|---|---|---|---|---|
| Production Example 1 | 24 wt % PRT799 × 1 | 20 | 0.0 | 7.8 |
| Production Example 2 | 24 wt % PRT799 × 2 | | −1.2 | 10.3 |
| Production Example 3 | 24 wt % PRT799 × 3 | | 7.2 | 21.2 |
| Production Example 4 | 24 wt % PRT799 × 4 | | 13.5 | 26.3 |
| Production Example 6 | 18 wt % PRT799 × 2 | | −2.3 | 9.5 |
| Production Example 7 | 18 wt % PRT799 × 3 | | 6.0 | 19.7 |
| Production Example 8 | 18 wt % PRT799 × 4 | | 14.3 | 27.5 |
| Production Example 2 | 24 wt % PRT799 × 2 | 40 | −5.3 | 7.2 |
| Production Example 3 | 24 wt % PRT799 × 3 | | 8.7 | 21.3 |
| Production Example 4 | 24 wt % PRT799 × 4 | | 14.5 | 26.0 |
| Production Example 6 | 18 wt % PRT799 × 2 | | −4.3 | 7.3 |
| Production Example 7 | 18 wt % PRT799 × 3 | | 6.2 | 18.3 |
| Production Example 8 | 18 wt % PRT799 × 4 | | 16.0 | 28.7 |
| Production Example 3 | 24 wt % PRT799 × 3 | 60 | 6.8 | 21.0 |
| Production Example 4 | 24 wt % PRT799 × 4 | | 15.0 | 27.5 |
| Production Example 6 | 18 wt % PRT799 × 2 | | −1.5 | 10.7 |
| Production Example 7 | 18 wt % PRT799 × 3 | | 3.3 | 18.2 |
| Production Example 8 | 18 wt % PRT799 × 4 | | 16.2 | 29.0 |

TABLE 5

| Artificial fibroin fiber | | Temperature of water below boiling point (° C.) | Primary contraction (%) | Secondary contraction (%) |
|---|---|---|---|---|
| Production Example 10 | 24 wt % PRT410 × 2 | 20 | −2.3 | 8.7 |
| Production Example 11 | 24 wt % PRT410 × 3 | | 4.7 | 16.7 |
| Production Example 12 | 24 wt % PRT410 × 4 | | 10.3 | 22.3 |
| Production Example 11 | 24 wt % PRT410 × 3 | 40 | 4.7 | 17.5 |
| Production Example 12 | 24 wt % PRT410 × 4 | | 11.5 | 24.0 |
| Production Example 11 | 24 wt % PRT410 × 3 | 60 | 2.0 | 16.5 |
| Production Example 12 | 24 wt % PRT410 × 4 | | 10.8 | 25.0 |

TABLE 6

| Artificial fibroin fiber | | Temperature of water below boiling point (° C.) | Primary contraction (%) | Secondary contraction (%) |
|---|---|---|---|---|
| Production Example 13 | 24 wt % PRT399 × 1 | 20 | −3.5 | 7.6 |

TABLE 6-continued

| Artificial fibroin fiber | | Temperature of water below boiling point (° C.) | Primary contraction (%) | Secondary contraction (%) |
|---|---|---|---|---|
| Production Example 14 | 24 wt % PRT399 × 2 | | 3.7 | 12.5 |
| Production Example 15 | 24 wt % PRT399 × 3 | | 7.0 | 16.8 |
| Production Example 14 | 24 wt % PRT399 × 2 | 40 | 3.0 | 12.7 |
| Production Example 15 | 24 wt % PRT399 × 3 | | 7.3 | 16.7 |
| Production Example 14 | 24 wt % PRT399 × 2 | 60 | 3.3 | 9.3 |
| Production Example 15 | 24 wt % PRT399 × 3 | | 6.8 | 14.2 |

TABLE 7

| Artificial fibroin fiber | | Temperature of water below boiling point (° C.) | Primary contraction (%) | Secondary contraction (%) |
|---|---|---|---|---|
| Production Example 16 | 24 wt % PRT380 × 1 | 20 | −1.1 | 9.4 |
| Production Example 17 | 24 wt % PRT380 × 2 | | 2.7 | 13.3 |
| Production Example 18 | 24 wt % PRT380 × 3 | | 7.0 | 17.7 |
| Production Example 19 | 24 wt % PRT380 × 4 | | 10.0 | 20.2 |
| Production Example 17 | 24 wt % PRT380 × 2 | 40 | 3.3 | 14.2 |
| Production Example 18 | 24 wt % PRT380 × 3 | | 7.7 | 19.0 |
| Production Example 19 | 24 wt % PRT380 × 4 | | 12.0 | 22.0 |
| Production Example 17 | 24 wt % PRT380 × 2 | 60 | 2.7 | 14.3 |
| Production Example 18 | 24 wt % PRT380 × 3 | | 8.2 | 20.3 |
| Production Example 19 | 24 wt % PRT380 × 4 | | 12.0 | 23.2 |

The highly contracted artificial fibroin fiber of the present invention had a sufficiently high contraction percentage and was excellent in tactile properties and flexibility. In addition, the highly contracted artificial fibroin fiber can be produced safely because it can be manufactured by the contact step of being brought into contact with water below a boiling point, and the drying step of drying the artificial fibroin fiber after the contact step, if necessary.

REFERENCE SIGNS LIST

1: extrusion apparatus, 2: undrawn yarn production apparatus, 3: wet heat drawing apparatus, 4: drying apparatus, 6: dope solution, 10: spinning apparatus, 20: coagulation liquid tank, 21: drawing bath, 36: artificial fibroin fiber, 38: highly contracted artificial fibroin fiber, 40: production apparatus, 42: feed roller, 44: winder, 46: water bath, 48: dryer, 54: heater, 56: tension roller, 58: hot roller, 60: processing apparatus, 62: drying apparatus, 64: dry heat plate

The invention claimed is:

1. A method for producing a highly contracted artificial fibroin fiber, comprising:
   a step of contracting an artificial fibroin fiber containing a modified fibroin by bringing the artificial fibroin fiber into contact with water below a boiling point, wherein:
   the modified fibroin is a synthetically produced fibroin,
   the modified fibroin is a protein including a domain sequence represented by Formula: $[(A)_n$ motif-REP$]_m$, wherein $(A)_n$ motif indicates an amino acid sequence in which a percentage alanine residues is 40% or more with respect to the total number of amino acid residues, n is an integer of 2 to 20, REP represents an amino acid sequence consisting of 2 to 200 amino acid residues, m represents an integer of 2 to 300, a plurality of $(A)_n$ motifs is the same amino acid sequence or different amino acid sequences, and a plurality of REPs is the same amino acid sequence or different amino acid sequences,
   the modified fibroin is a fibroin whose domain sequence is different from the amino acid sequence of naturally occurring fibroin, and
   the modified fibroin has a contraction percentage defined by the following equation which exceeds 7%, contraction percentage={1−(length of contracted artificial fibroin fiber/length of artificial fibroin fiber before being brought into contact with water after spinning)}×100(%).

2. The method for producing a highly contracted artificial fibroin fiber according to claim 1, wherein the modified fibroin is a modified spider silk fibroin.

3. The method for producing a highly contracted artificial fibroin fiber according to claim 1, wherein a temperature of the water is 10° C. to 90° C.

4. The method for producing a highly contracted artificial fibroin fiber according to claim 1, wherein the step of contracting the artificial fibroin fiber further includes drying the artificial fibroin fiber after being brought into contact with the water.

5. A method for contracting an artificial fibroin fiber, comprising:
   a step of contracting an artificial fibroin fiber containing a modified fibroin by bringing the artificial fibroin fiber into contact with water below a boiling point,
   wherein:
   the modified fibroin is a synthetically produced fibroin,
   the modified fibroin is a protein including a domain sequence represented by Formula: $[(A)_n$ motif-REP$]_m$, wherein $(A)_n$ motif indicates an amino acid sequence in which a percentage alanine residues is 40% or more with respect to the total number of amino acid residues, n is an integer of 2 to 20, REP represents an amino acid sequence consisting of 2 to 200 amino acid residues, m represents an integer of 2 to 300, a plurality of $(A)_n$ motifs is the same amino acid sequence or different amino acid sequences, and a plurality of REPs is the same amino acid sequence or different amino acid sequences,
   the modified fibroin is a fibroin whose domain sequence is different from the amino acid sequence of naturally occurring fibroin, and the modified fibroin has a contraction percentage defined by the following equation which exceeds 7%, contraction percentage=$\{1-$(length of contracted artificial fibroin fiber/length of artificial fibroin fiber before being brought into contact with water after spinning)$\}\times 100(\%)$, 6. The method for contracting an artificial fibroin fiber according to claim 5, wherein the modified fibroin is a modified spider silk fibroin.

7. The method for contracting an artificial fibroin fiber according to claim 5, wherein a temperature of the water is 10° C. to 90° C.

8. The method for contracting an artificial fibroin fiber according to claim 5, wherein the step of contracting the artificial fibroin fiber further includes drying the artificial fibroin fiber after being brought into contact with the water.

* * * * *